United States Patent
Dudhia et al.

(10) Patent No.: US 8,688,199 B2
(45) Date of Patent: Apr. 1, 2014

(54) TISSUE ASSESSMENT

(75) Inventors: Jayesh Dudhia, London (GB); Paul Francis McMillan, London (GB); Edward Richard Cornell Draper, London (GB); Steven Firth, London (GB)

(73) Assignee: UCL Business PLC, London (GB)

( * ) Notice: Subject to any disclaimer, the term of this patent is extended or adjusted under 35 U.S.C. 154(b) by 311 days.

(21) Appl. No.: 12/992,342

(22) PCT Filed: May 13, 2009

(86) PCT No.: PCT/GB2009/001192
§ 371 (c)(1),
(2), (4) Date: Apr. 4, 2011

(87) PCT Pub. No.: WO2009/138738
PCT Pub. Date: Nov. 19, 2009

(65) Prior Publication Data
US 2011/0178379 A1    Jul. 21, 2011

(30) Foreign Application Priority Data
May 14, 2008    (GB) .................................. 0808711.6

(51) Int. Cl.
*A61B 5/00*    (2006.01)
*G01N 21/65*    (2006.01)

(52) U.S. Cl.
USPC ........... 600/475; 600/477; 600/473; 600/476; 600/407

(58) Field of Classification Search
USPC ...................... 600/473, 476, 407, 474, 477
See application file for complete search history.

(56) References Cited

U.S. PATENT DOCUMENTS

| | | | |
|---|---|---|---|
| 2002/0010400 A1* | 1/2002 | Camacho et al. | 600/473 |
| 2005/0119587 A1* | 6/2005 | Roessler et al. | 600/562 |
| 2007/0049808 A1* | 3/2007 | Roessler et al. | 600/315 |
| 2007/0082409 A1* | 4/2007 | Morris et al. | 436/171 |

FOREIGN PATENT DOCUMENTS

| | | |
|---|---|---|
| WO | WO 2006/036172 A1 | 4/2006 |
| WO | WO 2007/040589 A1 | 4/2007 |
| WO | WO 2007/113570 A1 | 10/2007 |

OTHER PUBLICATIONS

Bansil et al., Raman spectroscopy: a structural probe of glycomsaminoglycans, Biochim. Biophys. Acta, vol. 541, 1978, pp. 535-542.

Bay-Jensen et al., Biochemical markers of type II collagen breakdown and synthesis are positioned at specific sites in human osteoarthritic knee cartilage, Osteoarthritis. Cartilage. 2008, pp. 615-623.

Brandt, The importance of nonpharmacologic approaches in management of osteoarthritis, Am. J. Med., vol. 105, 1998, pp. 39S-44S.

(Continued)

*Primary Examiner* — Long V. Le
*Assistant Examiner* — Michael Kellogg
(74) *Attorney, Agent, or Firm* — Bell & Manning, LLC

(57) ABSTRACT

A method of aiding in the diagnosis or prediction of degenerative joint disease in a joint of a patient. The method comprises obtaining a test spectrum of Raman scattered radiation from cartilage tissue in the joint, and analyzing the test spectrum, or one or more regions thereof, to assess whether the test spectrum is consistent with the patient having, or subsequently developing, degenerative joint disease in the joint.

12 Claims, 25 Drawing Sheets

(56) References Cited

OTHER PUBLICATIONS

Cabassi et al., Infrared-Absorption and Raman-Scattering of Sulfate groups of Heparin and related Glycosaminoglycans in Aqueous-Solution, Carbohydrate Research, vol. 63, 1978, pp. 1-11.
Camacho et al., Fourier transform infrared imaging spectroscopy (FT-IRIS) of mineralization in biosphosphonate-treated oim/oim mice, Calcif. Tissue Int., vol. 72, Feb. 10, 2003, pp. 604-609.
Camacho et al., FTIR microscopic imaging of collagen and proteoglycan in bovine cartilage, Biopolymers, vol. 62, 2001, pp. 1-8.
Carden et al., Application of vibrational spectroscopy to the study of mineralized tissues (review), J. Biomed. Opt, vol. 5, Jul. 2000, pp. 259-268.
Clarke et al., Dual-energy X-ray absorptiometry applied to the assessment of tibial subchondral bone mineral density in osteoarthritis of the knee, Skeletal. Radiol., vol. 33, Jun. 24, 2004, pp. 588-595.
Davis et al., Can biochemical markers serve as surrogates for imaging in knee osteoarthritis? Arthritis Rheum., vol. 56, Dec. 2007, pp. 4038-4047.
F. de Groot, High resolution X-ray emission and X-ray absorption spectroscopy, Chemical Reviews, vol. 101, 2001, pp. 1779-1808.
Dehring et al., Identifying chemical changes in subchondral bone taken from murine knee joints using raman spectroscopy, Applied Spectroscopy, vol. 60, 2006, pp. 1134-1141.
Dehring et al., Correlating changes in collagen secondary structure with aging and defective type II collagen by Raman spectroscopy, Applied Spectroscopy, vol. 60, 2006, pp. 366-372.
Draper et al., Novel assessment of bone using time-resolved transcutaneous Raman spectroscopy, J. Bone Miner. Res., vol. 20, Jul. 18, 2005, pp. 1968-1972.
Felson et al., Osteoarthritis: new insights. Part 1: the disease and its risk factors, Ann. Intern. Med., vol. 133, Oct. 17, 2000, pp. 635-646.
Garnero et al., Relationships between biochemical markers of bone and cartilage degradation with radiological progression in patients with knee osteoarthritis receiving risedronate: the Knee Osteoarthritis Structural Arthritis randomized clinical trial, Osteoarthritis and Cartilage, vol. 16, 2008, pp. 660-666.
Garnero et al., Cross-sectional association of 10 molecular markers of bone, cartilage, and synovium with disease activity and radiological joint damage in patients with hip osteoarthritis: the ECHODIAH cohort, J. Rheumatol., vol. 32, 2005, pp. 697-703.
Gray et al., Magnetic resonance imaging of cartilage glycosaminoglycan: basic principles, imaging technique, and clinical applications, J. Orthop. Res., vol. 26, Sep. 17, 2007, pp. 281-291.
Henrotin et al., Type II collagen markers in osteoarthritis: what do they indicate? Curr. Opin. Rheumatol vol. 19, 2007, pp. 444-450.
Hunziker et al., Articular cartilage repair: basic science and clinical progress. A review of the current status and prospects, Osteoarthritis. Cartilage, vol. 10, 2002, pp. 432-463.
Kaminaka et al., Near-infrared multichannel Raman spectroscopy toward real-time in vivo cancer diagnosis, Journal of Raman Spectroscopy, vol. 33, 2002, pp. 498-502.
Kellgren et al., Radiological assessment of osteo-arthrosis, Ann. Rheum. Dis., vol. 16, 1957, pp. 494-502.
Koljenovic et al., Raman microspectroscopic mapping studies of human bronchial tissue, J. Biomed, Opt., vol. 9, Nov./Dec. 2004, pp. 1187-1197.
Lambert et al., Raman spectroscopy: the gateway into tomorrow's virology, Virol. J., vol. 3, Jun. 28, 2006.

Landewe et al., Presentation and analysis of radiographic data in clinical trials and observational studies, Ann. Rheum. Dis., vol. 64, 2005, pp. iv48-iv51.
Lawrence et al., Estimates of the Prevalence of arthritis and musculoskeletal disorders in the United States, Arthritis and Rheumatism, vol. 41, May 1998, pp. 778-799.
Lyng et al., Vibrational spectroscopy for cervical cancer pathology, from biochemical analysis to diagnostic tool, Exp. Mol. Pathol, vol. 82, Jan. 12, 2007, pp. 121-129.
Ma et al., UV resonance raman measurements of poly-L-lysine's conformational energy landscapes: Dependence on perchlorate concentration and temperature, Journal of Physical Chemistry B, vol. 111, Jun. 13, 2007, pp. 7675-7680.
Matousek et al., Subsurface probing in diffusely scattering media using spatially offset Raman spectroscopy, Applied Spectroscopy, vol. 59, 2005, pp. 393-400.
Matousek et al., Noninvasive Raman spectroscopy of human tissue in vivo, Appl. Spectrosc., vol. 60, 2006, pp. 758-763.
Mayer-Kuckuk et al., Molecular imaging promotes progress in orthopaedic research, Bone, vol. 39, Jul. 13, 2006, pp. 965-977.
McCreadie et al., Bone tissue compositional differences in women with and without osteoporotic fracture, Bone, vol. 39, Aug. 9, 2006, pp. 1190-1195.
Meziane-Tani et al., The SPASIBA force field for chondroitin sulphate: Vibrational analysis of D-glurcuronic and and N-acetyl-D-galactosamine 4-sulfate sodium salts, Journal of Physical Chemistry A, vol. 110, Sep. 14, 2006, pp. 11359-11370.
Mizuno et al., Near-infrared Fourier transform Raman spectroscopic study of cornea and sclera, Jpn. J. Opthalmol., vol. 38, 1994, pp. 44-48.
Morris et al., Special section guest editorial: Infrared and Raman Spectroscopy, J. Biomed. Opt., vol. 10, May/Jun. 2005, pp. 1.
Motz et al., Real-time Raman system for in vivo disease diagnosis, J. Biomed. Opt., vol. 10, May/Jun. 2005, pp. 1-7.
Palmer et al., Analysis of cartilage matrix fixed charge density and three-dimensional morphology via contrast-enhanced microcomputed tomography, Proc. Natl. Acad. Sci. U.S.A., vol. 103, Dec. 19, 2006, pp. 19255-19260.
Pelletier et al., In vivo suppression of early experimental osteoarthritis by interleukin-1 receptor against antagonist using gene therapy, Arthritis Rheum., vol. 40, Jun. 1997, pp. 1012-1019.
Poole, An Introduction to the pathophysiology of osteoarthritis, Front. Biosci., vol. 4, Oct. 15, 1999, pp. D662-D670.
Spahn et al., Near-infrared (NIR) spectroscopy. A new method for arthroscopic evaluation of low grade degenerated cartilage lesions. Results of a pilot study, BMC. Musculoskelet. Disord., vol. 8, May 29, 2007.
Spahn et al., Evaluation of cartilage defects with near-infrared spectroscopy (NIR): An ex vivo study, Med. Eng. Phys., vol. 30, 2008, pp. 285-292.
Takahashi et al., Relationship between radiographic grading of osteoarthritis and the biochemical markers for arthritis in knee osteoarthritis, Arthritis Res. Ther., vol. 6, Mar. 12, 2004, pp. R208-R212.
Yeni et al., Effect of fixation and embedding on Raman spectroscopic analysis of bone tissue, Calcified Tissue International, vol. 78, Jun. 21, 2006, pp. 363-371.
GB Search Report received in GB0808711.6, searched Jan. 28, 2009.
International Search Report received in PCT/GB2009/001192, mailed Aug. 17, 2009.
Ignatieva et al., Molecular processes and structural alterations in laser reshaping of cartilage, Laser Physics Letters, Oct. 2007, vol. 4, No. 10, Wiley-VCH Verlag GMBH Germany, pp. 749-753.

* cited by examiner

TISSUE ASSESSMENT

This application is a National Stage of International Application No. PCT/GB2009/001192, filed May 13, 2009, which claims the benefit of G.B. Application No. 0808711.6, filed May 14, 2008, the contents of which are herein incorporated by reference.

This invention relates to cartilage tissue and, more specifically, to the use of Raman spectroscopy to assess cartilage for the presence of degenerative joint disease.

The listing or discussion of an apparently prior-published document in this specification should not necessarily be taken as an acknowledgement that the document is part of the state of the art or is common general knowledge.

Degenerative joint disease (DJD) affects about 35 million people worldwide and is a major cause of pain and disability. Furthermore, with an aging population, its incidence is forecast to increase (Lawrence et al, 1989). Despite this, few treatments for this disease have been developed, with the medical approach being to tackle symptoms rather than the underlying disease mechanisms. This shortage of treatment development has been ascribed by many to the lack of objective assessments of disease progression (Takahashi at al, 2004), without which treatments cannot be evaluated. Furthermore, current assessment techniques such as plain X-rays or MRI only detect changes due to the disease over a period of about two years (Garnero et al, 2005) which is an inadequately short timeframe for monitoring disease progression either in the laboratory or within the clinic. Recent advances in systemic markers of cartilage turnover have proven to be better at monitoring more rapid changes disease, but these systemic techniques are not site-specific and are sensitive to cartilage turnover anywhere within the body, not just within the joint or joints being investigated.

Degenerative joint disease, also known as osteoarthritis or osteoarthrosis, is the most common disorder of the joints (Felson et al, 2000). In Western countries, radiographic evidence of the disease is present in the majority of people by 65 years of age and in about 80 percent of people over 75 years of age. Approximately 11 percent of people over 64 years of age have symptomatic osteoarthritis of the knee. Not only is DJD an extremely common form of arthritis, it is also a major cause of morbidity in the US and Europe.

DJD is caused by the breakdown and eventual loss of the cartilage of one or more joints causing pain, swelling and limitation of motion. The joints predominantly affected are weight-bearing and include the knees, hips, cervical and lumbosacral spine, and feet. Other affected joints include the distal and proximal interphalangeal joints of the hands.

DJD can be divided into primary and secondary forms, both forms sharing the same pathology. Primary DJD occurs in previously intact joints with no apparent initiating factor. It is related to the aging process and is more prevalent in older individuals. Secondary DJD refers to degenerative disease which results from some predisposing condition that has adversely altered the articular cartilage and/or subchondral bone of the affected joints. Such conditions can include obesity, repeated trauma or surgery to joint structures, diabetes, gout, abnormal joints at birth and other growth hormone disorders. Secondary DJD often occurs in relatively young individuals.

While many aspects of the aetiology of DJD remain unknown, certain aspects of its pathology and pathogenesis have been extensively studied (D'Ambrosia, 2005; Pelletier et al, 1997; Poole, 1999). During the course of DJD, small focal lesions develop typically within the cartilage layer. The initial process is the loss of proteoglycans from the extracellular matrix associated with a disruption of the collagenous fibrillar network followed by cell loss. These lesions gradually increase in area and depth until ultimately the entire thickness of the articular cartilage layer may be eroded (Hunziker, 2001). Changes in proteoglycans and the important sulphated glycosaminoglycans (GAGS) render the cartilage less resistant to compressive forces in the joint and more susceptible to the effects of stress, while reduced collagen levels place excessive stresses on the remaining fibres, eventually leading to mechanical failure. These changes, which involve loss of proteoglycans and GAGs, act with the increased water to soften the cartilage. The diminished mechanical integrity coupled with the cyclic nature of joint loading causes a cascade of degeneration.

The first microscopic evidence of DJD is flaking and fibrillations that develop along the normally smooth articular surface of the cartilage. This leads to a loss of the joint space with progressive erosion of the damaged cartilage occurring until finally the underlying bone is exposed. Bone denuded of its protective cartilage can continue to articulate with the opposing surface but tends to lead to discomfort or pain. Eventually, the increasing stresses exceed the biomechanical yield strength of the bone and the subchondral bone responds with vascular invasion and increased cellularity, becoming thickened and dense (eburnation) at areas of pressure. The traumatised subchondral bone may undergo cystic degeneration, due to either necrosis secondary to chronic impaction or the intrusion of synovial fluid. At non-pressure areas along the articular margin, vascularisation of subchondral marrow, metaplasia of synovial connective tissue and ossifying cartilaginous protrusions may also lead to irregular outgrowth of new bone or so-called osteophytes. Fragmentation of these osteophytes or of the articular cartilage itself results in intra-articular loose bodies.

With the continued expansion of the ageing population in the Western world, DJD is fast becoming a major medical and financial concern. Appropriate medical management requires that physicians be able to diagnose DJD early, recognise factors that may affect the prognosis or complicate the disease, and make effective use of the many available treatments. Currently, there is no single diagnostic test for DJD. Instead, a combination of clinical and imaging methods is used to aid diagnosis.

Clinical diagnosis currently involves assessing a range of clinical features including localised joint pain which worsens with activity, transient stiffness in the morning or after rest, a reduced range of motion, joint crepitus and/or periarticular tenderness and bone swelling. Joint misalignment may also be visible on physical examination (Brandt at al, 1998).

In addition to clinical signs of DJD there are several assessment modalities that aid the monitoring and diagnosis of the disease, which include plain X-rays, magnetic resonance imaging (MRI), dual energy X-ray absorptiometry (DXA), and systemic biomarkers of cartilage turnover. Of these the 'gold standard' is measurement of so-called "joint space" using plain radiography. The apparent space within the joint is in fact the thickness of the contacting cartilage layers (which are invisible to X-rays). Use of such joint space measurements has several methodological shortcomings (Davis at al, 2007) including: positional errors, intra- and inter-observer discrepancies, and "anticipation bias" during chronologic interpretation (Landewe & van der Heijde 2005). Since the changes in "joint space" are small in comparison with the precision error of plain X-ray measurements it can take between 1 and 3 years to detect such changes (Garnero at al, 2005, Henrotin at al, 2007). Nevertheless, until a more accurate and reproducible assessment is established, imaging using plain X-rays which are relatively inexpensive, readily accessible and easily performed remains the method of choice for routine monitoring and diagnosis of DJD.

DXA calculates bone mineral density (BMD) at specific regions of interest and it has been shown that increased BMD is associated with an increased severity score of the disease (Kellgren & Lawrence 1957). Like X-rays, however, DXA also has limitations. These include: positioning errors and the fact that being a radiographically-based assessment, cartilage is essentially invisible. Moreover, it has been shown that there is a significant overlap between BMD measurements for patients with and those without DJD (Clarke et al, 2004).

It has been shown that it is possible to use micro computerised tomography to detect changes in proteoglycans and sulphated GAGs (Palmer et al 2006). Such techniques require high doses of X-rays and contrast agents that are not suitable for clinical use.

MRI, unlike radiography, determines the full 3D geometry of cartilage tissue layer directly through its water content and produces excellent images of the joint and associated soft-tissue structures. It depicts the "joint space" and in addition can confirm the diagnosis of conditions such as avascular necrosis and soft tissue meniscal changes. Being a fully 3D modality, MRI is not subject to the positional errors of X-rays and DXA, but its usefulness as a measure of severity of DJD is still reliant on gross changes in cartilage thickness. It has the additional disadvantages of being relatively expensive and requiring a high level of skill to perform and interpret. While it is possible to indirectly assess the relative amount of GAGs within cartilage tissue using sodium MRI and delayed gadolinium-enhanced MRI (Gray et al 2007) both in vitro and in vivo, these techniques are both expensive and require a high level of expertise in MRI to perform.

Scintigraphy has been successfully used in the prognosis of DJD (Dieppe at al, 1993) giving an indication of the level of metabolic activity in the region around the joint or joints in question, but it is not in wide use because it requires a relatively high radiation dose.

None of these measurement techniques are able to detect changes in cartilage biochemistry such as loss of proteoglycans and breakdown of the collagen fibrillar network and the resulting loss of sulphated GAGs. This has led to increased interest in using biochemical markers of collagen and proteoglycan turnover. These markers are measured in blood, urine or synovial fluid samples and are molecules or molecular fragments produced when cartilage is being laid down or removed. The excitement at their possible future use stems in part from their ability to detect joint degenerative changes over only a few months rather than two years as required by the radiographically-based measurements (Takahashi at al, 2004). For example, as type II collagen of cartilage is synthesised and broken down, specific molecular fragments or epitopes are shed. With new sensitive techniques for measuring the levels of fragments the individual epitopes can be used as systemic biomarkers of cartilage turnover that can be measured in blood serum or urine. These biomarkers include: CTX-II, C2C, Coll2-1, Coll2-1NO2, Helix-II, PIIANP, and CPII, and it has been shown that using combinations of markers of synthesis and breakdown it is possible to determine cartilage turnover (Henrotin et al., 2007, Bay-Jensen et al, and Garnero et al, 2007). It has also been shown that because the changes in levels of these markers are greater than the precision errors of the measurement of their concentrations, these markers are more sensitive than X-rays, DXA and MRI, being able to detect changes in a matter of months rather than years. However, all such biomarkers suffer from the fundamental problem that they cannot be specific to any anatomical site and are sensitive to any cartilage turnover that is taking place anywhere within the body at the time of measurement.

In addition to these assessment and measurement techniques there is an additional avenue of investigation that helps in the assessment of DJD and that is arthroscopy. This is a minimally-invasive technique whereby a physician inserts a viewing scope into the joint space through a small incision. This allows the physician to examine the joint directly and to physically probe the cartilage surface to assess its physical properties and, from this, its level of degeneration. The first observable degenerative changes involve softening of the cartilage; later stages involve fibrillation and the appearance of fissures. These physical changes indicate that the degenerative cascade is already underway.

It would be of immense benefit to be able to detect changes in the underlying biochemistry of cartilage. In theory it is possible to extract small tissue biopsies from the joint surface for laboratory analysis, ideally from several sites across the joint surface to map the degeneration. However, since articular cartilage has a very poor healing reserve this is rarely performed.

Accordingly, there is an urgent need for an assessment technique that has the sensitivity of biomarkers, is able to detect the earliest stages DJD and to be specific in the anatomical site, not only to a specific joint but also across the joint surface.

Several spectroscopic techniques derived from physical chemistry approaches have been used to study and establish molecular-level differences in connective tissues, including Fourier transform infrared (FTIR) (Camacho et al., 2003), Near infrared (NIR) spectroscopy (Spahn et al 2007) and Raman scattering (McReadie et al, 2006) spectroscopies. These measurement modalities are increasingly important in the assessment of tissue at the molecular level (Mayer-Kuckuk & Boskey 2006). The FTIR and NIR techniques are based on the absorption of photons by characteristic vibrations of molecular components during transmission of the incident beam through the tissue, so is best used with trans-illumination of thin tissue sections in vitro. Furthermore, with FTIR spectroscopy the probe IR wavelengths are strongly and rapidly absorbed by water molecules or fluid within the tissue, so FTIR has been mainly used as an adjunct to histological imaging of tissues that are prepared as thin, dehydrated sections. NIR spectroscopy has been used with some success on ex vivo samples of cartilage (Spahn et al 2007, Spahn et al 2008) showing that changes in water content within the cartilage were associated with changes of the first OH and CH combination overtones (at 1340-1475 nm) relative to the second CH overtone (1150-1220 nm) (Spahn et al 2008).

Raman spectroscopy has been used for many years to probe the molecular structure and biochemistry of various biological tissues (Motz et al, 2005). The technique relies on inelastic scattering, or Raman scattering, of UV, visible or near-infrared light to provide information about the concentration of and the structure, bonding and local environment in organic and inorganic species by recording a spectrum of characteristic peaks due to their molecular vibrations. Raman scattering can also be excited by X-ray radiation that is commonly available from synchrotron sources (de Groot 2001). Typically, the vibrational spectrum is excited by illuminating a sample with monochromatic light that is usually provided by a laser. The incident probe laser light beam is focused on or inside the sample using a lens, or alternatively directed to the sample using an optical fibre. The light beam interacts with the sample, producing vibrational excitations that result in the incident laser wavelength and energy being shifted away from their initial values by small amounts corresponding to the vibrational energies of the sample. The result is a scattering of radiation from the excited region within the sample containing the spectrum of inelastically or Raman scattered wavelengths that correspond to the vibrational spectrum. Further details of the physical nature of the Raman scattering process and its application to understanding or monitoring the vibrational modes and molecular structures in samples and materials with applications including molecular biochemistry, medicine and biology are discussed and described in several standard textbooks including Tobin (1971), Hendra, Jones and Warnes (1991) and Long (2002).

Typically, the scattered light is collected, e.g. via a transmitting or reflective lens or though an optical fibre, and directed into a spectrometer, spectrograph or camera-based system that permits separation of the scattered light beam into its component wavelengths, allowing for detection of the relative positions and relative intensities of the different peaks corresponding to the characteristic vibrational modes within the sample. Wavelength separation may be achieved by the use of diffraction gratings, usually created or engraved using holographic techniques, and a monochromator or spectrograph system that employs multiple dispersion stages to achieve a high degree of resolution between the desired wavelengths and rejection of stray light signals from the incident laser. The radiation reflected from the gratings and dispersed into its component wavelengths is usually detected by a sensitive detector such as, but not limited to, an array of photosensitive diodes (a diode array detector) or a charge-coupled device (CCD).

Alternatively, a scanning spectrometer can be used, a slit in front of the detection device and scattered radiation dispersed into its component wavelengths being detected using a photomultiplier tube (PMT), usually in photon counting mode to improve the sensitivity. Such implementations of the technique may be useful, especially where an increased resolution between the wavelengths of the Raman scattered peaks in the inelastically scattered radiation is required.

As a further alternative, a Fourier transform technique may be employed to obtain Raman spectra, analogous to that developed for FTIR spectroscopy. In this method, the spectrum of Raman scattered radiation is directed into an interferometer rather than a spectrometer or spectrograph system. The scattered light beam that contains the entire spectrum of Raman scattered wavelengths is no longer separated spatially into its component wavelengths by a diffraction grating but instead is analysed using interferometric techniques using a Michelson interferometer or another interferometer design. The Michelson interferometer contains a beam-splitter that separates the beam of scattered light into two paths. One path is reflected from a static mirror and the second beam path is reflected from a moving mirror. The two light beams projected along each path are recombined at the beam-splitter according to a judicious arrangement of the reflected light pathways from the static and moving mirrors. The reflection of the incident light beam from the moving mirror induces a regular time-dependence in its signal of light intensity vs. time. Upon re-combination of the two reflected light beams (one from the static and one from the moving mirror) an interference pattern is generated that contains maxima and minima in its intensity as a function of the time during reflection of the light beam from the moving mirror, as a result of constructive and destructive addition or cancellation of waves between the two beams reflected from the two mirrors, as a function of their relative position or the path length travelled by the light wave between the beam-splitter and each mirror, that is therefore modulated by the time-dependent position of the moving mirror. The resulting interferogram then contains information on all of the scattered radiation wavelengths derived from the incident probe laser beam interaction with and inelastic or Raman scattering by the sample. The resulting interferogram is then compared with a standard interferogram obtained under similar conditions when no sample is present. The two (sample vs. standard) interferograms are usually divided or their logarithms are subtracted to provide a Raman spectrum of the sample itself. The resulting spectrum of Raman scattered intensity vs. the time variable used to complete each interferometer cycle is usually transformed into a scale of intensity vs. light frequency using mathematical Fourier transform techniques. Preferred data collection and analysis techniques include fast Fourier transform (FFT) methods that can be implemented using laboratory scale and commercially available computer systems. The implementation of such methodology using incident probe laser wavelengths in the near-infrared region for biochemical and biophysical studies related to bone and cartilage investigations and assessment has been described (e.g., Lambert et al, 2006).

The analysis of most biological samples by Raman spectroscopy was initially hampered by interference from background fluorescence. However, the problem of fluorescence can be overcome by careful selection of the wavelength of the probe laser to reduce fluorescence and by mathematical removal of any remaining fluorescence from the recorded spectra. The development of fibre optic probes and the extension of microprobe technology to spectroscopic imaging have increased the utility of Raman spectroscopy in medicine (Morris et al, 2005). Various Raman spectroscopy systems have now been developed for the ex vivo, and/or in vivo analysis of tissue, for example as described in WO 2004/051242, WO 2005/051182, WO 2004/064627, WO 2005/052558, WO 1995/11624, WO 2005/0090750 and WO 2004/0073120, and in Matousek et al (2006) and Motz et al (2005). Such advancements have seen a dramatic increase in the medical applications of Raman spectroscopy.

The Raman scattering effect occurs at wavelengths from the near infrared to ultraviolet and out to X-ray wavelengths. However, it is most commonly performed within the visible range of the electromagnetic spectrum, which can be selected appropriately for the study of interest. Recent studies of biological specimens including cartilage have selected as long a wavelength as possible in order to maximise penetration through the tissue of the incident and scattered beams, but at wavelengths that are short enough to avoid significant absorption by water, for example 785 nm near infra-red. The Raman effect involves inelastic photon scattering events between the incident laser beam and vibrational excitations of the sample, so that this form of spectroscopy can be performed on scattered photons returning to the surface but not necessarily along the same path as the incident probe laser. Recently, Raman spectra were recorded of skeletal tissue in vivo either by using ultra-high speed gating techniques on pulsed lasers (Draper et al, 2005) or by using spatially-offset Raman spectroscopy (SORS) (Matousek et al, 2006) in which Raman spectra of deep layers are extracted from those of more superficial layers by recording the spectra at distances that are at different offsets from the point of illumination. The Raman spectra of the superficial layers reduce in intensity more rapidly with offset than the spectra from deep layers; using mathematical techniques such as Primary Component Analysis (PCA), it is possible to extract the spectra from the deep layers. The Raman spectra of cartilage tissue lying deep to the surface can be recorded using this SORS technique.

Raman spectroscopy is especially suited to the diagnosis of various cancers, including intestinal, stomach, laryngeal, brain, breast, mouth and skin (Motz et al, 2005). Other applications include the assessment of bone quality for improved estimates of the risk of fracture, corneal hydration gradient analysis, rapid identification of bacteria and fungal infection, and even antibiotic susceptibility testing (Draper et al, 2005), by recording spectral changes associated with changes in molecular species within the tissues.

However, in in vitro studies all procedures for tissue fixation and preparation of skeletal tissue are known to affect the Raman spectral parameters (Yeni et al, 2006). Furthermore the penetration of the probe laser into cartilage tissue is a few millimeters, which leads to important scaling effects when results of small animal studies are applied to large animals such as humans and horses. In consequence, early attempts at the development of Raman spectroscopy of cartilage that used prepared samples from small animals cannot be applied directly to humans.

Nevertheless, Raman spectroscopy has been used to analyse subchondral bone in two transgenic mouse models, one of early onset DJD and one of lipoatrophy (Dehring et al, 2006a). In each case, femur condyles with articular cartilage intact were prepared in ethanol before analysis, and changes to the mineral content of the subchondral bone were identified, including subtle alterations in the carbonate-to-phosphate and the mineral-to-matrix ratios. Although collagen bands were observed, the authors stated that the similarities in Raman spectra from types I and II collagen complicated identification of individual contributions from cartilage and bone. Contributions from the polysaccharide components including proteoglycans and chondroitin sulphates were stated as being 'insignificant'. The authors stated that the absence of these components was consistent with their previous analysis of articular cartilage, and was also in accordance with a similar Raman based study of cornea and sclera (Mizuno et al, 2005). This stated lack of polysaccharide component within the Raman spectra of cartilage indicated that Raman spectroscopy is insensitive to this component, despite the fact that cartilage is rich in these polysaccharides (35% of dry weight and 4-7% of wet weight).

Polysaccharides of various forms have been studied using Raman spectroscopy. Bansil et al (1978) and Cabassi et al (1978) describe Raman spectroscopic analysis of purified proteoglycans and GAGs. Koljenović et al (2004) describes the Raman spectroscopic analysis of human bronchial tissue. Another study applied Raman spectroscopy to monitor damage to ocular collagen in a transgenic mouse model of osteoarthritis (Dehring et al, 2006b). Spectra of the sclera component of eyes indicated changes in collagen secondary structure in both the transgenic mice compared to age matched controls and in older wild type mice.

US 2007/0049808 (Roessler et al) describes a method of evaluating a connective tissue condition in a patient using Raman spectroscopy, in which tissue at one location is irradiated to generate spectral information which can be used as an indicator of the connective tissue condition at a second location of the body of the patient, remote from the first. The method does not disclose irradiating a particular joint directly in order to obtain information about that same joint.

US 2007/0049808 demonstrates that the amide III band area ratio (1240 cm$^{-1}$:1272 cm$^{-1}$), the amide I band area ratio (1685 cm$^{-1}$:1665 cm$^{-1}$) and the carbonate to phosphate ratio are increased in the Raman spectra of femurs (with articular cartilage intact) taken from Del1 (±) transgenic mice relative to wild type mice, while the mineral to matrix ratio is decreased. US 2007/0049808 also states that phosphate and carbonate peaks can be seen in spectra from cartilage. We note, however, that these chemical groups are not present in appreciable quantities within cartilage tissue; but are instead a major component of bone tissue within the apatite crystals of its mineral phase. While it is true that, for prepared murine joints, such peaks are apparent, this is due to the penetration of the probe laser down to the underlying bone. In contrast, we have found that, at laser powers that do not denature the collagen of the cartilage, in weight-bearing areas of the major joints of large animals such as humans and horses, phosphate and carbonate peaks do not become apparent until the cartilage surface is grossly eroded (FIG. 1).

Mizuno et al (1994), Dehring et al (2006b) and US 2007/0049808 all state that proteoglycans and GAGS make an insignificant contribution to the overall Raman spectrum of cartilage. While some of the known spectral components due to these molecules are not prominent in the complex cartilage spectra, we have unexpectedly and surprisingly shown that peaks associated with the sulphate groups on these molecules are readily visible in cartilage spectra (FIG. 2), and that they vary consistently with cartilage degradation and the loss of proteoglycans.

The approach followed in US 2007/0049808 of recording spectra at one anatomical site to assess the predisposition to cartilage degeneration at another site allowed its authors to suggest which spectral features may be useful in establishing such predisposition. That work, however, could not lead to a method of assessment of cartilage health directly for two fundamental reasons: firstly, the findings pertain not to current levels of degeneration but to predisposition to future degeneration, and secondly the spectral features of cartilage that pertain to predisposition to degeneration are not the same as the spectral features of cartilage once the tissue has begun to degenerate.

Thus, there is a need in the art for a rapid, site-specific, preferably non-invasive, or at least minimally-invasive, method for assessing cartilage degeneration within a joint, particularly in the early stages of DJD.

As part of a study to identify biochemical changes associated with DJD, we (i.e. the present inventors) recorded Raman spectra from samples of human joints, in particular the knee. These were full thickness samples of the joint surface down to and including the subchondral bone. Using samples from amputations performed for non-orthopaedic reasons we were able to study levels of degeneration from full health to complete lesions with complete cartilage erosion. The age range of the donors was from 18 to 74 years. Surprisingly and unexpectedly, we identified major differences between Raman spectral features of cartilage that correlated with cartilage degeneration. We found differences when examining joints with focal lesions in spectra from full thickness cartilage outside the lesion, the edge of lesion and to a site about the centre of the lesion. We also showed that the spectral features of cartilage recorded outside the focal lesion, but from a joint in which a lesion was present, displayed differences from those taken from healthy joints in which no such lesions were present; thus indicating early degenerative changes.

We have shown a strong peak at about 1,063 cm$^{-1}$ (FIG. 3) associated with the symmetric S—O stretching vibration of the sulphate groups on proteoglycans and GAGs (Bansil at al, 1978; Koljenovic et al, 2004; Meziane-Tani at al, 2006) which varies consistently with cartilage degradation and its loss of proteoglycans. We also detected a decrease in the area of this main sulphate band relative to the area of collagen bands with progress of disease and reduction of proteoglycan and GAG content of the cartilage tissue. Loss of GAGs is known to happen early in the pathogenesis of DJD, but it is currently undetectable except by biopsy.

Furthermore, we have shown that outside the so-called "fingerprint" region of the spectrum which lies between about 500 and 1,700 cm$^{-1}$ (Lyng et al, 2006), there is important information regarding the tissue's water content. We detected increases in water content of the cartilage tissue with progress of the disease through increases of area of the bands associated with water relative to those associated with collagen. Increased water content occurs as DJD progresses. Furthermore we detected changes in the areas of the two components of the OH stretch complex lying with its centre around 3,210 cm$^{-1}$ (FIG. 2), which is in keeping with changes in the manner in which the water is bound within the tissue.

Thus we have recognised that a full site-specific assessment of cartilage tissue using Raman spectroscopy may advantageously include analysis of the symmetric SO stretch of sulphate band at about 1,063 cm$^{-1}$ and/or the OH stretch complex at about 3,200 cm$^{-1}$.

We detected a decrease in the area of the proline band relative to that of the hydroxyproline band. These molecular species are cyclic in nature and these bands are due to characteristic C—C stretch within this ring, with the post-translational hydroxylation of the γ carbon causing the characteristic shift within the hydroxyproline band. Since hydroxyproline is present in collagen but not in proteoglycans such decreases are indicative of the early molecular changes in collagen fibrillar network and changes in the collagen to proteoglycan ratio, known to occur early in DJD.

We detected characteristic bands that indicate phosphate (at about 960 cm$^{-1}$) and carbonate (at about 1,068 cm$^{-1}$) species bands in the weight-bearing regions of cartilage only if there was sufficient erosion of the cartilage tissue allowing the spectrum of the underlying bone to appear.

Assessing the presence or absence of any or all of these changes in the cartilage of a particular joint in vivo provides valuable indications of the health of the cartilage in that joint. Furthermore, since such changes can occur early in the pathogenesis of DJD, and before current methods of assessments can detect such changes, they provide valuable markers of the early stages of the onset of the disease.

Since such changes are detectable using Raman spectroscopy across the surface of the joint assessed, it is possible to measure progress of the disease at any one point on the joint surface and also to map how focal lesions change in shape and size.

Accordingly, a first, aspect of the invention provides a method of diagnosing or predicting degenerative joint disease (DJD) in a joint of a patient, the method comprising:

obtaining a test spectrum of Raman scattered radiation from cartilage tissue in the joint; and analysing the test spectrum, or one or more regions thereof, to assess whether the test spectrum is consistent with the patient having, or subsequently developing, DJD in the joint.

As used herein, a "test spectrum" is a spectrum of Raman scattered radiation obtained from the cartilage tissue of the joint in a patient to be assessed.

By determining whether the test spectrum, or the one or more regions thereof, is consistent with the patient having DJD in a joint, we mean that the method can be used to assess the presence of DJD in the cartilage tissue of the joint. Typically, the method is used to determine if a joint has DJD, or not, in patients who are presenting one or more symptoms of DJD in the joint such as pain especially localised joint pain which worsens with activity, transient stiffness, a reduced range of motion, joint crepitus and/or periarticular tenderness, bone swelling or joint misalignment, but a diagnosis of DJD cannot be definitively made. For example, using currently available methods of diagnosing DJD it may be difficult to distinguish DJD from other conditions, such as rheumatoid arthritis, psoriatic arthritis or septic arthritis, that display similar symptoms. Thus, the invention may be said to include a method of distinguishing DJD from these other conditions. The method may thus be used in combination with other diagnostic methods to aid the physician in making a diagnosis of DJD, such as immunological investigations, investigations of infection and assessment of other joints especially the contralateral joint.

In other words, the invention includes a method of aiding in the diagnosis or prediction of DJD in a joint of a patient, the method comprising:

obtaining a test spectrum of Raman scattered radiation from cartilage tissue in the joint; and analysing the test spectrum, or one or more regions thereof, to assess whether the test spectrum is consistent with the patient having, or subsequently developing, DJD in the joint.

By determining whether the test spectrum, or the one or more regions thereof, is consistent with the patient subsequently developing DJD in a joint, we mean that the method can be used to assess whether there is an increased likelihood that a patient presenting no clinical symptoms of DJD in a joint will develop DJD in that joint within the following 1, 3 or 5 years. Thus, although the patient may be 'negative' for all currently available diagnostic tests for DJD, it may be desirable to predict the likelihood of DJD developing in the future. This patient typically does not have any of the clinical symptoms of DJD in a joint such as pain especially localised joint pain which worsens with activity, transient stiffness, a reduced range of motion, joint crepitus and/or periarticular tenderness, bone swelling or joint misalignment.

The patient to be tested for a prediction of DJD may be one who is considered to be at risk of DJD, for example, due to a family history of DJD, a history of high levels of joint loading through physical activities such as weight-lifting or professional football, obesity, repeated trauma or surgery to joint structures, diabetes, gout, abnormal joints at birth and other growth hormone disorders. In these cases, it may be useful to assess the patient's likelihood of developing to DJD from measured early degenerative changes in articular cartilage.

The ability to detect evidence of the early stages of DJD in a patient will allow early pharmaceutical treatments to be evaluated. Furthermore, being able to show at this early stage whether the cartilage degeneration improves or deteriorates will allow the provision of objective evidence that is required for the future development of pharmacological interventions for DJD.

It is appreciated that the method of the invention may identify patients having only a low risk of developing DJD, as well as patients having an increased risk of developing DJD. It will be appreciated that no methods can predict with 100% certainty whether a patient will develop DJD since patients' lifestyles, which impact upon the development of DJD, may change. Indeed, if a patient is found to be at increased risk of developing DJD, the patient may be advised to change their lifestyle in an attempt to delay the onset of the disease.

The joint may be any joint of the body that is typically affected by DJD, for example the joint may be a knee, hip, elbow, shoulder, cervical, thoracic or lumbosacral spine joint, or a joint within the foot or hand.

The spectrum of Raman scattered radiation can be obtained by irradiating cartilage tissue in a joint with a probe light source, normally a laser, and detecting a spectrum of Raman scattered radiation emitted from the tissue, although not necessarily from the same point or area as illuminated. Suitable apparatus for irradiating cartilage tissue and detecting a spectrum of Raman scattered radiation emitted from the tissue are described herein and, for example, in WO 2004/051242, WO 2004/064627, WO 2005/052558, WO 1995/11624, WO 2005/0090750 and WO 2004/0073120, and in Matousek et al (2006) and Motz et al (2005).

The spectrum of Raman scattered radiation can be obtained from a patient and analysed directly, or it can be obtained from a patient and stored on a local or remote database for later analysis. Thus, the Raman spectra could be transmitted via a computer-based network such as the internet to a remotely-located device for carrying out the comparison and assessment steps, for example. Thus, in an embodiment, obtaining a spectrum of Raman scattered radiation from cartilage tissue in a joint may comprise providing a previously obtained Raman spectrum from the joint. In other words, this aspect of the invention includes a method of diagnosing DJD, or aiding in the diagnosis of DJD, in a joint of a patient, the method comprising analysing a test spectrum of Raman scattered radiation previously obtained from cartilage tissue in the joint, or one or more regions thereof, to assess whether the test spectrum is consistent with the patient having, or subsequently developing, DJD in the joint.

To maximise the efficiency, the irradiation of cartilage tissue to be examined should be at light levels at an intensity that is low enough to avoid tissue damage or any patient discomfort. It is appreciated that visible and IR light can be: 1) readily passed through space in a controlled manner using mirrors, prisms and other optical elements or 2) readily passed though optical fibres. In this way the light source is typically positioned a short distance away from the joint, typically within a few meters. Similarly, it is appreciated that a receiver (or detector), or an optical probe that is optically coupled to a receiver, is typically also positioned close to the joint, typically within a few meters. In addition the optical probe could be optically coupled to both the light source and the receiver in such a way that the probe light can be passed to the cartilage tissue and the scattered Raman photons can be collected through the same probe, but not necessarily from the same point.

In one preferred embodiment, the analysing step comprises comparing the test spectrum or the one or more regions thereof to a standard spectrum of Raman scattered radiation or to one or more respective regions thereof.

By "standard" spectra of Raman scattered radiation we mean spectra that have been obtained from cartilage of known condition. Thus, for example, by comparing a test spectrum of Raman scattered radiation, or one or more regions thereof, with one or more standard spectra obtained from healthy cartilage or cartilage with known degenerative changes, or respective regions thereof, it is possible to assess whether a particular joint does or does not have DJD or is at risk of developing DJD. It is preferred that the test spectrum, or one or more regions thereof, is compared with a standard spectrum from healthy tissue and a standard spectrum from cartilage with known degenerative changes, or the respective regions thereof.

It is preferred if the standards have been acquired under the same conditions and using the same apparatus as the spectrum of Raman scattered radiation obtained from the cartilage in the joint. However, it will be appreciated that any systematic variation arising from data acquisition may be accounted for by appropriate calibration.

The standard spectrum may comprise the Raman scattered radiation from cartilage in one control individual. However, to generate a representative standard, it is preferred if the standard spectra represents an average of a plurality of spectra obtained from cartilage tissue from a plurality of individuals. Preferably, the standard spectra are the average (e.g. means) of Raman scattered radiation from cartilage in a joint from a population of control individuals, with each member of the population having the same level of degenerative features in the joint, suitable determined by having the same severity score for DJD, such as the Kellgren Lawrence score, ICRS score or the OARSI score, in the joint. Preferably, the population of control individuals comprises at least 5, 10, 50, 100, 200, 300, 400 or 500 individuals, and more preferably at least 1,000 individuals. The means of band area, width, height and position (in terms of wavenumber) of the spectra may be calculated manually, i.e. by summing the intensities at each wavenumber from each spectrum and dividing by the number of individuals, or automatically using any of the software packages described herein. Alternatively, the mean of the sample population of each spectral feature including band area, band width, band height and band position can be calculated either manually or automatically. Furthermore, while it is not preferred, the band area can be estimated from the band width and the band height.

At the same time as each mean is calculated, a measure of variation of the measurement in question across the group is usually made, being for example the standard deviation or some other measurement of variation across the group such as a standard error of the mean.

Preferably, the standard spectra are from cartilage of the same species as the patient being tested. Thus, if the joint tested is a human joint, it is preferred if the standard spectrum is Raman scattered radiation from a human joint. It is further preferred if the control individuals are the same or similar age, weight, height and racial background as the patient that is being tested. Preferably, the standard spectra are from cartilage of the same joint as that being investigated in the patient being tested. Thus, if the joint tested is a knee joint, it is preferred if the standard spectra are Raman scattered radiation from a knee joint.

The healthy or "non-DJD" standard spectrum of Raman scattered radiation is typically the mean Raman scattered radiation spectra from the joint of one or a population of control individuals that do not have DJD. It is preferred if the individuals are assessed using the earliest detection techniques (e.g. a combination of radiography and MRI) for DJD available, other than the methods of the present invention, and confirmed not to have DJD.

A further suitable "non-DJD" standard may be the mean Raman scattered radiation from the joint of one or a population of control individuals that do not have DJD, as evidenced using the earliest detection techniques currently available (e.g. a combination of radiography and MRI), and thereafter have been shown not to develop DJD using the same techniques. Preferably, the individual(s) have been shown not to develop DJD for at least 6 months, or 1, 2, 3 or 4 years, or more preferably for a period of 5 years, or more, as determined using the same detection techniques.

In addition, it is preferred if the individual(s) in the "non-DJD" standard have no or few risk factors for DJD, including obesity, repeated trauma or surgery to joint structures, diabetes, gout, abnormal joints at birth, or growth hormone disorders.

"DJD" standard spectra of Raman scattered radiation are typically the mean Raman scattered radiation spectra from cartilage in one or a population of control individuals that have been diagnosed as having DJD and have been given a severity score for DJD, such as the Kellgren Lawrence score, with a separate mean calculated for each group of patients with the same severity score.

A further suitable "DJD" standard spectrum of Raman scattered radiation may be the mean Raman scattered radiation spectra from cartilage in one or a population of control individuals that did not have clinical symptoms of DJD, e.g. as described above, but who developed DJD within the subsequent 6 months, or subsequent 1, 2, 3, 4 or 5 years.

Comparing the obtained test spectrum of Raman scattered radiation, or the one or more regions thereof, with "non-DJD" and/or "DJD" standard spectra may be used to assess the level of degenerative features of the tissue and whether or not these degenerative features are consistent with the patient having DJD in a particular joint. A comparison with the standard spectra can also be used to assess the likelihood of patient with no clinical symptoms developing DJD in a particular joint.

By the test spectrum, or regions thereof, being "consistent" with the patient having, or subsequently developing, DJD in the joint, we mean that the test spectrum as a whole or specific features thereof correlates to a statistically acceptable level with a standard spectrum, or specific features from a standard spectrum, that have previously been demonstrated to indicate the presence of DJD in the joint. Thus, for example, a test spectrum obtained from cartilage in a joint that is statistically similar to "DJD" standard spectra and/or is statistically different from "non-DJD" standard spectra indicates that the individual has, or is at an increased risk of subsequently developing, DJD in that joint. Conversely, a test spectrum of Raman scattered radiation obtained from cartilage in a joint that is statistically similar to a "non-DJD" standard spectrum and/or is statistically different from a "DJD" standard spectrum indicates that the individual does not have, or is at a low risk of subsequently developing, DJD in that joint.

In an alternative preferred embodiment, by the test spectrum, or regions thereof, being "consistent" with the patient having or subsequently developing DJD in the joint, we mean that specific spectral features of the test spectrum lie on the side of an "indicator level" for that spectral feature which indicates degeneration and DJD. Typically, the "indicator levels" have been determined from one or more populations of control individuals which comprises at least 5, 10, 50, 100, 200, 300, 400 or 500 individuals, and more preferably at least 1,000 individuals. Thus, for example, a spectral feature in a test spectrum of Raman scattered radiation obtained from cartilage in a joint that lies on the 'DJD' side of one or more indicator levels indicates that the individual has, or is at an increased risk of subsequently developing, DJD in that joint. Conversely, a spectral feature in the test spectrum that lies on the 'healthy' or 'non-DJD' side of one or more indicator levels indicates that the individual does not have, or is at a low risk of subsequently developing, DJD in that joint.

Spectra of Raman scattered radiation can be visualised and compared using computer software packages well known in the art, for example OriginPro7 (OriginLab Corp, USA), OMNIC Professional software suite (Thermo scientific), GRAMS/AI, (Thermo Galactic, Madison, Wis.), Microsoft Excel, MatLab (Mathsworks), ACD/UV-IR Manager (Advancer Chemistry Development) and other mathematical software. Spectra may be visually compared or compared using automated computer based algorithms in suitable software packages.

Preferably, the test spectrum of Raman scattered radiation is processed by a spectral analyser, such as described below, to generate a spectrum containing a plurality of bands corresponding to one or more wavenumbers, each of which represents a particular chemical moiety. Since the area of the bands is directly proportional to the concentration of particular molecular vibrations, differences in band intensities, and differences in ratios of band intensities, can be used to determine differences in the molecular composition of samples.

As shown in FIG. 1, there are important spectral features that lie outside the so-called "fingerprint" region which extends from about 400 cm$^{-1}$ to about 1,800 cm$^{-1}$. It can also be seen that the background fluorescence is lowest outside the "fingerprint" region, i.e. at wavenumbers greater than around 2,000 cm$^{-1}$. We have therefore recognised that, contrary to previous experience, it is possible to determine important parameters relating to degenerative joint disease outside the conventional fingerprint region. This has the advantage of requiring less (or no) adjustment for background fluorescence, and therefore allows the required signals to be more readily determined. As shown in more detail below, a preferred region within which to determine signs of joint degeneration is at wavenumbers greater than 1,800 cm$^{-1}$, preferably greater than 2,000 cm$^{-1}$ or greater than 2,500 cm$^{-1}$, and suitably at wavenumbers between 2,500 cm$^{-1}$ and 3,500 cm$^{-1}$. We are not aware of any previous work which demonstrates that wavenumbers within these regions can provide any indication of DJD.

In an embodiment, the step of obtaining a test spectrum of Raman scattered radiation will include any one, two, three, four, five, six or all seven of the following:

determining the area of at least one band from the test spectrum; and determining the area of at least two bands from the test spectrum and calculating a ratio of areas of the at least two bands from the test spectrum; and determining the height of at least one band from the test spectrum; and determining the height of at least two bands from the test spectrum and calculating a ratio of heights of the at least two bands from the test spectrum; and determining the width of at least one band from the test spectrum; and determining the width of at least two bands from the test spectrum and calculating a ratio of widths of the at least two bands from the test spectrum, and determining the position (mean wavelength) of at least one band from the test spectrum.

Typically, the area of at least one band from the test spectrum is determined, and preferably, at least one ratio of areas of at least two bands from the test spectrum is determined.

Various techniques are available in the art to determine the intensity of bands in Raman spectra. By "intensity", we mean the number of photons that have been recorded that are associated with any particular spectral feature; normally this is calculated by the area of the band but can also be estimated from band width and height. For example, well established curve-fit routines may be applied to determine band areas including that in the GRAMS/AI (ThermoGalactic) software based on fitting band envelopes to mixed Gaussian/Lorentzian functions, or the Lorentzian curve fitting tool described in Example 1. Other appropriate curve-fitting methods are well known in the art and are described for example in Ferry et al (1995) and Vickers et al (2001). Alternatively, the area may be measured without curve fitting. For example, the area could be measured based on the raw data. As another example, the raw data could be filtered (e.g. with a smoothing filter) in order to reject high-spatial frequency noise without introducing detectable distortions, and the area measured based on the filtered data, with or without the removal of the background fluorescence. Various smoothing algorithms are well known in the art and include, for example fast Fourier transform and Savitsky-Golay functions. Alternatively, intensity of bands can be estimated by calculating band height or by multiplying band height by band width with or without using a standard correction factor. The area under one or more bands may be determined using any of a variety of well known techniques. Thus, determining the intensity of a band from the tissue may comprise one or more of fitting a curve to the band, calculating the area of the band, or calculating the height of the band.

It is appreciated that while the intensity of bands may be determined manually, an automated process is preferred, both for speed and to eliminate the possibility of human error. Several software packages are capable of calculating band intensities including OriginPro7 (OriginLab Corp, USA), OMNIC Professional software suite (Thermo scientific), ACD/UV-IR Manager (Advancer Chemistry Development) and OPUS (Bruker).

It is appreciated that the standard spectra of Raman scattered radiation typically also comprise a plurality of bands corresponding to one or more wavenumbers. Thus, comparing the test spectrum or the one or more regions thereof to a standard spectrum or one or more respective regions thereof typically comprises any one, two, three, four, five, six or all seven of:

comparing the area of at least one band from the test spectrum to the area of at least one corresponding band from the standard spectrum;

comparing the ratio of areas of at least two bands from the test spectrum to the ratio of the areas of at least two corresponding bands from the standard spectrum;

comparing the height of at least one band from the test spectrum with the height of at least one corresponding band from the standard spectrum;

comparing the ratio of heights of at least two bands from the test spectrum to the ratio of heights of at least two corresponding bands from the standard spectrum;

comparing the width of at least one band from the test spectrum to the width of at least one corresponding band from the standard spectrum;

comparing a ratio of widths of at least two bands from the test spectrum to the ratio of the widths of at least two corresponding bands from the standard spectrum; and comparing the position of at least one band from the test spectrum to the position of at least one corresponding band from the standard spectrum Typically, the area of at least one band from the test spectrum is compared to the area of at least one corresponding band from the standard spectrum. Preferably, at least one ratio of areas of at least two bands from the test spectrum is compared to the ratio of the areas of at least two corresponding bands from the standard spectrum.

The area of a band or a ratio of areas of bands can be compared between the test and standard spectra by various methods known in the art. For example, the measured spectral feature, such as the area of the main sulphate peak or ratio of the area of this peak to a collagen peak such as the phenylalanine ring breathing band, can be compared with the area of the corresponding band or ratio of bands of the standard spectra of healthy cartilage as well as standard spectra of cartilage with known loss of sulphate and other degenerative features, and by such comparison determine the most likely level of sulphate within the cartilage being measured. Thus the most likely level of degeneration of the cartilage tissue being measured can be ascertained. Similar approaches to other individual bands or ratio of bands can then be repeated to ascertain the level of degeneration as estimated be each feature. The overall level of degeneration can be taken as an average such as a median or mode level of degeneration as estimated from each spectral parameter or ratio of parameters.

Alternatively, for example, the measured intensity as measured by band area or band area ratio may be compared to the mean intensity or ratio of intensities of the corresponding band(s) in the standard spectra of Raman scattered radiation by taking into account the standard deviation (SD) about the mean. If the intensity or ratio of intensities does not lie within the mean, plus or minus a multiple of the SD, the difference may be said to be real. Common multiples of the SD include 1 SD, 2 SD or 3 SDs. Alternatively, statistical tests may be applied to determine if there is a significant difference in the intensity of a corresponding band between two spectra. Such tests may employ varying levels of statistical significance, for example 5%, 1% and 0.1% as is well known in the art. Examples of appropriate tests include univariate tests such as Student's t-test, the Kruskal-Wallis test and the Kolmogorov-Smirnov test or multivariate tests such as independent components analysis (ICA), principal components analysis (PCA) and hierarchical cluster analysis (HCA).

Typically in biological applications, a difference is said to be real if it does not lie within the mean, plus or minus 2 SDs, or if it is statistically significant at the 5% level of significance.

Thus, typically, when comparing to a "non-DJD" standard, the intensity of a band or ratio of intensities in the test spectrum that is indicative that a patient has DJD or an increased likelihood of developing DJD in the joint, is an intensity or ratio of intensities that is outside ±2 SD of the mean of the intensity or ratio of intensities of the corresponding band(s) in the non-DJD standard spectrum. The intensity of a band or ratio of intensities in the test spectrum that is indicative that a patient does not have DJD or has no increased likelihood of developing DJD in that joint is an intensity or ratio of intensities that is within 2 SD of the mean of the intensity or ratio of intensities of the corresponding band(s) in the non-DJD standard spectrum of Raman scattered radiation.

When comparing to a "DJD" standard, the intensity of a band or ratio of intensities in the test spectrum that is indicative that a patient has DJD or an increased likelihood of developing DJD in the joint is an intensity or ratio of intensities that is within 2 SD of the mean of the intensity or ratio of intensities of the corresponding band(s) in the standard spectrum. The intensity of a band or ratio of intensities in the test spectrum that is indicative that a patient does not have DJD, or has no increased likelihood of developing DJD, is an intensity or ratio of intensities that is outside ±2 SD of the mean of the intensity or ratio of intensities of the corresponding band(s) in the DJD standard spectrum of Raman scattered radiation.

It will be appreciated that it may be desirable to compare the test spectrum with both "DJD" and "non-DJD" standards. In this case, the intensity of a band or ratio of intensities in the test spectrum that is indicative that a patient has DJD, or has an increased likelihood of developing DJD, in the joint, is an intensity or ratio of intensities that is within 2 SD of the mean of the intensity or ratio of intensities of the corresponding band(s) in the DJD standard spectrum, but which is outside ±2 SD of the mean of the intensity or ratio of intensities of the corresponding band(s) in the non-DJD standard spectrum. Conversely, the intensity of a band or ratio of intensities in the test spectrum that is indicative that a patient does not have DJD or has no increased likelihood of developing DJD in the joint is an intensity or ratio of intensities that is within 2 SD of the mean of the intensity or ratio of intensities of the corresponding band(s) in the non-DJD standard spectrum, but which is outside ±12 SD of the mean of the intensity or ratio of intensities of the corresponding band(s) in the DJD standard spectrum.

We have identified a number of changes in the Raman spectra of cartilage in joints with DJD which may be used as indicators of cartilage degeneration in the same joint. Specifically, we demonstrated that the position and area of the following bands varied with level of cartilage degeneration (FIGS. 3 to 22): the phenylalanine ring breathing at about $1,003$ cm$^{-1}$, indicating the amount of collagen within the tissue; the main symmetric SO stretch of sulphate band at about $1,063$ cm$^{-1}$; the area and position of a band due to amide III at about $1,272$ cm$^{-1}$; and the area and position of a band due to amide I at about $1,665$ cm$^{-1}$.

We have also identified that the ratio of areas of the following bands varied with cartilage degeneration, and may be used as indicators of cartilage degeneration (FIGS. 23 to 32):

the ratio of the area of the band due to H$_2$O bend at about $1,637$ cm$^{-1}$ to the area of the phenylalanine ring breathing band at about $1,003$ cm$^{-1}$, this ratio gives a measure of cartilage hydration;

the ratio of the area of the low-wavenumber band of the O—H stretch complex at about $3,200$ cm$^{-1}$ to the area of the CH stretch at about $2,940$ cm$^{-1}$ (the spectral complex of the three bands at about $2,889$ cm$^{-1}$, $2,940$ cm$^{-1}$ and $2,980$ cm$^{-1}$ are collectively referred to within this document as the CH stretch band), this ratio gives another measure of cartilage hydration;

the ratio of the area of the symmetric SO stretch of sulphate band at about $1,063$ cm$^{-1}$ to the area of the phenylalanine ring breathing band at about $1,003$ cm$^{-1}$, this ratio will be directly related to the tissue concentration of sulphate and, in turn, directly related to the amount of proteoglycans and GAGs within the tissue;

the ratio of the area of the low-wavenumber band of the O—H stretch complex at about $3,210$ cm$^{-1}$ to the area of the high-wavenumber band of the O—H stretch complex at about $3,380$ cm$^{-1}$, changes in this ratio are commensurate with changes in the way in which water is bound within the tissue; and the ratio of the area of the proline band at about $856$ cm$^{-1}$ to the area of the hydroxyproline band at about $877$ cm$^{-1}$, changes in this ratio is commensurate with changes in the collagen fibrillar network and the collagen to proteoglycan ratio.

Accordingly, the obtaining step typically comprises:

obtaining (i.e., determining or being provided with) any one, two, three, four, five, six, seven, eight, nine, ten, eleven, twelve, thirteen, fourteen or preferably all fifteen of:

(a) the area and position of a proline band at about $856$ cm$^{-1}$;

(b) the area and position of a hydroxyproline band at about $877$ cm$^{-1}$;

(c) the area and position of a phenylalanine ring breathing band at about $1,003$ cm$^{-1}$;

(d) the area and position of a symmetric SO stretch of sulphate band at about $1,063$ cm$^{-1}$;

(e) the area and position of a band due to amide III at about $1,272$ cm$^{-1}$;

(f) the area and position of a band due to H$_2$O bend at about $1,637$ cm$^{-1}$;

(g) the area and position of a band due to amide I at about $1,665$ cm$^{-1}$;

(h) the area and position of a CH stretch band at about $2,940$ cm$^{-1}$;

(i) the area and position of the low-wavenumber band of an O—H stretch complex at about $3,210$ cm$^{-1}$; and (j) the area and position of the high-wavenumber band of an O—H stretch complex at about $3,380$ cm$^{-1}$.

(k) the ratio of the area of the band due to H$_2$O bend at about $1,637$ cm$^{-1}$ to the area of the phenylalanine ring breathing band at about $1,003$ cm$^{-1}$;

(l) the ratio of the area of the low-wavenumber band of the O—H stretch complex at about $3,210$ cm$^{-1}$ to the area of the CH stretch at about $2,940$ cm$^{-1}$;

(m) the ratio of the area of the symmetric SO stretch of sulphate band at about $1,063$ cm$^{-1}$ to the area of the phenylalanine ring breathing band at about $1,003$ cm$^{-1}$;

(n) the ratio of the area of the low-wavenumber band of the O—H stretch complex at about $3,210$ cm$^{-1}$ to the area of the high-wavenumber band of the O—H stretch complex at about $3,380$ cm$^{-1}$; and (o) the ratio of the area of the proline band at about $856$ cm$^{-1}$ to the area of the hydroxyproline band at about $877$ cm$^{-1}$.

Typically, the absolute area of bands (a) to (j) is obtained.

Some or all of these bands can be seen as overlapping in the spectra. However, it is well known to the person skilled in the art that the bands can be subdivided into their constituent bands by using well established curve-fit routines including those in the GRAMS/AI© (ThermoGalactic) software, based on fitting band envelopes to Lorentzian or Gaussian curves. Thus persons with little or no clinical knowledge can be trained in the art of spectral analysis.

As shown in FIGS. 23 and 28, we have found that there is a statistically significant decrease in (m) the ratio of the mean area of the symmetric SO stretch of sulphate band at about $1,063$ cm$^{-1}$ to the mean area of the phenylalanine ring breathing band at about $1,003$ cm$^{-1}$, with increased levels of cartilage degradation and DJD.

As shown in FIGS. 24 and 29, we have found that there is a statistically significant increase in (k) the ratio of the mean area of the band due to H$_2$O bend at about $1,637$ cm$^{-1}$ to the mean area of the phenylalanine ring breathing band at about $1,003$ cm$^{-1}$, with increased levels of cartilage degradation and DJD.

As shown in FIGS. 25 and 30, we have found that there is a statistically significant increase in (l) the ratio of the mean area of the low-wavenumber band of the O—H stretch complex at about $3,210$ cm$^{-1}$ to the mean area of the CH stretch at about $2,940$ cm$^{-1}$, with increased levels of cartilage degradation and DJD.

As shown in FIGS. 26 and 31, we have found that there is a statistically significant increase in (n) the ratio of the mean area of the low-wavenumber band of the O—H stretch complex at about $3,210$ cm$^{-1}$ to the mean area of the high-wavenumber band of the O—H stretch complex at about $3,380$ cm$^{-1}$, with increased levels of cartilage degradation and DJD.

As shown in FIGS. 27 and 32, we have found that there is a statistically significant increase in (o) the ratio of the mean area of the proline band at about $856$ cm$^{-1}$ to the mean area of the hydroxyproline band at about $877$ cm$^{-1}$, with increased levels of cartilage degradation and DJD.

While it is preferred that the assessment of the level of degeneration of cartilage is performed by the analysis of the spectral parameter of one band relative to another, such as a ratio of band areas, it is possible to perform such assessments on the absolute value of a spectral parameter of a band, for instance, the absolute area of the phenylalanine ring breathing band at about $1,003$ cm$^{-1}$, the absolute area of the symmetric SO stretch of sulphate band at about $1,063$ cm$^{-1}$, the absolute area of the amide III band at about $1,272$ cm$^{-1}$, or the absolute area of the amide I band at about $1,665$ cm$^{-1}$ respectively, each of which is progressively decreased in cartilage from a joint with increased Grade DJD (data not shown). Of these assessments based on the absolute area the most preferred are those of (c) the phenylalanine ring breathing band at about 1,003 cm$^{-1}$, and (d) the symmetric SO stretch of sulphate band at about 1,063 cm cm$^{-1}$.

Thus, the analysing step typically comprises:
comparing any one, two, three, four, five, six, seven, eight or preferably all nine of:
(c) the area and position of a phenylalanine ring breathing band at about 1,003 cm$^{-1}$;
(d) the area and position of a symmetric SO stretch of sulphate band at about 1,063 cm$^{-1}$;
(e) the area and position of a band due to amide III at about 1,272 cm$^{-1}$;
(g) the area and position of a band due to amide I at about 1,665 cm$^{-1}$;
(k) the ratio of the area of the band due to H$_2$O bend at about 1,637 cm$^{-1}$ to the area of the phenylalanine ring breathing band at about 1,003 cm$^{-1}$;
(l) the ratio of the area of the low-wavenumber band of the O—H stretch complex at about 3,210 cm$^{-1}$ to the area of the CH stretch at about 2,940 cm$^{-1}$;
(m) the ratio of the area of the symmetric SO stretch of sulphate band at about 1,063 cm$^{-1}$ to the area of the phenylalanine ring breathing band at about 1,003 cm$^{-1}$;
(n) the ratio of the area of the low-wavenumber band of the O—H stretch complex at about 3,210 cm$^{-1}$ to the area of the high-wavenumber band of the O—H stretch complex at about 3,380 cm$^{-1}$; and
(o) the ratio of the area of the proline band at about 856 cm$^{-1}$ to the area of the hydroxyproline band at about 877 cm$^{-1}$.
from the test spectrum to the corresponding area, position or ratio from the standard spectrum.

Accordingly, the invention encompasses methods of assessing the degeneration of cartilage in a joint, of predicting the subsequent development of DJD in a joint, and of determining the presence or absence of features that are consistent with the patient having DJD in a joint, the method comprising:
obtaining a test spectrum of Raman scattered radiation from the cartilage tissue in the joint;
comparing any one, two, three, four, five, six, seven, eight or all nine of (c), (d), (e), (g), (k), (l), (m), (n) and (o) as defined above, from the test spectrum with the corresponding area, or ratio of areas from a standard spectra of Raman scattered radiation; and
assessing whether the patient has, or may subsequently develop, DJD in that joint.

Preferably, this assessment is based upon the significant correlation between a decrease in (c), (d), (e), (g) and (m), and an increase in (k), (l), (n) and (o), with DJD that we have identified.

Preferred combinations from those listed above are: (l) and (m); (d), (l) and (m); (l), (m) and (o); (d), (l), (m) and (o); (l), (m) and (n); (d), (l), (m) and (n); (o), (d), (l), (m) and (n).

We have also shown that it is possible to determine numerical 'indicator levels' for signs of degeneration for various parameters that could be used to indicate degeneration within a cartilage sample being analysed (see FIGS. 30 to 36, and Table 2). The indicator levels are typically determined based upon a comparison of spectral features obtained from populations of 'DJD' and 'non-DJD' control individuals, as defined above. Preferably, the indicator levels are derived from cartilage of the same species and of the same joint, as the patient being tested.

Accordingly, in an alternative preferred embodiment, the analysing step comprises comparing the area or height, or less preferably the width or position (mean wavenumber), of one or more bands from the test spectrum, or comparing the ratio of the area or height, or less preferably the width, of at least two bands from the test spectrum, with a predetermined indicator level, wherein the indicator level is indicative of the presence of DJD in the cartilage of the joint. Comparing the area or ratio of areas of bands from the test spectrum with a predetermined indicator level is preferred.

The ratio of the area of the following bands in the test spectrum can suitably be used in a comparison with indicator levels that are indicative of the presence of DJD in the cartilage of the joint:
(k) the ratio of band areas of the H$_2$O bend band at about 1,637 cm$^{-1}$ to the phenylalanine ring breathing band at about 1,003 cm$^{-1}$ (FIG. 29);
(l) the ratio of band areas of the low-wavenumber band of the O—H complex at about 3210 cm$^{-1}$ to the CH stretch band at about 2,940 cm$^{-1}$ (FIG. 30);
(m) the ratio of band areas of the symmetric SO stretch of sulphate band at about 1,063 cm$^{-1}$ to the phenylalanine ring breathing band at about 1,003 cm$^{-1}$ (FIG. 28);
(n) the ratio of band areas of the low-wavenumber band of the O—H complex at about 3,210 cm$^{-1}$ to the high-wavenumber band of the O—H complex at about 3380 cm$^{-1}$ (FIG. 31); and
(o) the ratio of band areas of the proline band at about 856 cm$^{-1}$ to the hydroxyproline band at about 877 cm$^{-1}$ (FIG. 32).

Thus the method includes:
obtaining, from a test spectrum of Raman scattered radiation from cartilage tissue in the joint; any one, two, three, four or all five of:
(k) the ratio of the area of the band due to H$_2$O bend at about 1,637 cm$^{-1}$ to the area of the phenylalanine ring breathing band at about 1,003 cm$^{-1}$;
(l) the ratio of the area of the low-wavenumber band of the O—H stretch complex at about 3,210 cm$^{-1}$ to the area of the CH stretch at about 2,940 cm$^{-1}$;
(m) the ratio of the area of the symmetric SO stretch of sulphate band at about 1,063 cm$^{-1}$ to the area of the phenylalanine ring breathing band at about 1,003 cm$^{-1}$;
(n) the ratio of the area of the low-wavenumber band of the O—H stretch complex at about 3,210 cm$^{-1}$ to the area of the high-wavenumber band of the O—H stretch complex at about 3,380 cm$^{-1}$; and
(o) the ratio of the area of the proline band at about 856 cm$^{-1}$ to the area of the hydroxyproline band at about 877 cm$^{-1}$,
and
analysing the one, two, three, four or five said ratios to assess whether the patient has, or will subsequently develop, DJD in the joint.

Typically, this analysis and assessment is based upon the significant correlation between a decrease in (m), and an increase in (k), (l), (n) and (o), with DJD, that we have identified.

In an embodiment, the analysing step comprises comparing a numerical ratio of the area of a pair of bands from the test spectrum with an indicator level which is indicative of the presence of DJD in the cartilage of the joint. More preferably, a plurality of ratios of the area of a corresponding plurality of pairs of bands from the test spectrum are compared with respective indicator levels which are indicative of the presence of DJD in the cartilage of the joint.

The ratios of the areas of the pairs of bands (k) to (o), as defined above, in the test spectrum can suitably be used in a comparison with indicator levels that are indicative of the presence of DJD in the cartilage of the joint.

Thus, the analysing step typically comprises:
comparing any one, two, three, four or preferably all five of:
(k) the ratio of the area of the band due to $H_2O$ bend at about 1,637 $cm^{-1}$ to the area of the phenylalanine ring breathing band at about 1,003 $cm^{-1}$;
(l) the ratio of the area of the low-wavenumber band of the O—H stretch complex at about 3,210 $cm^{-1}$ to the area of the CH stretch at about 2,940 $cm^{-1}$;
(m) the ratio of the area of the symmetric SO stretch of sulphate band at about 1,063 $cm^{-1}$ to the area of the phenylalanine ring breathing band at about 1,003 $cm^{-1}$;
(n) the ratio of the area of the low-wavenumber band of the O—H stretch complex at about 3,210 $cm^{-1}$ to the area of the high-wavenumber band of the O—H stretch complex at about 3,380 $cm^{-1}$; and
(o) the ratio of the area of the proline band at about 856 $cm^{-1}$ to the area of the hydroxyproline band at about 877 $cm^{-1}$.

from the test spectrum to a numerical 'indicator level' that is indicative of the presence or Grade of DJD in the cartilage of the joint.

Table 2 shows which side of the indicator levels indicates 'degeneration'. Specifically, ratios (k), (l), (n) and/or (o) lying above their respective indicator levels are indicative of degeneration, whereas ratio (m) lying below the indicator level is indicative of degeneration. Conversely, if the ratios fall on the other side of the respective indicator levels, this is indicative that the cartilage in the joint does not have DJD.

It is appreciated that a plurality of these indicator levels can be used in combination to distinguish between different Grades of cartilage degeneration. As discussed below with reference to Tables 2 and 3, it is not only possible to distinguish very clearly between Kellgren-Lawrence Grades 0 and I and Grades II and III, but also between Grade 0 and Grade I.

As shown in FIGS. 28 to 32 and Table 2, representative indicator levels that we have shown to be indicative of the presence or Grade of DJD in the cartilage of the human knee joint are:
a ratio of the area of the $H_2O$ bend band at about 1,637 $cm^{-1}$ to the area of the phenylalanine ring-breathing band at about 1,003 $cm^{-1}$ of >10;
a ratio of the area of the low-wavenumber band of the O—H complex at about 3,210 $cm^{-1}$ to the area of the CH stretch band at about 2,940 $cm^{-1}$ of >4;
a ratio of the area of the symmetric SO stretch of sulphate band at about 1,063 $cm^{-1}$ to the area of the phenylalanine ring-breathing band at about 1,003 $cm^{-1}$ of <1;
a ratio of the area of the low-wavenumber band of the O—H complex at about 3,210 $cm^{-1}$ to the area of the high-wavenumber band of the O—H complex at about 3,380 $cm^{-1}$ of >3.7; and
a ratio of the area of the proline band at about 856 $cm^{-1}$ to the area of the hydroxyproline band at about 877 $cm^{-1}$ of >1.5.

As shown in Tables 2 and 3, any one, but preferably, two, three or four, or more preferably all five of these ratios are compared with their respective indicator levels to assess the presence of DJD in the cartilage of the joint.

As discussed in more detail herein, it is appreciated that in an embodiment the method may further comprise obtaining and analysing Raman scattered radiation at a plurality of different locations of the cartilage tissue to provide a spatial assessment of the degenerative joint disease in the cartilage tissue.

It is appreciated that determining the area of other bands in Raman spectra may also be of value in assessing whether a patient has degenerative changes with their cartilage or an increased likelihood of developing DJD in a test joint. Accordingly, in an embodiment, the method further comprises determining and comparing the intensity of a carbonate, phosphate or $CH_2$ wag band in the test spectrum with the corresponding band in the standard spectra of Raman scattered radiation.

The method of the invention may be used to aid in distinguishing DJD from other conditions, such as rheumatoid arthritis, psoriatic arthritis and septic arthritis which display similar symptoms, and thus lead to a more reliable diagnosis of DJD. For example, the method may be used in conjunction with other tests such as X-ray analysis of the joint, magnetic resonance imaging of the joint, serum or urinary biomarkers, arthrocentesis or arthroscopy, or the observations by a physician, in reaching a diagnosis of DJD in a tested joint of a patient. Thus, the method of the invention may be used in combination with another technique to allow a physician make an accurate assessment of the level of degeneration of the joint cartilage, and an accurate diagnosis of DJD.

When the method of the invention is used to predict whether a patient has an increased likelihood of developing DJD, it is appreciated that the test may be performed on multiple occasions, particularly if the test is negative on the first occasion. For example, the test may be part of a routine medical examination and repeated at monthly, 2 monthly, 6 monthly, 1 yearly, 2 yearly, 3 yearly, 4 yearly or 5 yearly intervals.

When the method is used to predict whether a patient has an increased likelihood of developing DJD, it is also appreciated that the test may be performed at multiple points within that same joint to determine the position, Grade and/or extent of any lesion. Then at any subsequent test the change in position, Grade and/or extent of that lesion can be used to indicate progression of DJD, no change or an improvement in joint health.

Preferably, the patient is a mammal. The mammal may be any mammal, for example a human, a domesticated animal (for example a dog or cat), laboratory animal (for example laboratory rodent, mouse, rat or rabbit), an animal important in agriculture (e.g. livestock), for example, cattle, sheep, horses or goats, or an animal important in sport, for example, horses and dogs. It is particularly preferred if the mammal is any of a human, horse, dog or cat, most preferably a human.

A second aspect of the invention is a method of combating DJD in a joint of a patient the method comprising diagnosing DJD in a joint according to the method of the first aspect of the invention and treating the DJD.

Under existing treatment regimes for combating DJD, we include the meaning that the invention can be used to alleviate symptoms of the disorder (i.e. palliative use), or to treat the disorder.

In one embodiment, treating the DJD comprises administering at least one of paracetamol, aspirin, COX II inhibitors, injectable hyaluronic acid and a non-steroidal anti-inflammatory drug (NSAID) to the patient. These agents may be used in treating, or used in the manufacture of a medicament for treating, DJD in a joint of a patient who has been diagnosed as having DJD in that joint by a method according to the first aspect of the invention.

Preferences for the tested joint and for the mammal to be treated for this and subsequent aspects of the invention are as defined above with respect to the first aspect of the invention. For example, it is preferred if the joint is one which is commonly affected by DJD, and that the mammal to be treated is a human.

The invention also encompasses a method of combating DJD in a joint of a patient the method comprising predicting DJD in that joint according to a method of the first aspect of the invention, and preventing or delaying the onset of DJD, for example by the application of a treatment regime based upon diet, exercise or other lifestyle changes, or pharmaceutical intervention, or a combination thereof. In this context, by combating DJD, we include the meaning that the invention can be used to prevent DJD (i.e. prophylactic use) or to delay the symptoms of the disorder. Preferably the symptoms are delayed for at least 1, 2, 3, 4 or 5 years, more preferably for at least 10 years.

New approaches in the treatment of DJD, including new drug development, have been hindered by the lack of objective and measurable standards for disease progression by which such treatments can be evaluated (Takahashi et al, 2004). Current methods of evaluating disease progression, including radiographs and biochemical markers, are not accurate enough to be used in clinical trials of potential treatments. Generally, an interval of a year or two is needed to observe any significant change in radiographic grading, whereas only a few months or weeks may be sufficient to measure objectively degenerative changes in cartilage in the joint, both in terms of the level of degeneration and also the extent of any lesion or lesions within the joint.

The methods and apparatus of the present invention can advantageously be used for monitoring treatment efficacy in DJD. There is also a great potential in their use to help diagnose the disease at an earlier stage, assess the severity of the disease and monitor the effect of any treatment. It can be expected therefore that new treatments for DJD will be developed because it will be possible to measure their effects objectively at an early stage through the accurate, site-specific measurements of cartilage degeneration using the methods and apparatus of the present invention. Such treatments, if started early enough, could reverse any degenerative changes within the cartilage by such interventional pathways as: interrupting the catabolic pathways of cartilage possibly by interrupting directly or indirectly the degradative actions of matrix metalloproteinases (MMPs); by enhancing the anabolic pathways of cartilage possibly by enhancing the secretion of the extracellular matrix by the chondrocytes within the cartilage tissue; or by modifying both the anabolic and the catabolic pathways simultaneously in way that favours the laying down of new, healthy cartilage tissue, thus while increasing cartilage turnover the overall level of degeneration of the cartilage tissue is improved.

Furthermore, the methods and apparatus of the present invention are likely to allow more effective drug treatment of DJD, more appropriate timing of the treatment of DJD, better monitoring of the effect of the treatment of DJD and the development of new treatments, especially pharmaceutical treatments. It will also allow the timing and choice of surgery for the treatment of the symptoms of DJD to be improved We have identified measurable indicators of degeneration of cartilage of joints which may also be used to assess the efficacy of a treatment for DJD. Accordingly, a third aspect of the invention provides a method of assessing the efficacy of a treatment for DJD, the method comprising:

performing the method according to the first aspect of the invention;
administering a treatment for DJD;
repeating the method according to the first aspect of the invention subsequent to administering the treatment; and
assessing the efficacy of the treatment by comparing results of the method performed before and after the treatment.

It is appreciated that the test treatment may comprise the administration of a treatment agent, or the application of a treatment regime based upon, for example, diet, exercise or other lifestyle changes, or both. Treatment regimes could include medicaments that decrease cartilage catabolism, increase cartilage anabolism, or increases the overall level of turnover of cartilage but in a way that lays down new healthy tissue and thus reduce the level of degeneration of the cartilage.

Typically, this method of assessing the efficacy of a treatment for DJD, comprises:
obtaining a spectrum of Raman scattered radiation from a joint of a patient to provide a baseline spectrum;
administering a test treatment for DJD;
obtaining a spectrum of Raman scattered radiation emitted from the joint subsequent to the administration step; and
comparing the baseline spectrum with the subsequently obtained spectrum, thereby to assess the efficacy of the test treatment.

Preferably, the patient is one who has been diagnosed as having DJD in that joint, either by the method of the first aspect of the invention, or by any currently available methods for diagnosing DJD.

Typically, the comparison is performed on the regions of the spectrum that we have shown to be correlated with cartilage degeneration.

The method may be employed, for example, in the context of establishing whether a particular treatment is effective for a particular individual patient. Alternatively, the method may be employed, for example, in the context of a clinical trial of a test treatment for DJD. In this latter embodiment, the method is typically performed on a population of patients. Thus, for example, the method may be carried out on at least 50, 100, 200, 300, 400, 500 patients, or at least 1000 patients, or at least 5000 patients or more.

Accordingly, the method of assessing the efficacy of a treatment for DJD, may comprise:
obtaining a baseline spectrum of Raman scattered radiation from the cartilage of a joint in a population of patients;
administering a test treatment for DJD to the population of patients;
obtaining a spectrum of Raman scattered radiation emitted from the joint of the population of patients to subsequent to the administration step; and
comparing the mean baseline spectrum with the mean subsequently obtained spectrum, thereby to assess the efficacy of the test treatment.

As is well known in the art, to control for the 'placebo effect', it may be desirable to substitute the test treatment for a placebo in a proportion of the patients undergoing the clinical trial.

When the test treatment comprises the administration of a treatment agent, the agent may be administered as an individual dose or in several doses over a period of 1, 2, 4, 6, 6-12, 12-18 or 18-24 months, or several years, depending upon the treatment and route of administration.

Typically, the baseline spectrum of Raman scattered radiation is obtained immediately prior to the commencement of the test treatment or, for example, up to one or two months earlier.

The spectrum of Raman scattered radiation is typically obtained about 6 to 12 months after the commencement of the test treatment, and compared to the baseline measurement. Multiple spectra of Raman scattered radiation may be obtained at regular intervals, e.g. monthly, every six months, or every year, for several years in order to monitor efficacy of the treatment over time.

Typically, the step of comparing the Raman spectrum or spectra obtained subsequent to the treatment with the baseline measurement comprises comparing band areas or a ratio of band areas from the spectra as described above. Preferences for the band areas or ratio of areas to be obtained and compared are as defined above with respect to the first aspect of the invention.

Accordingly, in various embodiments, any combination of one, two, three, four, five, six, seven, eight or all nine of (c), (d), (e), (g), (k), (l), (m), (n) and (o) as defined above in the Raman spectrum or spectra obtained subsequent to the treatment are obtained and compared to the position, area and/or ratio of areas of the corresponding band(s) in the baseline spectrum.

Preferred combinations from those listed above are: (l) and (m); (d), (l) and (m); (l), (m) and (o); (d), (l), (m) and (o); (l), (m) and (n); (d), (l), (m) and (n); (o), (d), (l), (m) and (n).

We have shown that the position, area or ratio of areas of bands alter in cartilage with degenerative changes. Thus, an alteration in the at least one position, area or ratio of areas in the Raman spectrum obtained subsequent to the treatment relative to the baseline spectrum is an indication that the level of degeneration of cartilage in the joint has altered, either improving or deteriorating, since the baseline measurement, and hence the DJD is either progressing or is showing signs of improvement depending on what changes in the Raman spectrum was observed.

It is appreciated that a treatment may affect the rate of progression of DJD. Thus, it may be desirable to compare the change, or rate of change, in the at least one position, area or ratio of areas with the corresponding change in the position, area or ratio of areas in a Raman spectrum obtained from a patient administered a placebo treatment. From a comparison of the change or rate of change in the test treated joint with the corresponding change in the position, area or ratio of areas of the corresponding band(s) in the spectrum obtained from a placebo treated joint, the progression of DJD will be ascertained by comparison with the standard Raman spectra. In this way it is possible to ascertain if the disorder has progressed, if its progression has slowed, its progression has stopped or its progression has been reversed. It may also be desirable to compare the effects of a test treatment with an alternative, e.g. standard, treatment.

In a preferred embodiment, the assessment is based upon the significant correlation between a progressive decrease in (c), (d), (e), (g) and (m), and a progressive increase in (k), (l), (n) and (o), with increasing Grade of DJD that we have identified.

It is further appreciated that since the invention includes measuring indicators of DJD in joints, the invention may also be used to assess the efficacy of preventative agents for DJD. It is now well recognised that the development of such preventative agents has been severely hampered by the lack of suitable assessment technologies for early DJD when such preventative agents are at their most efficacious (Takahashi et al, 2004).

Accordingly, the invention also encompasses a method of assessing the efficacy of a preventative agent or regime for DJD, the method comprising:

obtaining a spectrum of Raman scattered radiation from the cartilage of a joint of a patient to provide a baseline measurement;

administering a test prophylactic treatment for DJD; and obtaining a spectrum of Raman scattered radiation emitted from the cartilage of the joint subsequent to the administration step, thereby to assess the efficacy of the preventative agent or regime in comparison with the baseline measurement taken prior to treatment.

It is appreciated that the test prophylactic treatment may comprise the administration of a preventative agent, or the application of a preventative treatment regime based upon, for example, diet, exercise or other lifestyle changes, or both. By preventative agent, we mean an agent which is capable of preventing or delaying the onset of DJD or clinical symptoms of osteoarthritis. By regime, we mean a lifestyle regime, which the patient may be put under to delay the onset of DJD or clinical symptoms of DJD.

Typically, the patient is one who is considered likely to develop DJD, determined either by using a method according to the invention, or due to the patient having one or more of risk factors for DJD including a family history of DJD, obesity, repeated trauma or surgery to joint structures, diabetes, gout, abnormal joints at birth and other growth hormone disorders The method may be employed, for example, in the context of establishing whether a particular preventative treatment is effective for a particular individual patient. Alternatively, the method may be employed, for example, in the context of a clinical trial of the test prophylactic treatment for osteoarthritis. In this latter embodiment, the method is typically performed on a population of patients. Thus, for example, the method may be carried out on at least 50, 100, 200, 300, 400, 500, or at least 1000 patients, or at least 5000 patients or more.

As is well known in the art, to control for the 'placebo effect', it may be desirable to substitute the test treatment for a placebo in a proportion of the patients undergoing the clinical trial.

When the test prophylactic treatment comprises the administration of a preventative treatment agent, the agent may be administered as an individual dose or in several doses over a period of 1, 2, 4, 6, 6-12, 12-18 or 18-24 months, or several years, depending upon the treatment and route of administration.

Typically, the baseline spectrum of Raman scattered radiation is obtained immediately prior to the commencement of the test prophylactic treatment or, for example, up to one or two months earlier.

The spectrum of Raman scattered radiation is typically obtained about 6 to 12 months after the commencement of the test prophylactic treatment, and compared to the baseline measurement. Multiple spectra of Raman scattered radiation may be obtained at regular intervals, e.g. monthly, every six months, or every year, for several years in order to monitor efficacy of the prevention over time.

Typically, the step of comparing the Raman spectrum or spectra obtained subsequent to the test prophylactic treatment with the baseline measurement comprises comparing band position, band area or a ratio of band areas from the spectra as described above.

Preferences for the band position, band areas or ratio of areas to be compared are as defined above with respect to the previous aspect of the invention.

We have shown that the position, area or ratio of areas of bands (a) to (o) alter with degenerative changes in cartilage. Thus, an alteration in the at least one position, area or ratio of areas in the Raman spectrum obtained subsequent to the test prophylactic treatment relative to the baseline spectrum is an indication that the level of degeneration of the cartilage in the joint has altered since the baseline measurement, and through comparisons with the standard Raman spectra, determine whether or not the cartilage has deteriorated, remained the same or improved.

It is appreciated that the test treatment may delay the onset of degenerative changes or of clinical symptoms of DJD. Thus, it may be desirable to compare the changes in at least one position, area or ratio of areas to the change in the position, area or ratio of areas of the corresponding band(s) in the spectrum obtained from the cartilage in a placebo treated joint. If the changes in the treated joint are less than the changes in the position, area or ratio of areas of the corresponding band(s) in the spectrum obtained from a placebo treated joint, the progression of DJD in the joint has been slowed, and the test treatment may be efficacious.

It is appreciated that the indicators of DJD that we have identified and described herein may also be considered to be indicators of the level of degeneration of the cartilage in the joint. Thus, these indicators may be used to assess the level of degeneration of cartilage in a joint. For example, the assessment of cartilage degeneration may constitute part of a medical examination and may have application in the sports industry, for example, in the football industry where players undergo stringent medical examinations prior to signing for a new club.

Accordingly, a fourth aspect of the invention includes a method of assessing the level of degeneration of cartilage in a joint of patient, comprising:

obtaining a test spectrum of Raman scattered radiation from the cartilage of a joint;

comparing the test spectrum, or one or more regions thereof, to a standard spectrum of Raman scattered radiation or to one of more respective regions thereof; and assessing the level of degeneration of the cartilage.

Preferences for the band positions, band areas or ratio of areas in the Raman spectra to be determined and compared are as defined above. Thus, the invention encompasses a method of assessing the quality of cartilage in a joint of a patient, comprising:

obtaining a test spectrum of Raman scattered radiation from the cartilage of a joint; and comparing any combination of one, two, three, four, five, six, seven, eight or all nine of (c), (d), (e), (g), (k), (l), (m), (n) and (o) as defined above from the test spectrum with the position, area and/or ratio of areas of the corresponding band(s) in a standard spectrum of Raman scattered radiation, thereby to generate an assessment of the quality of the cartilage.

In the context of this aspect of the invention, cartilage from a joint with DJD is considered to have high levels of degeneration. Thus, in cartilage with high degeneration, (c), (d), (e), (g), (k), (l), (m), (n) and (o) as defined above, are more closely related to the position, area or ratio of areas of the corresponding band(s) in the DJD standard spectra described above than they are to the non-DJD standard spectra described above.

Conversely, cartilage from a joint from a non-DJD is considered to have low levels of degeneration. Thus, in cartilage with low degeneration, (c), (d), (e), (g), (k), (l), (m), (n) and (o) as defined above are more closely related to the position and area or ratio of areas of the corresponding band(s) in the non-DJD standard spectra described above than they are to the DJD standard spectra described above.

It is appreciated that by comparing one or more regions of the test spectrum to one or more regions of a standard spectrum, we include comparing spectral features of the test spectrum to information derived from corresponding spectral features in one or more standard spectra. Thus, we include comparing one or more spectral features of the test spectrum to respective indicator levels derived from a comparison of the corresponding spectral features obtained from populations of 'degenerative' and 'non-degenerative' control cartilage, as defined herein. Preferably, the indicator levels are derived from cartilage of the same species and of the same joint, as the patient being tested.

The methods of this and all previous aspects of the invention may be performed on cartilage tissue in a joint in vivo. In one embodiment, the probe laser passed to the joint and the Raman scattered light is detected minimally-invasively through an incision in the skin of the patient at the site of the joint line of the joint being assessed. Preferably the light from the probe laser and the Raman scattered light area pass through the same incision. By detecting the Raman scattered light at a separate point from the probe laser (Matousek at 2005) and, by suitable mathematical manipulation, it is possible extract the Raman spectra of cartilage lying deep to the surface from the Raman spectrum of the superficial cartilage. When the cartilage thickness falls below a few millimeters, about 3 millimeters or less, or if a probe of greater power than used in the experiments described herein, the Raman spectrum of the underlying bone can appear as in FIG. 38, the Raman spectrum of this underlying bone can be extracted from the spectrum of the overlying cartilage by the same mathematical manipulation as described above. By knowing the point on the joint surface that is being measured, it possible to determine the shape and extent of a lesion as well as determining the amount of degeneration within the lesion and in this way build a 'map' of the joint surface in terms of degeneration. By comparing a map with that taken previously or in future it is possible to determine if the degeneration of the joint is deteriorating or improving.

Alternatively, if the region of the joint surface can be manipulated so that it lies within a few millimeters of the skin and with no bone tissue between the skin and the cartilage surface, all aspects of the invention can be performed on cartilage tissue in the joint in vivo transcutaneously by detecting the Raman scattered light at a separate point from the probe laser (Matousek at al 2005) and, by suitable mathematical manipulation, extract the cartilage Raman spectrum from the Raman spectrum of the overlying tissues.

Alternatively, but less preferably, the methods of this and all previous aspects of the invention may be performed on cartilage tissue in vitro, for example from a biopsy taken during arthroscopy, endoscopy or open surgery. The tissue sample, preferably but not limited to full thickness down to and including the underlying subchondral bone. The Raman spectra of the sample can then be measured using a variety of means such as but not limited to a Raman spectrometer system equipped for microbeam Raman spectroscopy (InVia Raman Microscope, Renishaw plc, UK). The power of the probe laser can be increased but limited by the denaturation temperature of the organic constituents of the tissue. Furthermore Raman spectra can be recorded at any of the surfaces of the biopsied sample including the bony surface. The wavelength of the probe laser can be varied for instance from infrared to X-ray wavelengths. The sample is preferably measured fresh but can be stored either refrigerated at about 4° C. or frozen at −18° C. or below. If frozen the sample must be completely defrosted before measurement begins, The cartilage should remain completely immersed during measurement. The immersion liquid could be water, deionised water, synovial fluid from the same individual or from another individual, or any other suitable medium. The Raman spectrum from the medium used will need to be measured and mathematically removed from the spectrum recorded from the excised tissue.

A fifth aspect of the invention provides an apparatus for diagnosing or predicting degenerative joint disease (DJD) in a joint of a patient, the apparatus comprising:
 a light source and transmitter;
 a detector configured to receive Raman scattered radiation from a portion of cartilage tissue in the joint illuminated by the light source;
 an analyser coupled to the detector and configured to obtain a test spectrum of the Raman scattered radiation and to analyse the test spectrum, or one or more regions thereof, to diagnose or predict DJD in the joint, according to the method of the first aspect of the invention.

This aspect of the invention includes apparatus for assessing the level of degeneration of cartilage in a joint of patient, the apparatus comprising:
 a light source and transmitter;
 a detector configured to receive Raman scattered radiation from a portion of cartilage tissue in the joint illuminated by the light source;
 an analyser coupled to the detector and configured to obtain a test spectrum of the Raman scattered radiation and to analyse the test spectrum, or one or more regions thereof, to assess the level of degeneration of the cartilage in the joint, according to the method of the fourth aspect of the invention.

It is appreciated that the analyser may comprise an optical processing unit 30, a spectral analyser 40 and a computer 50 as separate or combined components.

A schematic diagram of an exemplary apparatus is shown in FIG. 37, in which a light source 20 is connected via an optical link 60 to a transmitter/receiver unit 10, the detector of which is connected via a further optical link 70 to an optical processing unit 30. The optical transmitter/receiver unit 10 (i.e. an optical transceiver) is in communication with a portion of cartilage tissue 5. The optical processing unit 30 is connected a spectral analyser 40 and a computer 50. The computer 50 is configured to provide an indication of the presence of degenerative joint disease in the cartilage tissue 5 in accordance with the invention.

The transmitter/detector unit, or probe, may be a single unit possibly a single handheld Raman instrument, or may comprise a separate transmitter 100 and detector 110, as shown in FIG. 38, the remaining components of which are the same as in FIG. 39. The optical links 60, 70 are preferably fibre optic cables, which can be flexible. Once made suitably sterile, part or all of the probe 10 may be configured to be insertable in a surgical aperture, for example as in arthroscopic investigations.

Light emitting parts and light receiving parts of the probe may be arranged in various geometrical arrangements such as one or more circles of receiving elements around a central light emitting element, so that light can be received over a range of locations. The skilled person will recognise that, in Raman spectroscopy, spectra of sub-surface structures can be recorded if the light source and receiver are not coincident. More than one receiving element may also be used.

The spectral analyser 40 is typically configured to obtain any one, two, three, four, five, six, seven, eight, nine, ten, eleven, twelve, thirteen, fourteen or preferably all fifteen of: (a) the area and position of a proline band at about 856 $cm^{-1}$, (b) the area and position of a hydroxyproline band at about 877 $cm^{-1}$, (c) the area and position of a phenylalanine ring breathing band at about 1,003 $cm^{-1}$, (d) the area and position of a symmetric SO stretch of sulphate band at about 1,063 $cm^{-1}$, (e) the area and position of a band due to amide III at about 1,272 $cm^{-1}$, (f) the area and position of a band due to $H_2O$ bend at about 1,637 $cm^{-1}$, (g) the area and position of a band due to amide I at about 1,665 $cm^{-1}$, (h) the area and position of a CH stretch band at about 2,940 $cm^{-1}$, (i) the area and position of the low-wavenumber band of an O—H stretch complex at about 3,210 $cm^{-1}$, (j) the area and position of the high-wavenumber band of an O—H stretch complex at about 3,380 $cm^{-1}$, (k) the ratio of the area of the band due to $H_2O$ bend at about 1,637 $cm^{-1}$ to the area of the phenylalanine ring breathing band at about 1,003 $cm^{-1}$, (l) the ratio of the area of the low-wavenumber band of the O—H stretch complex at about 3,210 $cm^{-1}$ to the area of the CH stretch at about 2,940 $cm^{-1}$, (m) the ratio of the area of the symmetric SO stretch of sulphate band at about 1,063 $cm^{-1}$ to the area of the phenylalanine ring breathing band at about 1,003 $cm^{-1}$, (n) the ratio of the area of the low-wavenumber band of the O—H stretch complex at about 3,210 $cm^{-1}$ to the area of the high-wavenumber band of the O—H stretch complex at about 3,380 $cm^{-1}$, and (o) the ratio of the area of the proline band at about 856 $cm^{-1}$ to the area of the hydroxyproline band at about 877 $cm^{-1}$. Preferably, at least (k) to (o) are obtained.

The technique of Raman scattering spectroscopy relies on the scattering of an incident light beam that is generally monochromatic. Therefore, it is preferred if the light source 20 comprises a substantially monochromatic light source such as a laser. A laser provides a highly directional narrow beam of light that can be directed and focused by optical elements including mirrors, lenses, prisms etc. It can also be guided by light-directing optical elements including waveguides and optical fibres to deliver the incident light beam at specific points on or within a sample area that could be inside living tissue. These properties will be useful in different manifestations of the invention. Any of a variety of substantially monochromatic laser light sources can be used, including many that are commercially available. For example, the article "UV Resonance Raman measurements of poly-L-lysine's conformational energy landscapes: dependence on perchlorate concentration and temperature" by S. A. Asher et al (2007) describes using a 204 nm laser light source with a CCD detector. As a further example, the article by S. Kaminaka, et al (Journal of Raman Spectroscopy, vol. 33, pp. 498-502, 2002) describes using a 1064 nanometer wavelength light source with an InP/InGaAsP photodiode array.

Typically, the scattered light is collected, e.g. via a transmitting or reflective lens or though an optical fibre, and directed into a spectrometer, spectrograph or camera-based system that permits separation of the scattered light beam into its component wavelengths, allowing for detection of the relative positions and relative intensities of the different peaks corresponding to the characteristic vibrational modes within the sample. Wavelength separation may be achieved by the use of diffraction gratings, usually created or engraved using holographic techniques, and a monochromator or spectrograph system that employs multiple dispersion stages to achieve a high degree of resolution between the desired wavelengths and rejection of stray light signals from the incident laser. The radiation reflected from the gratings and dispersed into its component wavelengths is usually detected by a sensitive detector such as, but not limited to, an array of photosensitive diodes (a diode array detector) or a charge-coupled device (CCD).

Alternatively, a scanning spectrometer can be used, a slit in front of the detection device and scattered radiation dispersed into its component wavelengths being detected using a photomultiplier tube (PMT), usually in photon counting mode to improve the sensitivity. Such implementations of the technique may be useful, especially where an increased resolution between the wavelengths of the Raman scattered peaks in the inelastically scattered radiation is required.

The specific type of laser and excitation wavelength chosen can be influenced by the preferred embodiment of the invention. For studies of excised tissue mounted and examined in vitro, any laser wavelength can be used, typically with an excitation wavelength ranging from around 1,000 nm in the near-infrared region to around 200 nm in the ultraviolet region. A typical embodiment is one in which the exciting laser has a wavelength in the visible range of the spectrum provided by a gas-filled (argon, krypton, helium-neon, etc.) laser or a solid state diode laser. Alternative embodiments for excitation in the visible range include use of a solid state laser such as a $Nd^{3+}$:YAG or $Nd^{3+}$:YLF laser using appropriate optical devices to double the laser light frequency so that the emitted light appears in the visible range. In these usual embodiments of the technique the scattered light is analysed using a spectrometer or spectrograph system and the scattered light signal detected using a CCD or a diode array or a photomultiplier detector. This embodiment is readily practised on tissue samples mounted and examined in vitro. An embodiment applying ultraviolet excitation as the excitation source is developed using an ultraviolet laser such as a solid state diode laser or a gas laser such as an $Ar^+$ laser with appropriate optical devices to double the laser light frequency to produce wavelengths in the 250-200 nm range. Use of the shortest wavelengths in this range requires the use of specially fabricated or coated optical devices and elements such as lenses, mirrors, filters, prisms and dispersion gratings to transmit and reflect the ultraviolet light. The intensity of Raman scattered light increases as the fourth power of the inverse of the exciting light wavelength ($\lambda_{incident}^{-4}$) so the Raman effect is most intense using ultraviolet excitation. This can constitute an advantage for studying samples in vitro. However, using Raman spectroscopy for certain embodiments of the invention and in particular for studies in vivo is hampered by the strong absorption of the exciting and scattered beams by various molecular species within the tissue and also by the possibility of tissue damage by the ultraviolet excitation.

In a further embodiment, the exciting laser is chosen to have a wavelength in the near-infrared range as provided by a $Nd^{3+}$:YAG or $Nd^{3+}$:YLF laser or a solid state diode laser. The intensity of Raman scattered light diminishes with the fourth power of the exciting wavelength ($\lambda_{incident}^4$), so the Raman effect is weakest using near-infrared excitation. Typically the Raman scattered light from near-infrared excitation around 1,000 nm is analysed using interferometric techniques thus benefiting from the multiplex advantage of the interferometer and the resulting signal is transformed into a spectrum of scattered light intensity vs wavenumber ($cm^{-1}$) using fast Fourier transform (FFT) techniques analogous to those used in Fourier transform infrared (FTIR) spectroscopy. The resulting technique is known as Fourier transform Raman (FT-Raman) spectroscopy.

When using employing a FFT, the spectrum of Raman scattered radiation is directed into an interferometer rather than a spectrometer or spectrograph system. The scattered light beam that contains the entire spectrum of Raman scattered wavelengths is no longer separated spatially into its component wavelengths by a diffraction grating but instead is analysed using interferometric techniques using a Michelson interferometer or another interferometer design. The Michelson interferometer contains a beam-splitter that separates the beam of scattered light into two paths. One path is reflected from a static mirror and the second beam path is reflected from a moving mirror. The two light beams projected along each path are recombined at the beam-splitter according to a judicious arrangement of the reflected light pathways from the static and moving mirrors. The reflection of the incident light beam from the moving mirror induces a regular time-dependence in its signal of light intensity vs. time. Upon re-combination of the two reflected light beams (one from the static and one from the moving mirror) an interference pattern is generated that contains maxima and minima in its intensity as a function of the time during reflection of the light beam from the moving mirror, as a result of constructive and destructive addition or cancellation of waves between the two beams reflected from the two mirrors, as a function of their relative position or the path length travelled by the light wave between the beam-splitter and each mirror, that is therefore modulated by the time-dependent position of the moving mirror. The resulting interferogram then contains information on all of the scattered radiation wavelengths derived from the incident probe laser beam interaction with and inelastic or Raman scattering by the sample. The resulting interferogram is then compared with a standard interferogram obtained under similar conditions when no sample is present. The two (sample vs. standard) interferograms are usually divided or their logarithms are subtracted to provide a Raman spectrum of the sample itself. The resulting spectrum of Raman scattered intensity vs. the time variable used to complete each interferometer cycle is usually transformed into a scale of intensity vs. light frequency using a mathematical FTT. In an embodiment, data collection and analysis techniques include FFT methods that can be implemented using laboratory scale and commercially available computer systems. The implementation of such methodology using incident probe laser wavelengths in the near-infrared region for biochemical and biophysical studies related to bone and cartilage investigations and assessment has been described (e.g., Lambert et al, 2006).

Raman spectroscopy using shorter near-infrared excitation wavelengths at around 700-850 nm is usually practised using a spectrograph or spectrometer system using CCD or diode array detectors to detect the scattered radiation.

In general, near-infrared wavelengths provide better depth of penetration into tissue. On the other hand, as wavelengths increase, they begin to fall outside the response range of silicon photo detectors (which have much better signal-to-noise ratios than other currently available detectors). One example of a light source that can be used is the widely available 785 nanometer diode laser. This wavelength can penetrate at least 1 to 2 millimeters into tissue. Additionally, this wavelength is not absorbed by blood haemoglobin and is only weakly absorbed by melanin and it is below the infra-red wavelengths that are strongly absorbed by water.

If the cartilage tissue is to be exposed by incision, or if biopsied cartilage tissue is to be examined, other wavelengths may be employed. For example, an 830 nanometer diode laser could be used with the laser power set at 100%, which at the sample delivers typically 15 milliwatts. Many other wavelengths may be used as well. In general, a wavelength of a light source may be chosen based on various factors including one or more of a desired depth of penetration, availability of photo detectors capable of detecting light at and near the wavelength, efficiency of photo detectors, cost, manufacturability, lifetime, stability, scattering efficiency, penetration depth, and so on. It is particularly preferred if the light source produces light having a wavelength between 785 nanometers and 850 nanometers.

Any of a variety of substantially monochromatic light sources can be used, including commercially available light sources. For example, Kaminaka et al (2002) describes using a 1064 nanometer wavelength light source with an InP/InGaAsP detector.

It is appreciated that the light source (10) may be optically coupled to at least one optical fibre that is optically coupled to an optical probe, as discussed below. The optical probe is capable of being positioned close to a portion of cartilage tissue from a patient, and may be used to irradiate the cartilage tissue with the light generated by the light source.

The radiation transmitter/receiver 10 (FIG. 37) may comprise a microscope, an optical probe or a lens coupled to a needle as described in US 2007/0049808.

A number of optical probes are commercially available. For instance, the Handbook of Vibrational Spectroscopy, Volume 2: Sampling Techniques, 1587-1597 (J. Chalmers et al, eds., John Wiley & Sons Ltd. 2002) describes examples of fibre optic probes that can be used. It is preferred if optical probes designed for Raman spectrometry are used. For example, any of a variety of commercially available fibre optic probes can be used. Some commercially available fibre optic probes include filters to reject Raman scatter generated within the excitation fibre and/or to attenuate laser light entering the collection fibre or fibres. Loosely focused light may help eliminate or minimise patient discomfort as compared to tightly focused light. As is known to those of ordinary skill in the art, loosely focused light may be achieved by a variety of techniques including multimode delivery fibres and a long focal length excitation/collection lens(es).

Existing commercially available fibre optic probes may be modified, or new probes developed, to maximize collection efficiency of light originating at depths of 1 millimeter or more below the surface of a highly scattering medium, such as cartilage tissue. Such modified, or newly developed probes, may offer better signal-to-noise ratios and/or faster data collection and better assessment of the depth of any degeneration of the cartilage tissue. The probe may be modified or may be coupled to another device to help maintain a constant probe-to-tissue distance, which may help to keep the system in focus and help maximize the collected signal.

It will be recognised that when the light source is optically coupled to an optical probe by means of an optical fibre, the optical probe may further be optically coupled to at least one other optical fibre that is used to collect Raman scattered radiation from the cartilage tissue but not necessarily from the same point as the point of illumination. Alternatively, a separate optical probe, optically coupled to a further optical fibre may be positioned close to the portion of cartilage tissue to collect Raman scattered radiation transmitted from the tissue but not necessarily from the same point as the point of illumination.

Relay optics may also be coupled to, or incorporated in, a needle, lending it particularly well to when the cartilage tissue is irradiated via an incision (and/or the radiation is to be collected via an incision). For example, two optical fibres or an "n-around-one" array could be used. In general, the size and the number of fibres should be appropriate to fit into a needle. The diameter of the excitation/collection lens or lenses used in such an embodiment could be small to help minimise the size of the incision. For example, lenses of diameters between 0.3 and 1 millimeter could be used. Lenses having larger or smaller diameters could be used as well. The lens(es) and or optical fibres could be incorporated into a hypodermic needle such as a No. 12 French type needle.

Additionally, a microprobe or microscope may be used instead of an optical probe, e.g. a confocal microscope such as the inVia Raman Microscope (Renishaw plc, UK) may be used.

Preferably the radiation received from the detector is processed by an optical processor 30, some or all of which may be part of the spectral analyser 40. For example, the optical processor 30 may include one or more lenses for focusing the collected light. The optical processor may also include one or more filters to attenuate laser light.

The spectral analyser 40 may comprise a spectrograph optically coupled with a photo detector array. The photo detector array may comprise a charge coupled device, or some other photo detection device. For example, Kaminaka et al (2002) describes using a 1,064 nanometer wavelength light source with an InP/InGaAsP photodiodes. Alternatively, the spectral analyser may comprise one or more filters to isolate a plurality of wavelengths of interest. Then, one or more photo detectors (e.g., a CCD, an avalanche photodiode, photomultiplier tube, etc.) could be optically coupled to the output of each filter. A single detector could be used with a tunable filter (e.g., an interferometer, liquid crystal tunable filter, acousto-optic tunable filter, etc.) or if fixed passband filters (e.g., dielectric filters, holographic filters, etc.) are placed in front of the detector one at a time using, for example, a slider, filter wheel, etc. In general, any of a variety of spectral analysers could be used such as a Raman analyser, an interferometer, etc. Additionally the light source (20), the optical processor (30) and the spectral analyser (40) can be combined into a single hand-held device, similar to those already commercially available for instance from Ahura Scientific, USA.

The computer 50 may comprise, for example a desktop computer, a laptop computer, a tablet PC, a personal digital assistant, a workstation, a server, a mainframe, and so on. The computer may be communicatively coupled to the spectral analyser 40 via a wired connection (e.g., wires, a cable, a wired local area network (LAN), etc.) or a wireless connection (a BLUETOOTH™ link, a wireless LAN, an IR link, etc.). In some embodiments, the spectral content information generated by the spectral analyser may be stored on a disk (e.g., a floppy disk, a compact disk (CD), etc.), and then transferred to the computing device via the disk. Although the spectral analyser 40 and the computer 50 are illustrated in FIG. 37 as separate devices, in some embodiments the spectral analyser 40 and the computer 50 may be part of a single device. The light source 20 and radiation transceiver 10 may be comprised in separate units or preferably as part of a single unit such as an arthroscope.

Raman spectral analysis is typically performed using a commercial software package (e.g. OriginPro7, OriginLab Corp, USA) installed in the computing device. A suitable processing routine in OriginPro7 is as follows. Any spikes due to cosmic rays or known background light are removed and for cartilage with high levels of degeneration the spectrum maybe best smoothed using adjacent averaging over several points, typically 5 or more. Background fluorescence and known systematic errors of measurement may be removed using the 'baseline' or other tools and the Lorentzian curve fitting tool used to analyse each band and, if appropriate, its sub-bands. In this way the area, position, width and height are calculated.

Previously determined standard spectra of Raman scattered radiation, or information derived therefrom, such as indicator level of cartilage degeneration, may be entered via a user input device, loaded from a disk or received via a network and may be stored in one or more of the computer's memories or storage systems.

It is appreciated that the computer 50 will preferably compare the test spectrum of Raman scattered radiation to the standard Raman spectra either in the form of a direct comparison of the whole spectrum and/or individual sections thereof, or comparison will be made of the analysed summary of the position, area, height and width of the bands. Typically, the computer 50 is configured to compare the position, area or ratio of areas of any of (a) to (o) as defined above to the corresponding band(s) or ratios in the standard spectra of Raman scattered radiation. In particular, comparison can be made of any one, two, three, four, five, six, seven, eight or preferably all nine of:

(c) the area and position of a phenylalanine ring breathing band at about 1,003 $cm^{-1}$;

(d) the area and position of the symmetric SO stretch of sulphate band at about 1,063 $cm^{-1}$;

(e) the area and position of a band due to amide III at about 1,272 $cm^{-1}$;

(g) the area and position of a band due to amide I at about 1,665 $cm^{-1}$;

(k) the ratio of the area of the band due to $H_2O$ bend at about 1,637 $cm^{-1}$ to the area of the phenylalanine ring breathing band at about 1,003 $cm^{-1}$;

(l) the ratio of the area of the low-wavenumber band of the O—H stretch complex at about 3,210 $cm^{-1}$ to the area of the CH stretch band at about 2,940 $cm^{-1}$;

(m) the ratio of the area of the symmetric SO stretch of sulphate band at about 1,063 $cm^{-1}$ to the area of the phenylalanine ring breathing band at about 1,003 $cm^{-1}$;

(n) the ratio of the area of the low-wavenumber band of the O—H stretch complex at about 3210 $cm^{-1}$ to the area of the high-wavenumber band of the O—H stretch complex at about 3380 $cm^{-1}$; and (o) the ratio of the area of the proline band at about 856 $cm^{-1}$ to the area of the hydroxyproline band at about 877 $cm^{-1}$.

from the test spectrum with the corresponding area, position, height or width or ratio from a standard spectrum.

Typically, the computer is configured to compare any combination of one, two, three, four, five, six, seven, eight or preferably all nine of (c), (d), (e), (g), (k), (l), (m), (n) and (o) in the test spectrum to the position, area or ratio of areas of the corresponding band(s) in the standard spectra of Raman scattered radiation. Thus, the computing device may be configured to compare various combinations of the above to the intensity and/or ratio of intensities of the corresponding band(s) in the standard spectrum. Other useful comparisons of test and standard spectra are discussed above with respect to the first aspect of the invention.

The standard spectra may be any of the "non-DJD" and/or "DJD" standard spectra described above with respect to the first aspect of the invention. It will be appreciated that the computer may be configured with criteria under which the comparison is made. For example, the computer may be configured to compare the position, area of the bands or ratio of areas to the mean position, area or ratio of areas of the corresponding band(s) in the standard spectra, determine to which standard spectra the test spectra is closest and thereby determine the level of degeneration if any. The computer may also be configured to conduct any number of statistical tests, as described above, and which are well known in the art.

Additionally or alternatively, the computer will preferably be configured to compare processed information relating the ratio of areas of any one, two, three, four or preferably all five of the following bands in the test spectrum with numerical indicator levels that are indicative of the presence of DJD in the cartilage of the joint:

(k) the ratio of the area of the band due to $H_2O$ bend at about 1,637 $cm^{-1}$ to the area of the phenylalanine ring breathing band at about 1,003 $cm^{-1}$;

(l) the ratio of the area of the low-wavenumber band of the O—H stretch complex at about 3,210 $cm^{-1}$ to the area of the CH stretch at about 2,940 $cm^{-1}$;

(m) the ratio of the area of the symmetric SO stretch of sulphate band at about 1,063 $cm^{-1}$ to the area of the phenylalanine ring breathing band at about 1,003 $cm^{-1}$;

(n) the ratio of the area of the low-wavenumber band of the O—H stretch complex at about 3,210 $cm^{-1}$ to the area of the high-wavenumber band of the O—H stretch complex at about 3,380 $cm^{-1}$; and (o) the ratio of the area of the proline band at about 856 $cm^{-1}$ to the area of the hydroxyproline band at about 877 $cm^{-1}$.

The representative indicator levels that we have shown to be indicative of the presence of DJD in the cartilage of the human knee joint are:

a ratio of the area of the band due to $H_2O$ bend at about 1,637 $cm^{-1}$ to the area of the phenylalanine ring breathing band at about 1,003 $cm^{-1}$ of >10;

a ratio of the area of the low-wavenumber band of the O—H stretch complex at about 3,210 $cm^{-1}$ to the area of the CH stretch at about 2,940 $cm^{-1}$ of >4;

a ratio of the area of the symmetric SO stretch of sulphate band at about 1,063 $cm^{-1}$ to the area of the phenylalanine ring breathing band at about 1,003 $cm^{-1}$ of <1;

a ratio of the area of the low-wavenumber band of the O—H stretch complex at about 3,210 $cm^{-1}$ to the area of the high-wavenumber band of the O—H stretch complex at about 3,380 $cm^{-1}$ of >3.7; and a ratio of the area of the proline band at about 856 $cm^{-1}$ to the area of the hydroxyproline band at about 877 $cm^{-1}$ of >1.5.

In an embodiment, the computing device is configured to produce a read-out based on the comparison between the test and standard spectra of Raman scattered radiation, and/or the comparison between processed information relating to bands in the test spectrum and known indicator levels, to indicate factors such as cartilage quality, whether or not the joint shows signs of DJD, the stage of cartilage degeneration, and/or the likelihood of the development of DJD in that joint.

It should be noted that these measurements do not pertain to the whole joint but to the point on the sample that is being illuminated, which is typically a few tens of microns in diameter. This means that accurate mapping of levels of degeneration across the joint surface are possible.

When performing measurements on cartilage tissue, either in vivo or in vitro, techniques may be employed to enable mapping of the tissue by taking repeated measurements at different locations on the tissue. For example, a region of cartilage of a patient may be analysed in detail by enabling an arthroscope with positional feedback so that measurements can be taken at different locations and built up into a spatial assessment, or map, of the cartilage surface. Such a spatial assessment may be particularly beneficial, for example, when assessing a joint with late stage DJD as this will allow an accurate assessment of suitable implants. A schematic representation of a system is shown in FIG. 39.

A position indicator 200 is connected to the transceiver 10, the position being determined by means of a position sensor 210, which is in coordination with the position indicator 200. Using the system as shown in FIG. 39, a map may be built up as a surgeon carries out the measurements. This has the advantage of being able to record spectra at specific locations, e.g. across the surface of a joint, and linking the spectra to the locations. Regions of the cartilage may then be identified for further analysis or treatment, or a more accurate determination made of the overall state of the tissue by taking an average reading from a series of measurements at different locations of the cartilage.

At least two well-established technologies may be applied to obtain a position sensing system to enable mapping of cartilage. Optical sensing can be used, in which the position indicator 200 is a series of markers, normally retro-reflective, that can be detected and triangulated by a series of cameras (e.g. infrared cameras with infrared light sources) to give the position and orientation of the position sensor 200. Electromagnetic sensing, which can take many forms, may alternatively be used, for example in which a known magnetic field is created in the surgical area and the position indicator 200 is able to detect the magnetic field strength and direction (e.g. by means of a Hall probe), from which can be calculated the position and orientation of the position indicator 200.

it is appreciated that the method according to the invention can be carried out independently from, or in conjunction with, the step of illuminating the cartilage tissue and receiving Raman scattered radiation from the tissue. Test spectra may be obtained from measurements that have been previously taken and then analysed according to the various methods detailed herein. Analysis may not therefore necessarily take place at the same time, or the same location, as the step of generating a test spectrum by illuminating a tissue sample.

Accordingly, a sixth aspect of the invention includes a computer program for instructing a computer to perform the method of the first or fourth aspects of the invention, particularly the data analysis and comparison steps thereof. The invention also includes a computer readable medium comprising a computer program for instructing a computer to perform the data analysis and comparison steps of the method of the first or fourth aspects of the invention. The invention also includes a computing device that has been programmed to perform the data analysis and comparison steps of the method of the first or fourth aspect of the invention.

FIG. 40 is a simplified flow diagram of a method 340 according to an embodiment of the invention. At step 300 the cartilage tissue is irradiated with light, causing Raman scattered radiation to be emitted, which is collected at step 310 from the tissue. The spectrum of the scattered radiation is then determined at step 320, and the spectrum assessed at step 330 to determine signs of degradation in the cartilage.

FIG. 41 illustrates a series of method steps 440 associated with a particular embodiment of the invention, in which a ratio is used to determine cartilage degradation by comparing a ratio with an indicator level for that ratio. The areas of the low-wavenumber band of the O—H stretch complex at about 3,210 $cm^{-1}$ and the CH stretch band at about 2,940 $cm^{-1}$ are determined at steps 400 and 410, for example by curve-fitting techniques described above. A ratio of the areas is then determined at step 420. This ratio is used, at step 430, to assess signs of cartilage degeneration by comparing the ratio with a standard indicator for that ratio.

FIG. 42 illustrates a series 540 of method steps associated with a further particular embodiment of the invention, in which a ratio is used to determine cartilage degradation by comparing a ratio with an indicator level for that ratio. The areas of the low-wavenumber band of the O—H stretch complex at about 3,210 $cm^{-1}$ and the high-wavenumber band of the O—H stretch complex at about 3,380 $cm^{-1}$ are determined at steps 500 and 510, for example by curve-fitting techniques described above. A ratio of the areas is then determined at step 520. This ratio is used, at step 530, to assess signs of cartilage degeneration by comparing the ratio with a standard indicator for that ratio.

FIG. 43 illustrates a series 640 of method steps associated with a further particular embodiment of the invention, in which a ratio is used to determine cartilage degradation by comparing a ratio with an indicator level for that ratio. The areas of the symmetric SO stretch of sulphate band at about 1,063 $cm^{-1}$ and the phenylalanine ring breathing band at about 1,003 $cm^{-1}$ are determined at steps 600 and 610, for example by curve-fitting techniques as described above. A ratio of the areas is then determined at step 620. This ratio is used, at step 630, to assess signs of cartilage degeneration by comparing the ratio with a standard indicator for that ratio.

FIG. 44 illustrates a series 740 of method steps associated with a further particular embodiment of the invention, in which a ratio is used to determine cartilage degradation by comparing a ratio with an indicator level for that ratio. The areas of the proline band at about 856 $cm^{-1}$ and the hydroxyproline band at about 877 $cm^{-1}$ are determined at steps 700 and 710, for example by curve-fitting techniques described above. A ratio of the areas is then determined at step 720. This ratio is used, at step 730, to assess signs of cartilage degeneration by comparing the ratio with a standard indicator for that ratio.

All of the documents referred to herein are incorporated herein, in their entirety, by reference.

The invention will now be described in more detail by way of example and with reference to the following Figures.

FIG. 1 shows a typical spectrum of Raman scattered photons before removal of the fluorescence background signal, the spectrum recorded from the surface of a full thickness cartilage sample taken from the knee with no signs of joint degeneration. The so-called "fingerprint" region extends from about 400 $cm^{-1}$ to about 1,800 $cm^{-1}$ and is marked as such.

FIG. 2 shows typical Raman spectra of cartilage of different levels of degeneration, showing the so-called "fingerprint" region and important spectral features that lie outside this region. Spectrum A is a typical spectrum of Grade 0 cartilage, spectrum B a typical spectrum of Grade I cartilage, spectrum C a typical spectrum of Grade II cartilage, and spectrum D a typical spectrum of Grade III cartilage. Grade 0 indicates healthy full thickness cartilage from a joint with no signs of degeneration. Grade I indicates full thickness cartilage from a joint with a distinct degenerative lesion elsewhere in the joint than the point of harvest. Grade II indicates tissue from the edge of a distinct degenerative lesion at a point where there were early signs of degeneration. Grade III indicates tissue from the centre or around the centre of a distinct cartilage at a point where there are signs of deep erosion and high levels of degeneration.

FIG. 3 shows typical Raman spectra of cartilage of different levels of degeneration from the range 800 $cm^{-1}$ to 1,120 $cm^{-1}$. Spectrum A is a typical spectrum of Grade 0 cartilage, spectrum B a typical spectrum of Grade I cartilage, spectrum C a typical spectrum of Grade II cartilage, and spectrum D a typical spectrum of Grade III cartilage. One of the most important bands, that of the symmetric SO stretch of sulphate band at about 1,063 $cm^{-1}$, is shown in bold.

FIG. 4 shows typical Raman spectra of cartilage of different levels of degeneration from the range 1,215 $cm^{-1}$ to 1,500 $cm^{-1}$. Spectrum A is a typical spectrum of Grade 0 cartilage, spectrum B a typical spectrum of Grade I cartilage, spectrum C a typical spectrum of Grade II cartilage, and spectrum D a typical spectrum of Grade III cartilage.

FIG. 5 shows typical Raman spectra of cartilage of different levels of degeneration from the range 1,465 $cm^{-1}$ to 1,740 $cm^{-1}$. Spectrum A is a typical spectrum of Grade 0 cartilage, spectrum B a typical spectrum of Grade I cartilage, spectrum C a typical spectrum of Grade II cartilage, and spectrum D a typical spectrum of Grade III cartilage. One of the most important bands the $H_2O$ bend band at about 1,637 $cm^{-1}$ is shown in bold.

Figure 23:
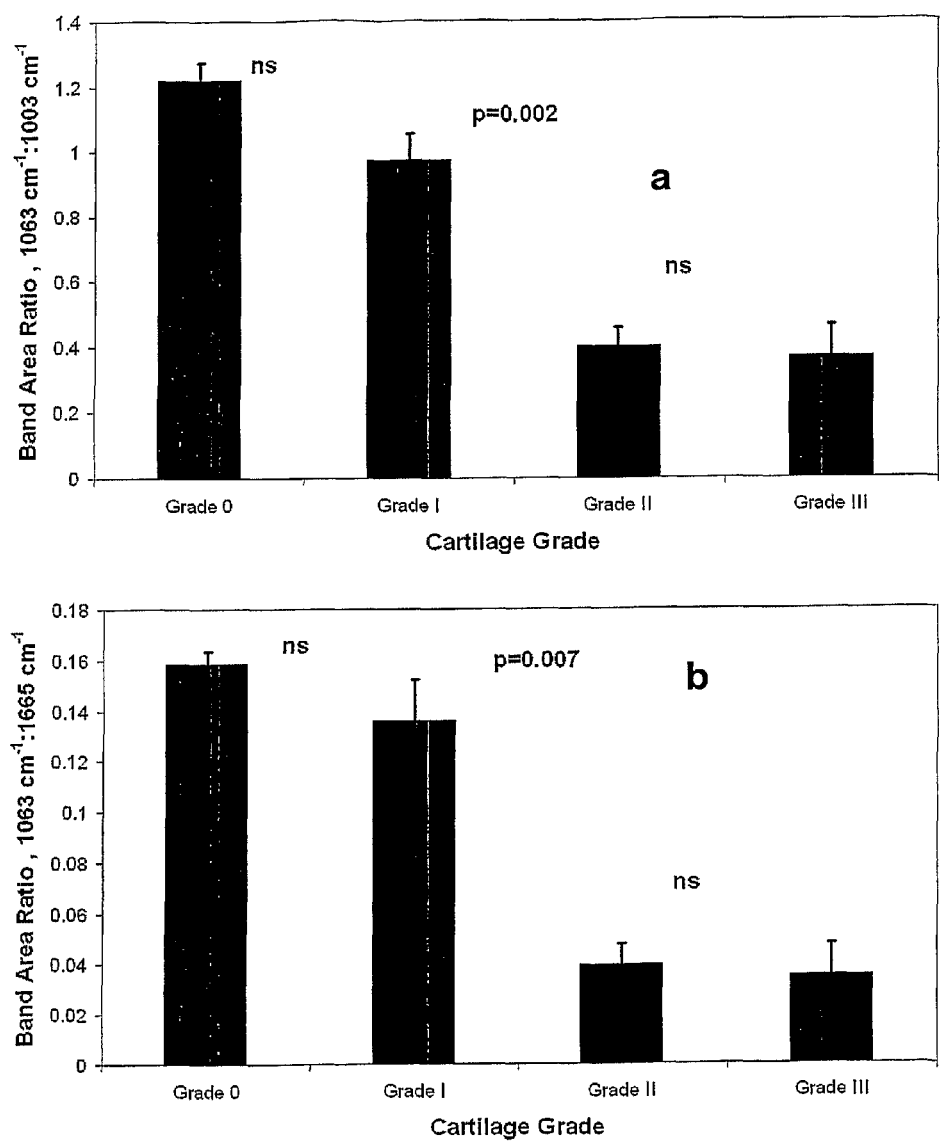

FIGS. 23a and 23b show bar charts illustrating the changes in mean ratio of the band areas of the symmetric SO stretch of sulphate band at about 1,063 $cm^{-1}$ to that of the phenylalanine ring breathing band at about 1,003 $cm^{-1}$ with cartilage grade. FIG. 23a shows the mean band area for all four Grades individually. FIG. 23b shows the mean band area for Grades 0 and I combined and Grades II and III combined. The error bars indicate the standard error for the mean and the p values indicate the significance of the difference in the mean band area between the two groups immediately below the stated value, with 'ns' indicating no significance.

Figure 24:
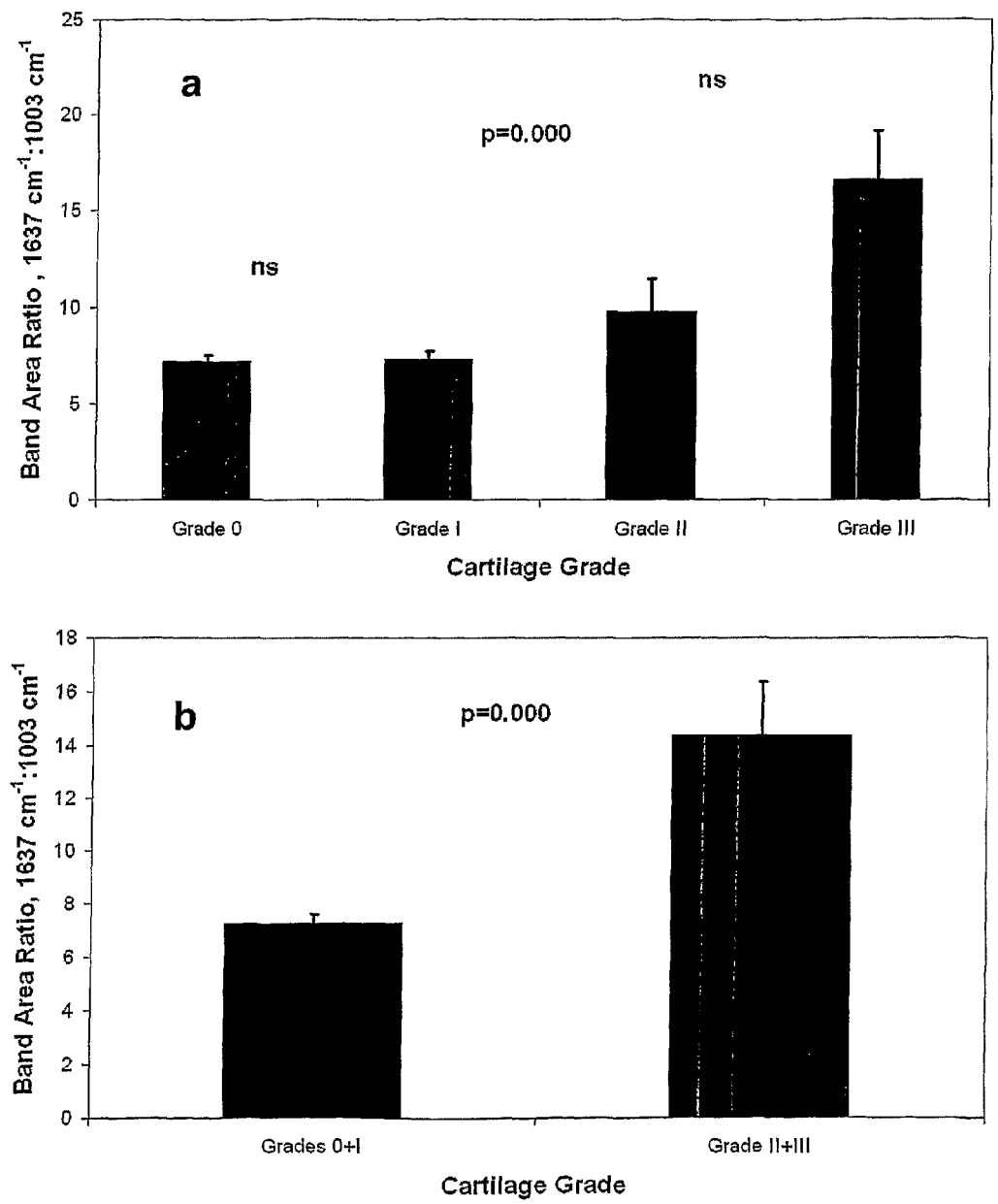

FIGS. 24a and 24b show bar charts illustrating the changes in mean ratio of the band areas of the $H_2O$ bend band at about 1,637 $cm^{-1}$ to that of the phenylalanine ring breathing band at about 1,003 $cm^{-1}$ with cartilage grade. FIG. 23a shows the mean band area for all four Grades individually. FIG. 23b shows the mean band area for Grades 0 and I combined and Grades II and III combined. The error bars indicate the standard error for the mean and the p values indicate the significance of the difference in the mean band area between the two groups immediately below the stated value, with 'ns' indicating no significance.

Figure 25:
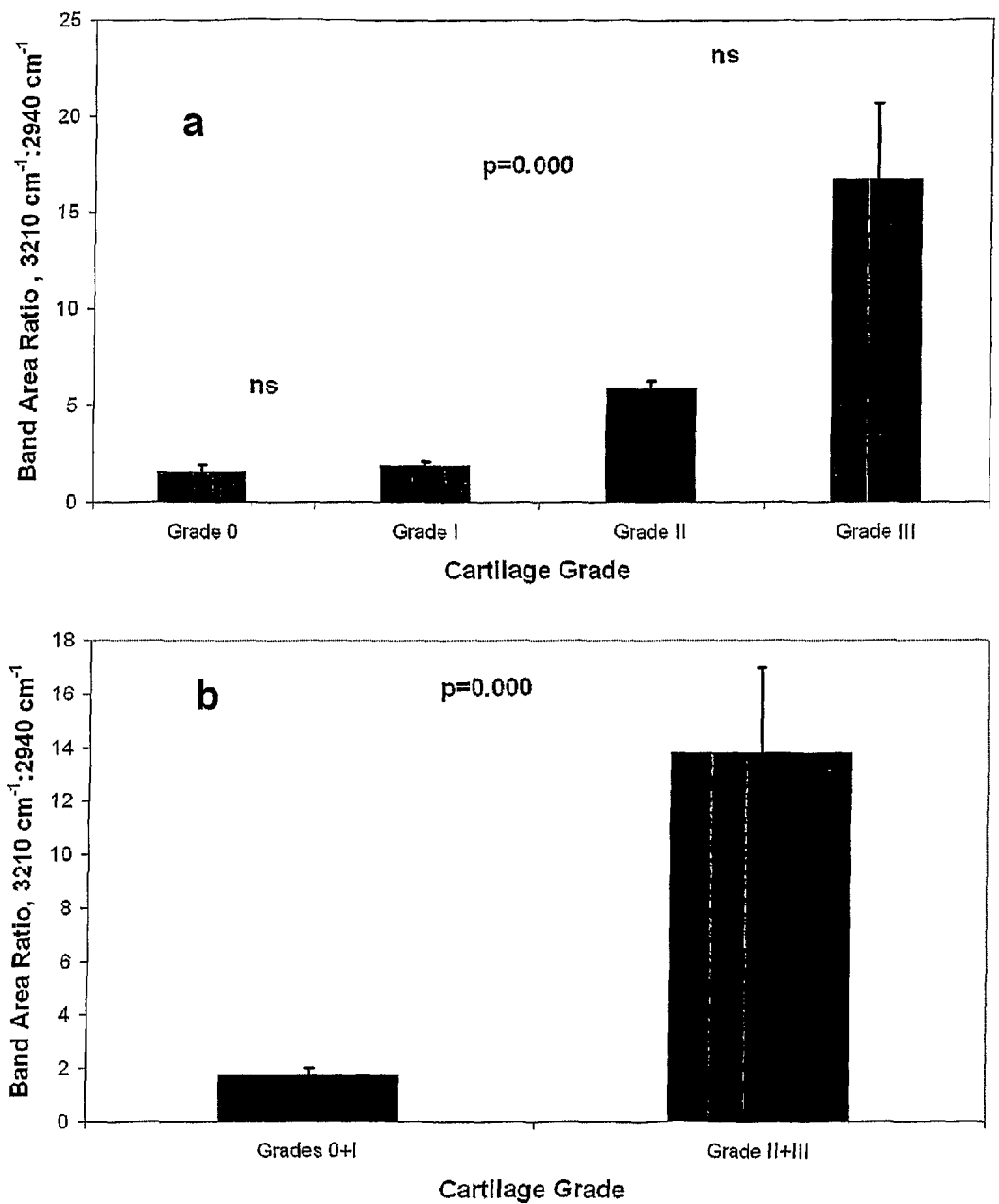

FIGS. 25a and 25b show bar charts illustrating the changes in mean ratio of the band areas of the low-wavenumber band of the O—H complex at about 3,210 $cm^{-1}$ to that of the CH stretch band at about 2,940 $cm^{-1}$ with cartilage grade. FIG. 25a shows the mean band area for all four Grades individually. FIG. 25b shows the mean band area for Grades 0 and I combined and Grades II and III combined. The error bars indicate the standard error for the mean and the p values indicate the significance of the difference in the mean band area between the two groups immediately below the stated value, with 'ns' indicating no significance.

Figure 26:
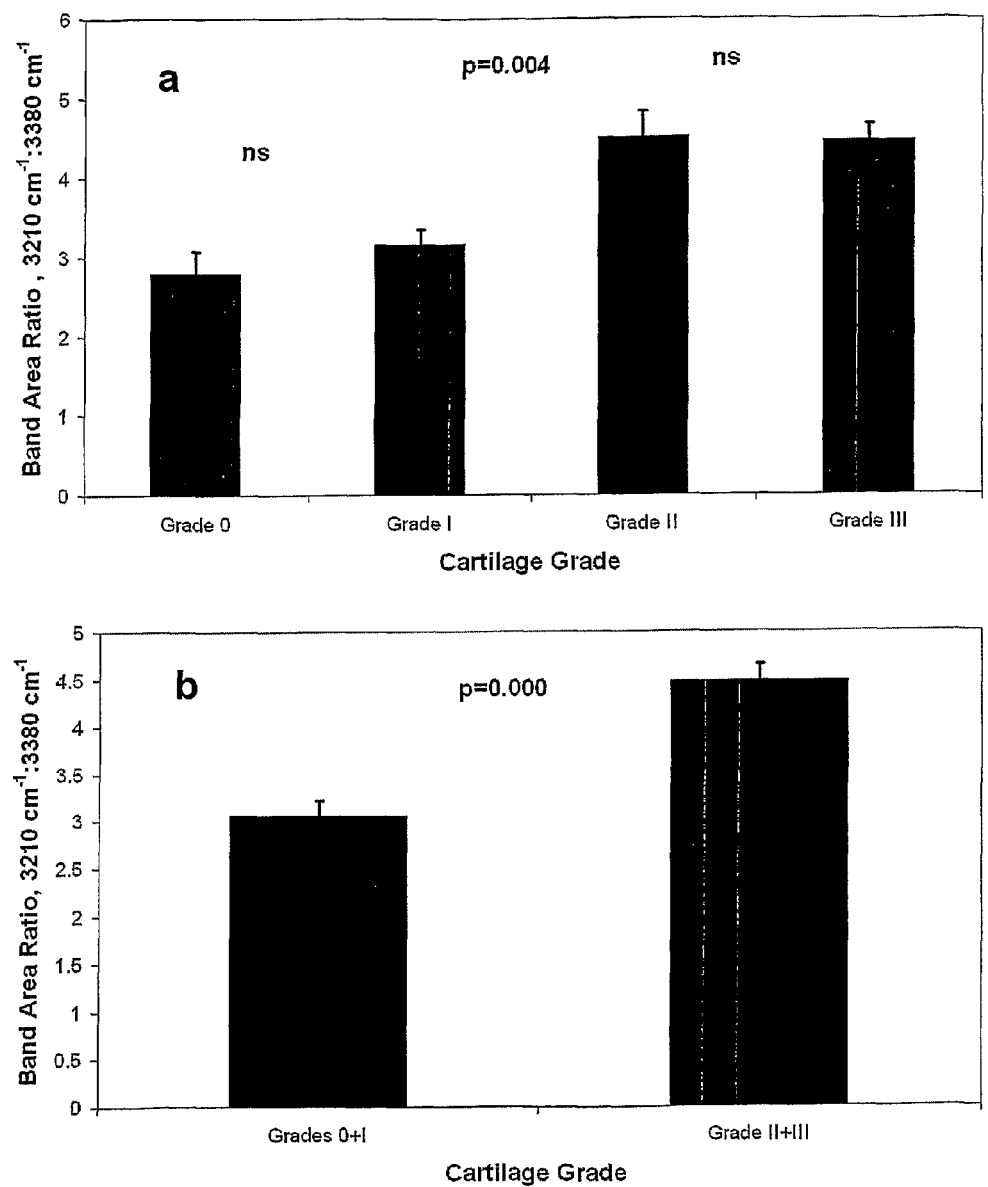

FIGS. 26a and 26b show bar charts illustrating the changes in mean ratio of the areas of the low-wavenumber band of the O—H complex at about 3,210 $cm^{-1}$ to that of the high-wavenumber band of the O—H complex at about 3,380 $cm^{-1}$ with cartilage grade. FIG. 26a shows the mean band area for all four Grades individually. FIG. 26b shows the mean band area for Grades 0 and I combined and Grades II and III combined. The error bars indicate the standard error for the mean and the p values indicate the significance of the difference in the mean band area between the two groups immediately below the stated value, with 'ns' indicating no significance.

Figure 27:
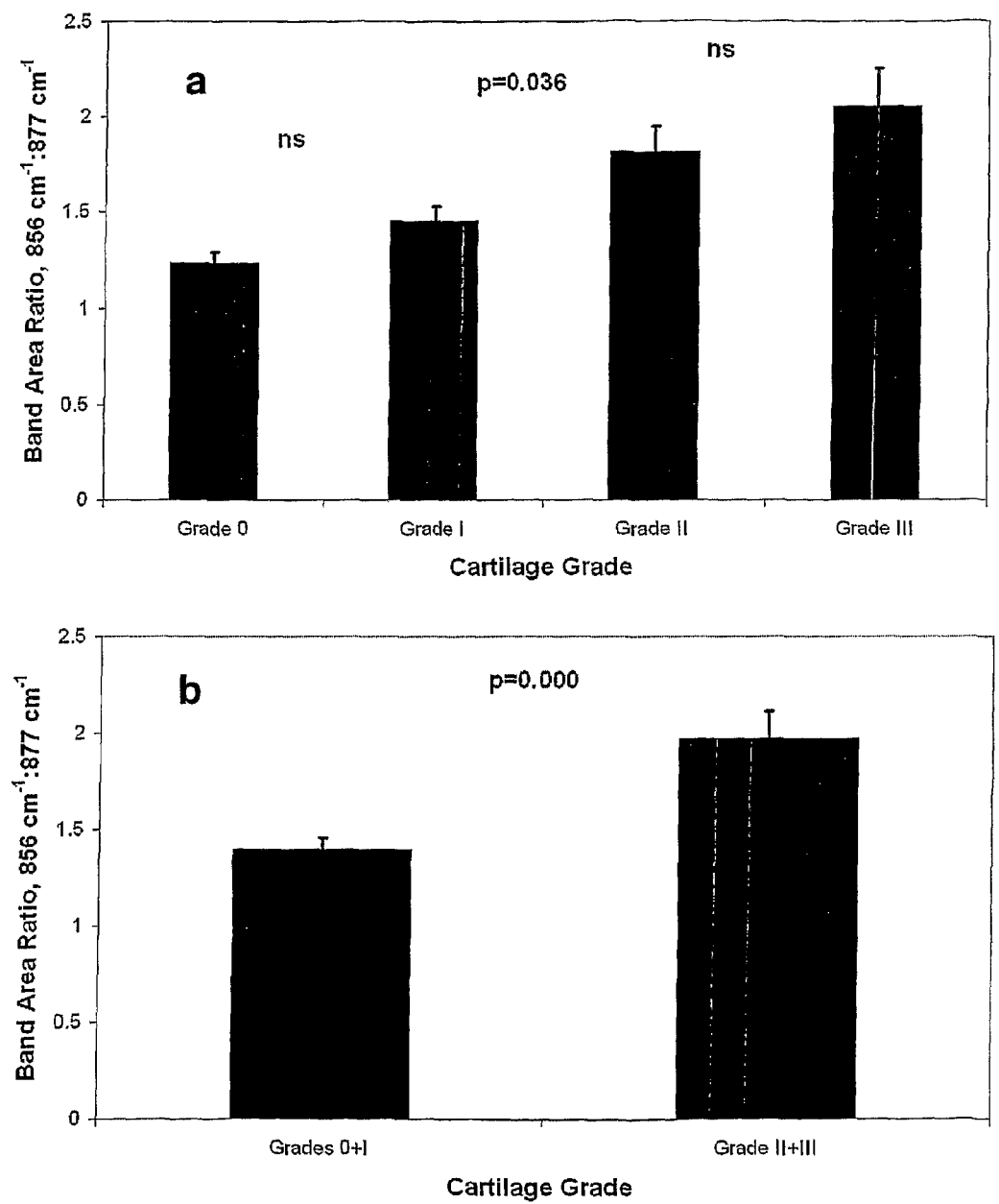

FIGS. 27a and 27b show bar charts illustrating the changes in mean ratio of the band areas of the proline band at about 856 $cm^{-1}$ to that of the hydroxyproline band at about 877 $cm^{-1}$ with cartilage grade. FIG. 27a shows the mean band area for all four Grades individually. FIG. 27b shows the mean band area for Grades 0 and I combined and Grades II and III combined. The error bars indicate the standard error for the mean and the p values indicate the significance of the difference in the mean band area between the two groups immediately below the stated value, with 'ns' indicating no significance.

Figure 28:
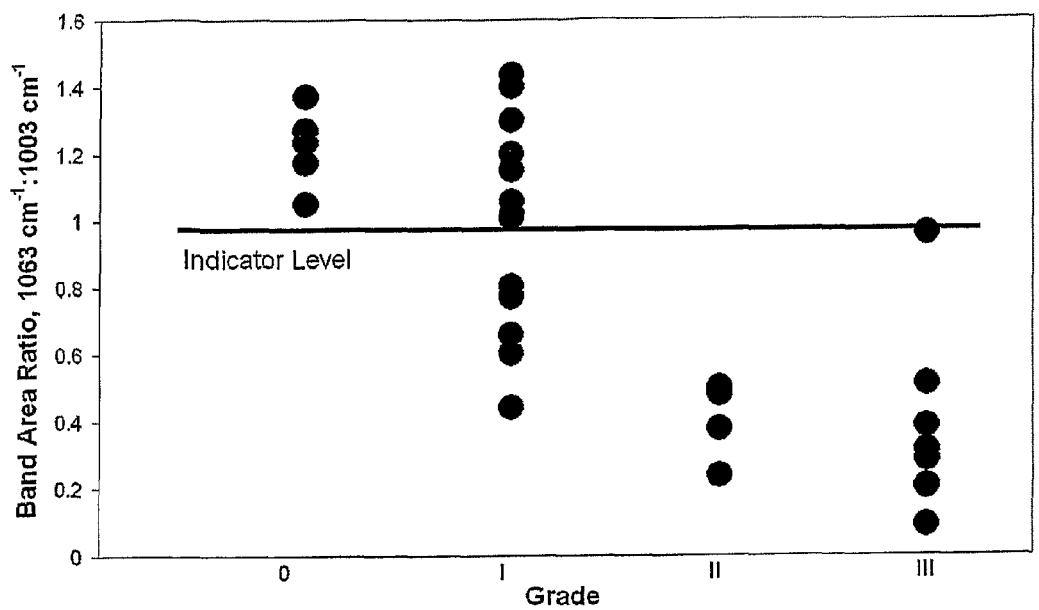

FIG. 28 shows a chart illustrating individual measurements of the ratio of band areas of the symmetric SO stretch of sulphate band at about 1,063 cm$^{-1}$ to the phenylalanine ring breathing band at about 1,003 cm$^{-1}$ categorised by cartilage grade. The 'Indicator Level' is the level below which the measured band area ratio indicates that there is appreciable degeneration within the cartilage tissue being analysed.

Figure 29:
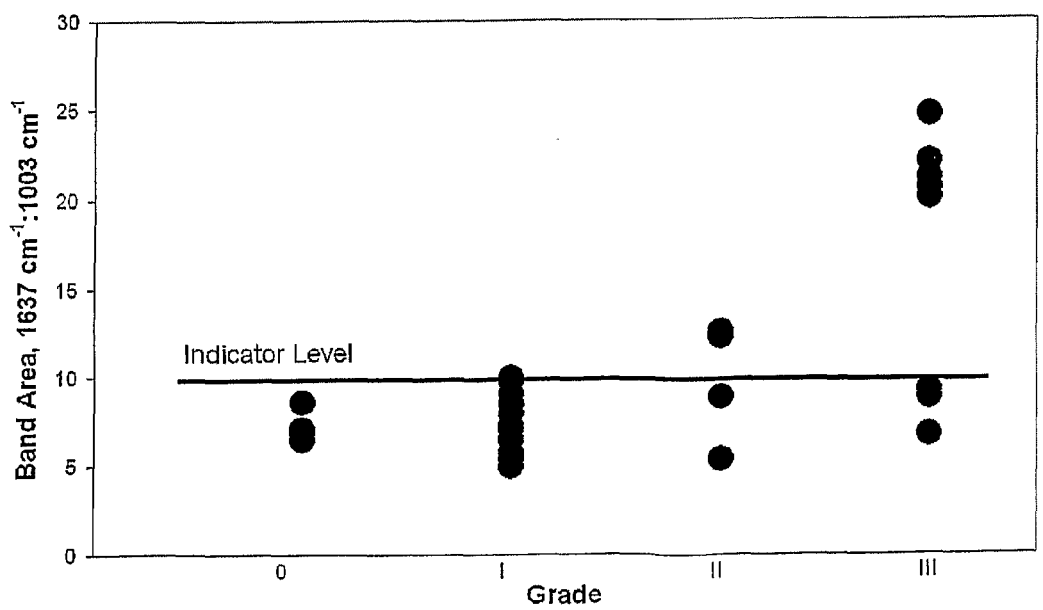

FIG. 29 shows a chart illustrating showing individual measurements of the ratio of band areas of the H$_2$O bend band at about 1,637 cm$^{-1}$ to the phenylalanine ring breathing band at about 1,003 cm$^{-1}$ categorised by cartilage grade. The 'Indicator Level' is the level above which the measured band area ratio indicates that there is appreciable degeneration within the cartilage tissue being analysed.

Figure 30:
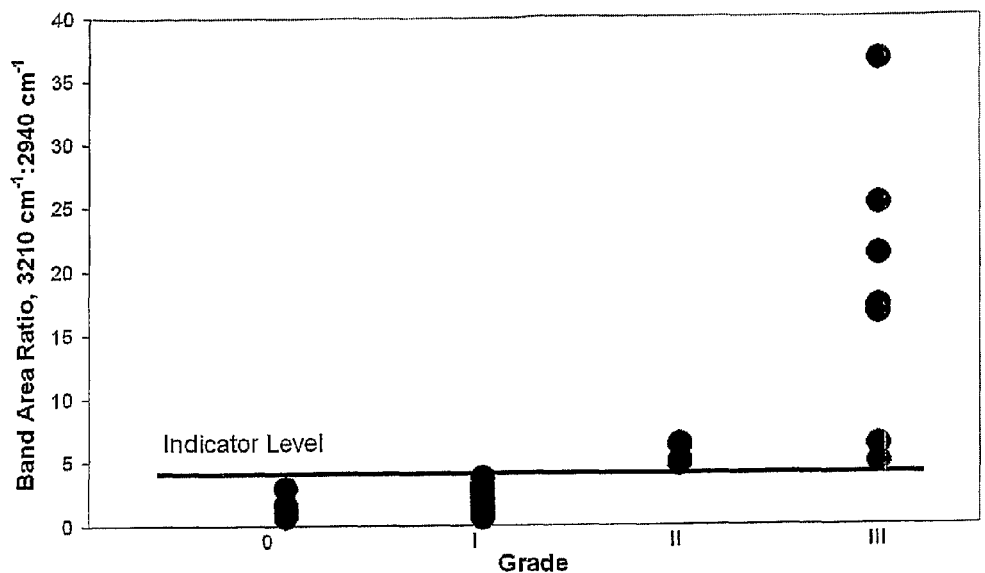

FIG. 30 shows a chart illustrating individual measurements of the ratio of band areas of the low-wavenumber band of the O—H complex at about 3210 cm$^{-1}$ to the CH stretch band at about 2,940 cm$^{-1}$ categorised by cartilage grade. The 'Indicator Level' is the level above which the measured band area ratio indicates that there is appreciable degeneration within the cartilage tissue being analysed.

Figure 31:
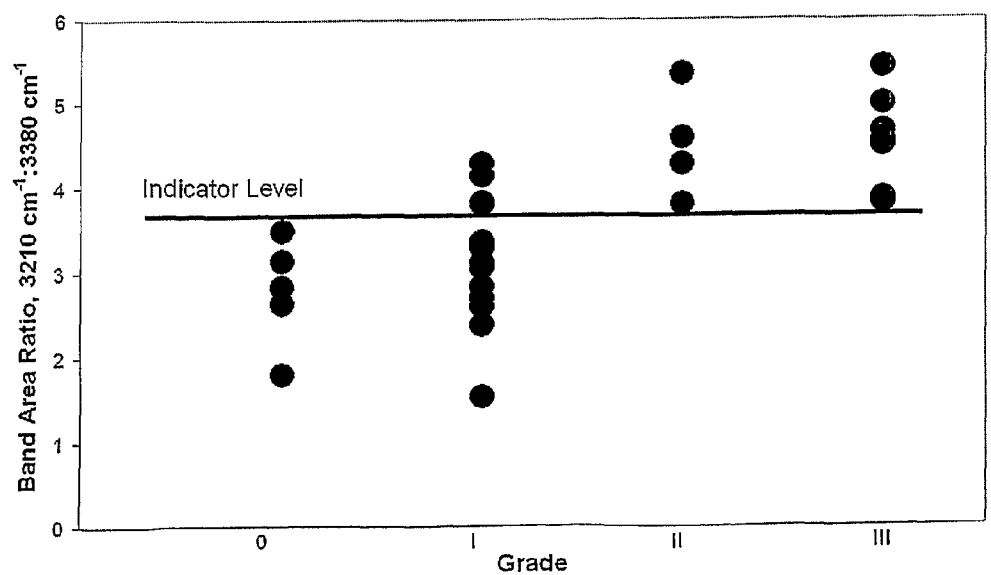

FIG. 31 shows a chart illustrating individual measurements of the ratio of band areas of the low-wavenumber band of the O—H complex at about 3,210 cm$^{-1}$ to the high-wavenumber band of the O—H complex at about 3,380 cm$^{-1}$ categorised by cartilage grade. The 'Indicator Level' is the level above which the measured band area ratio indicates that there is appreciable degeneration within the cartilage tissue being analysed.

Figure 32:
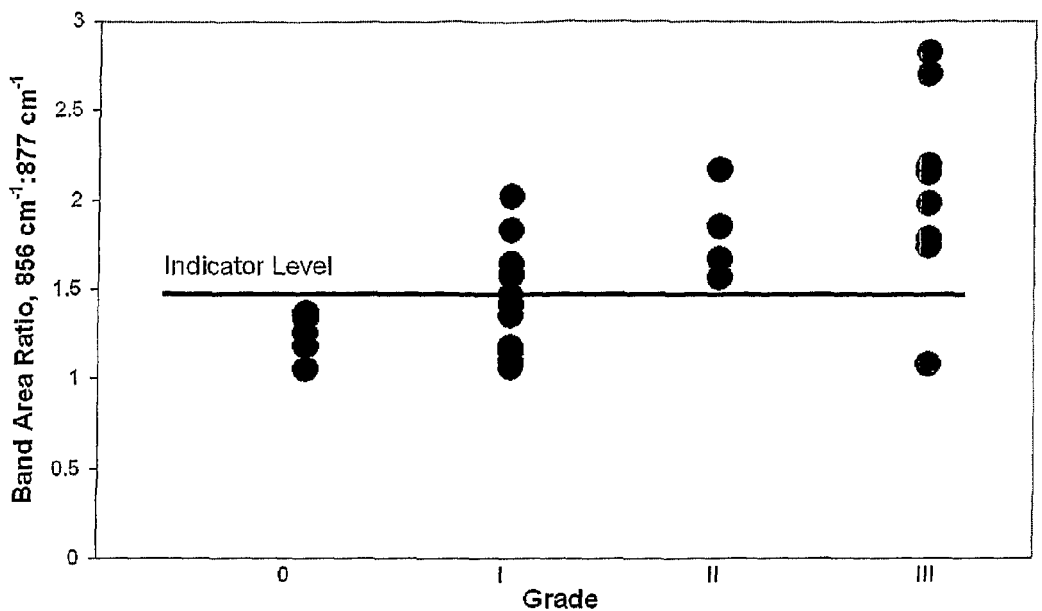

FIG. 32 shows a chart illustrating individual measurements of the ratio of band areas of the proline band at about 856 cm$^{-1}$ to the hydroxyproline band at about 877 cm$^{-1}$ categorised by cartilage grade. The 'Indicator Level' is the level above which the measured band area ratio indicates that there is appreciable degeneration within the cartilage tissue being analysed.

Figure 33:
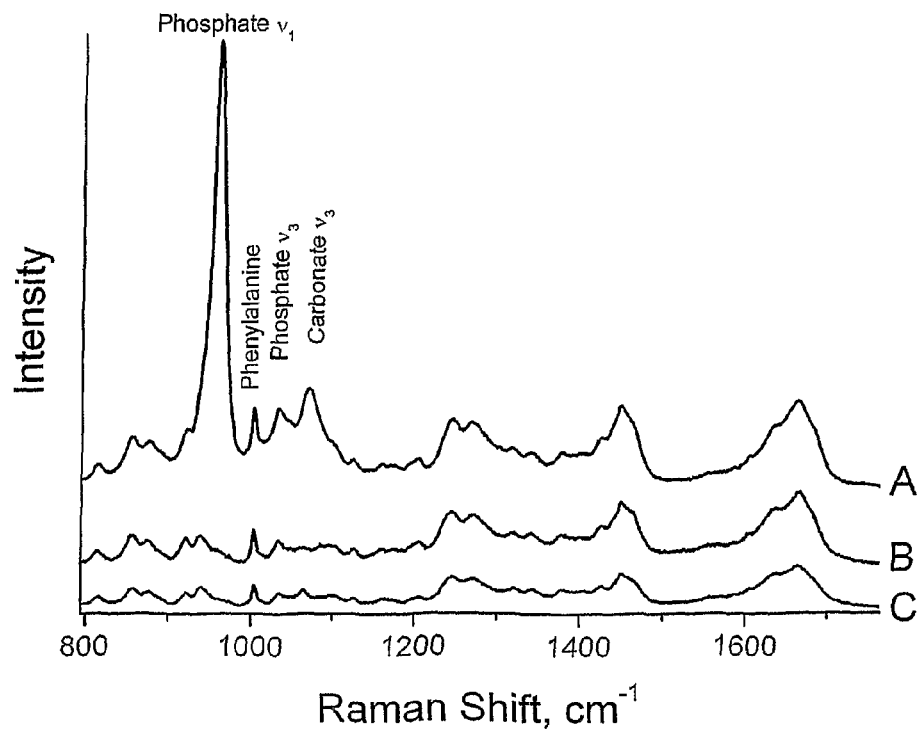

FIG. 33 shows a typical Raman spectra of full thickness cartilage tissue and of bone tissue showing that the full thickness cartilage contain no discernible spectral features of bone. Spectrum A is a typical spectrum of bone tissue, spectrum B a typical spectrum of full thickness Grade I cartilage, spectrum C a typical spectrum of full thickness Grade 0 cartilage.

Figure 34:
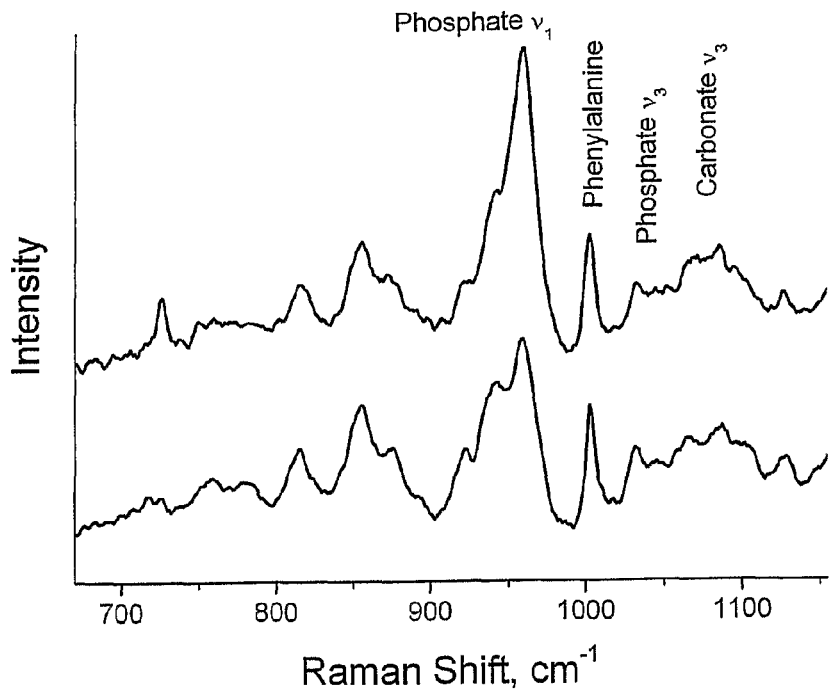

FIG. 34 shows two Raman spectra of eroded Grade III cartilage tissue, both showing clear and discernible spectral features of bone.

Figure 35:
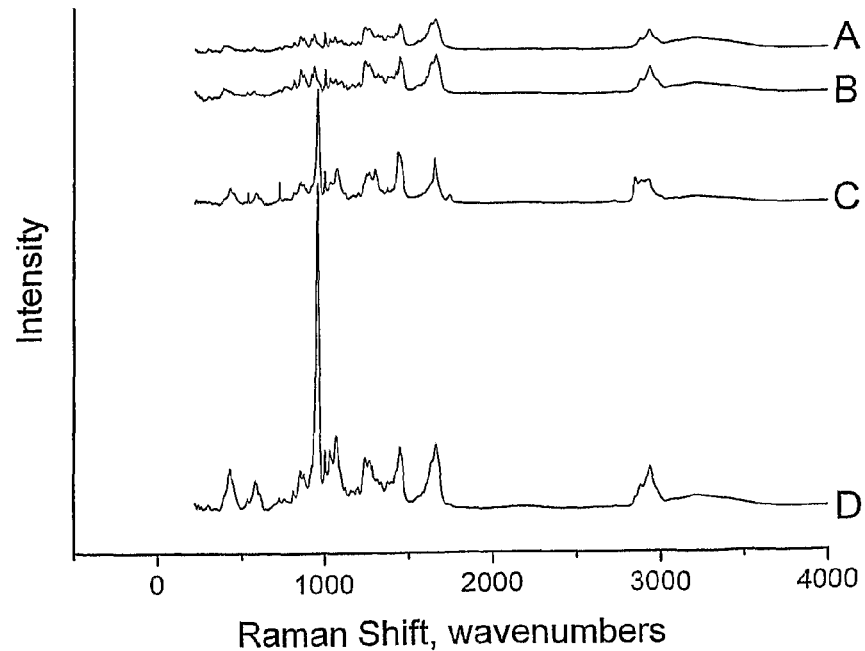

FIG. 35 shows Raman spectra taken at different depths through a full thickness Grade 0 cartilage sample from the joint surface to the subchondral bone tissue, spectrum A from the joint surface, spectrum B from deep cartilage, spectrum C from the mineralised cartilage layer, and spectrum D from the subchondral bone.

Figure 36:
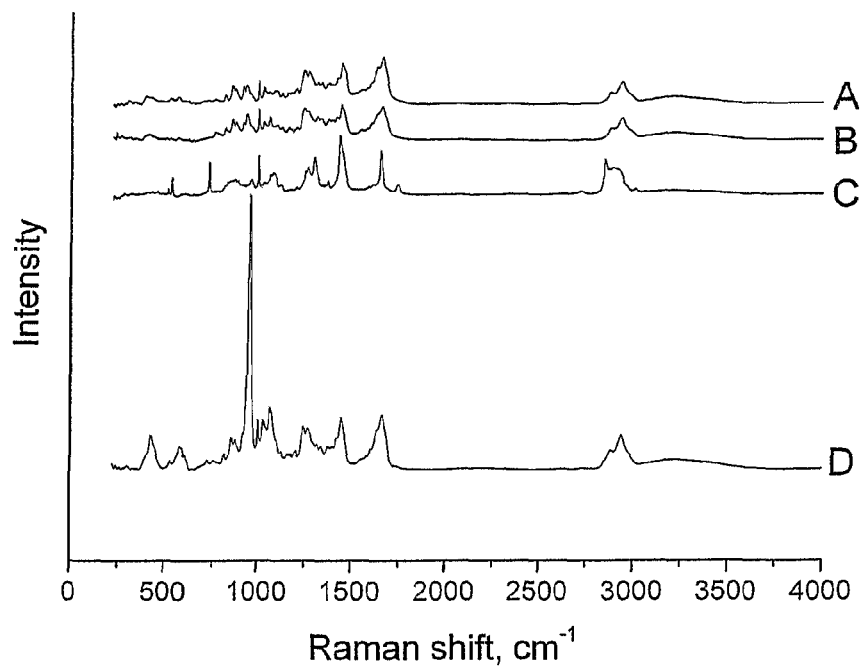

FIG. 36 shows Raman spectra taken at different depths through a full thickness Grade I cartilage sample from the joint surface to the subchondral bone tissue, spectrum A from the joint surface, spectrum B from deep cartilage, spectrum C from the mineralised cartilage layer, and spectrum D from the subchondral bone.

Figure 37:
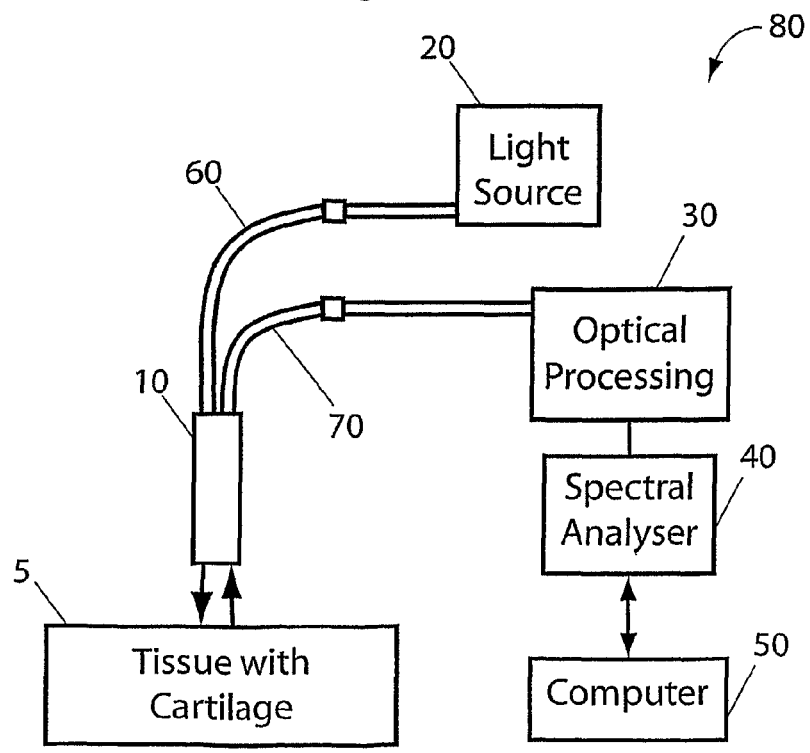

FIG. 37 shows a schematic diagram of an apparatus according to an embodiment of the invention.

Figure 38:
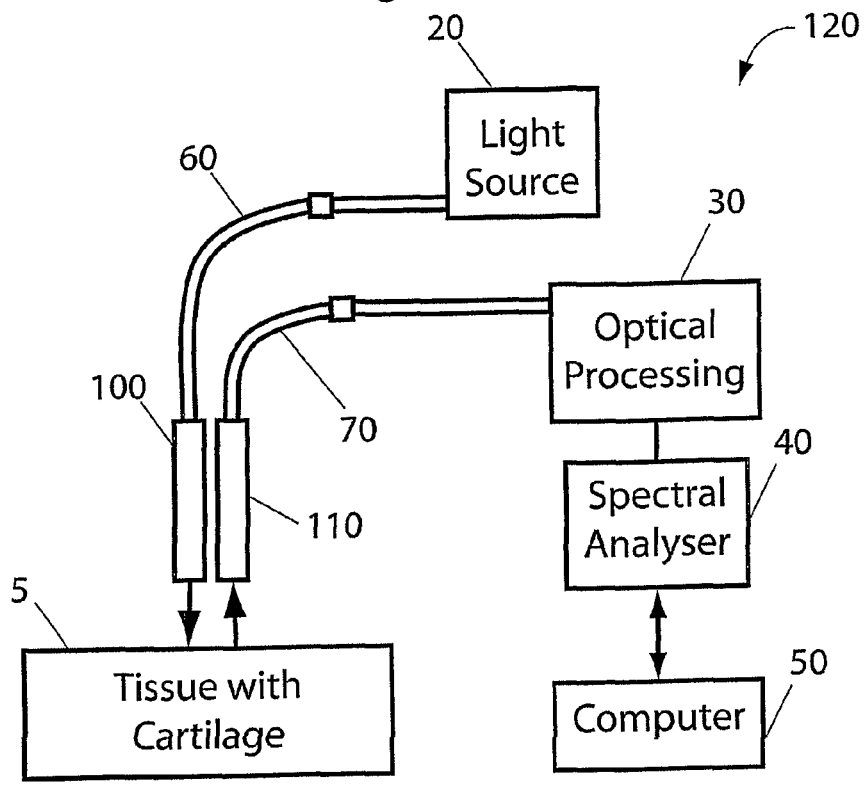

FIG. 38 shows a schematic diagram of an alternative apparatus according to an embodiment of the invention.

Figure 39:
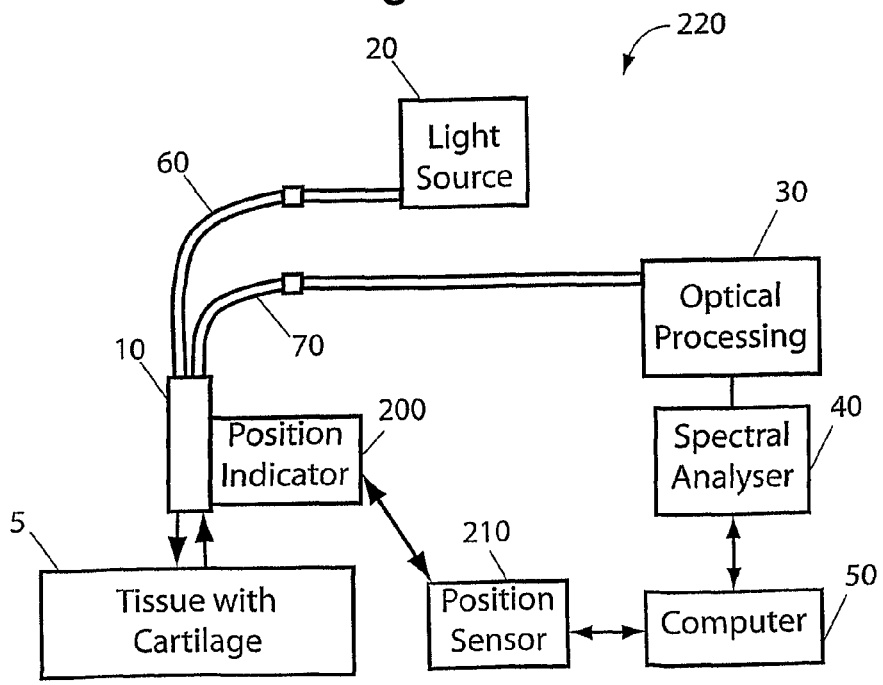

FIG. 39 shows a schematic diagram of a further alternative apparatus according to an embodiment of the invention.

Figure 40:
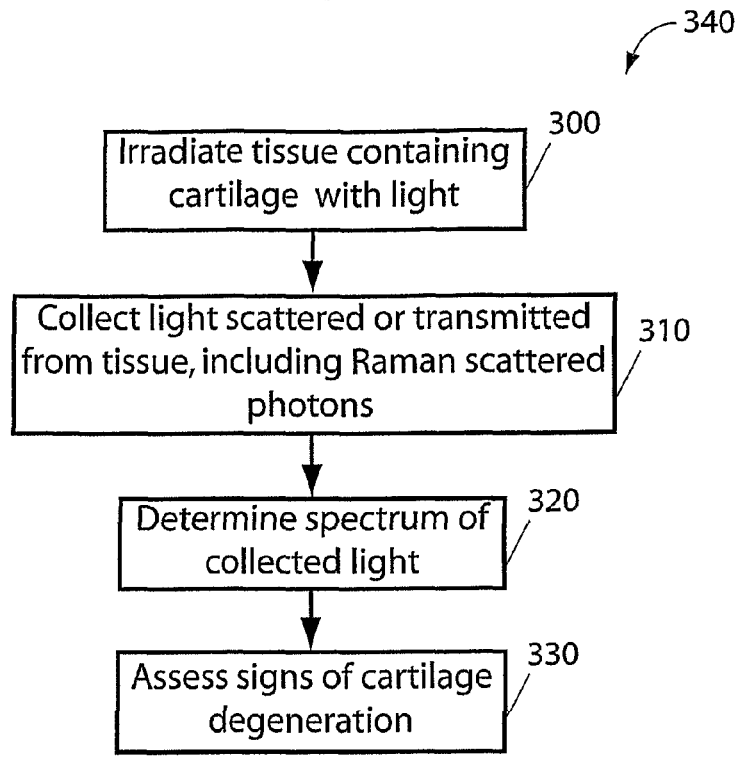

FIG. 40 shows a flow diagram of a method according to an embodiment of the invention.

Figure 41:
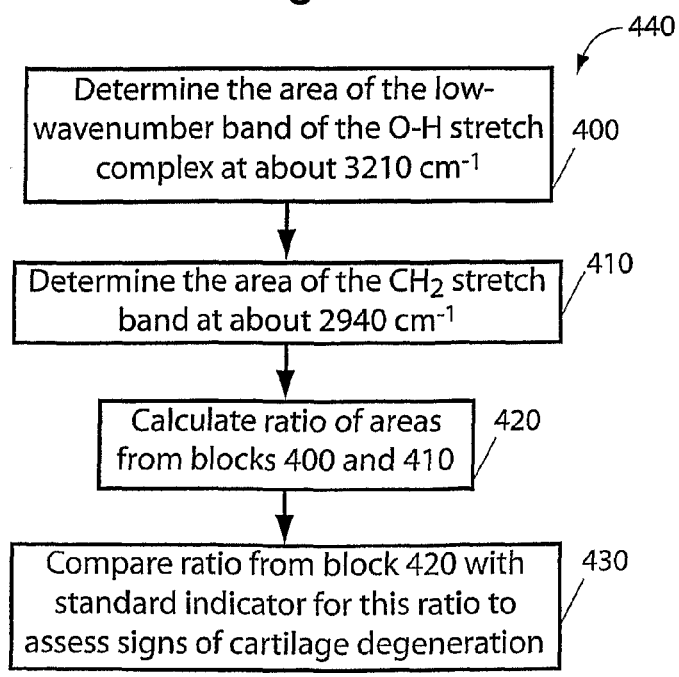

FIG. 41 shows a flow diagram of a method according to an embodiment of the invention.

Figure 42:
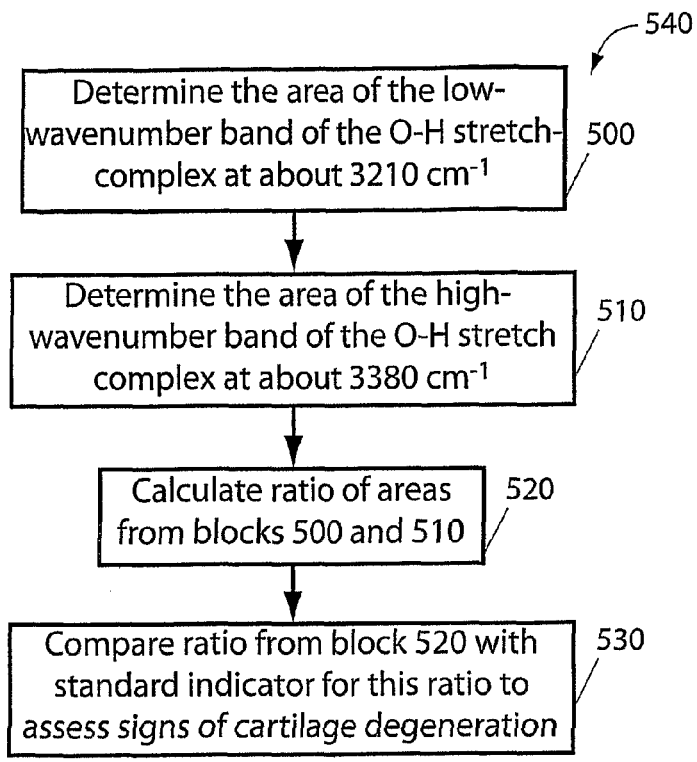

FIG. 42 shows a flow diagram of a method according to an embodiment of the invention.

Figure 43:
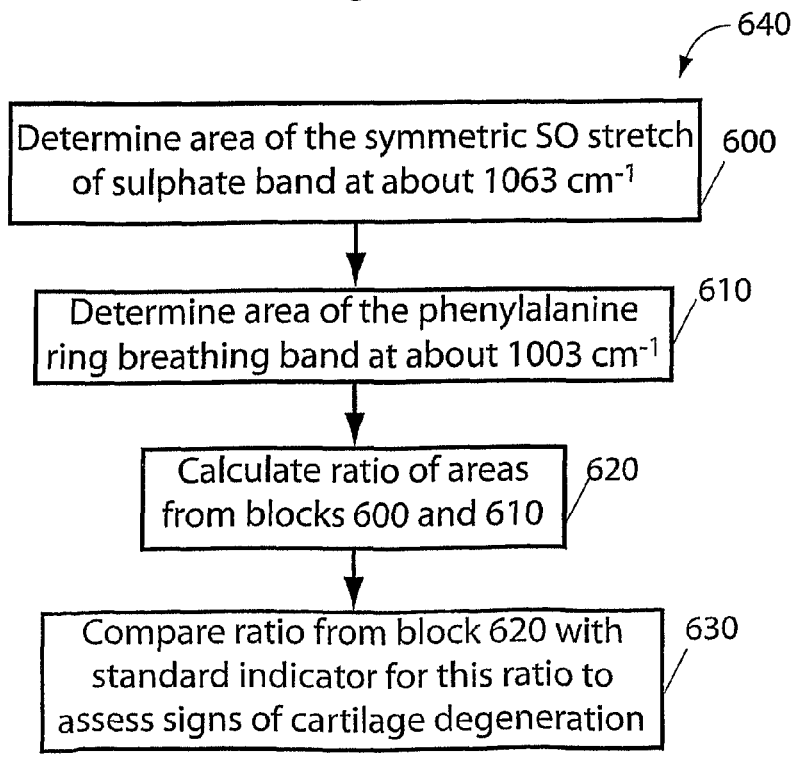

FIG. 43 shows a flow diagram of a method according to an embodiment of the invention.

Figure 44:
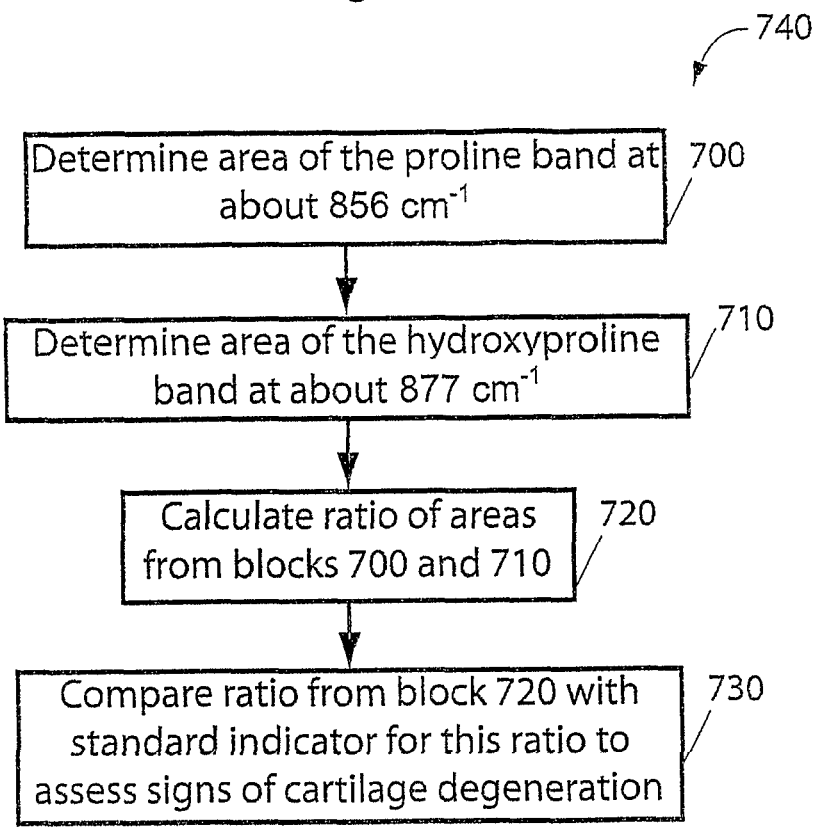

FIG. 44 shows a flow diagram of a method according to an embodiment of the invention.

EXAMPLE 1

Investigation of Cartilage Degradation Using Raman Spectroscopy

Introduction

Arthritis is a painful condition affecting the joints. It is one of the major causes of disability in the Western world and presents at similarly elevated levels of prevalence across the developed world. While it can affect all ages, it is particularly prevalent in the elderly, obese individuals and certain athletic professions. With an ever increasing ageing population and a rise in obesity levels at all ages, these types of musculoskeletal conditions will become progressively more important. Since these conditions do not directly threaten life, and combined with increasing longevity, the number of years that individuals will suffer from disability and remain dependent on others will increase also.

Currently, in the UK over 15% of the population (7 million adults) have long-term health problems due to arthritis and related conditions. DJD is the most common of these; for instance for those over 65 year no other medical condition leads to greater impairment in mobility. The joints most commonly affected are the knee, hip, hand, spine and foot, with some 4.4 million people in the UK having X-ray evidence of moderate to severe DJD in their hands. It is DJD of the large weight-bearing joints of the knee and hip (750,000 individuals), which has the greatest population impact due to reduced mobility and disability resulting from pain and stiffness.

Despite this, in the main, current treatments for DJD target the clinical symptoms, mostly pain relief, rather than underlying disease process itself, which manifests as a progressive loss of the articular cartilage on the opposing bone surfaces of the joint. This has lead in the past to a tendency to delay medical or surgical intervention, other than that of symptomatic relief, until the disease had progressed to a stage where a surgical intervention in the form of partial or complete joint surface replacement, was deemed essential. However, there are many exciting new therapies that are being considered and being developed that are likely, at least, to slow the progression of the degradative cascade. These forms of intervention will be best performed as early in the progression of the disease as possible but this will require reliable, objective and sensitive assessments of cartilage health that are currently not possible at the earliest stages of the disease.

Current methods of diagnosis of DJD are based on joint pain, which is exacerbated by exercise and relieved by rest, joint stiffness and reduced function. The diagnosis is then confirmed radiographically, which suffers from poor sensitivity particularly in the initial stages of the disease. In consequence this diagnostic approach is fine only if early diagnosis is not deemed to be essential.

A major aspect of DJD is the breakdown of the articular cartilage which normally functions to reduce friction between the bone surfaces and protects against the impact of load during locomotion in the weight-bearing joints. Cartilage breakdown first appears as focal lesions in the tissue, which subsequently form large areas of erosion of the lubrication surfaces. However, it is known that biochemical changes in the components that cartilage is made of can be detected prior to radiographic changes. Technologies that monitor and measure these types of biochemical changes of cartilage components should, in principle, lead to earlier therapeutic intervention (Takahashi et al, 2004).

Radiographic technology, such as CT, is insensitive in this tissue, because the greater majority of cartilage has no mineral phase to which X-rays are sensitive. Other imaging modalities such as MRI detect the presence and distribution of water and thus measure the three-dimensional geometry of the structure being investigated. This gives valuable information on the loss of tissue, but only once the disease has progressed to the point where tissue loss has occurred. These technologies do not allow measurement of the biochemical changes within the cartilage.

Cartilage has two major organic components that account for the bulk of its extracellular matrix: 1) 15% to 22% of the wet weight of cartilage comprises a network of collagen (type-II) with small proteoglycans associated with it; and 2) 4% to 6% comprises aggregates of larger proteoglycans, which control the imbibement of water into the tissue that is essential to its mechanical properties, hydration and organisation of many other components. The largest component of cartilage tissue is water, 60%-85%, it is the ability of cartilage to manipulate the water captured within it that determines its mechanical and physical properties. With respect to biochemical changes the degradation of proteoglycans is considered to be early but reversible, whereas damage to the collagen network is widely considered to be irreversible and therefore the 'point of no return' with regards to tissue integrity. Other biochemical changes include more subtle alterations to many protein and non-protein components of the extracellular matrix. Various forms of spectroscopy can be adapted to reveal these biochemical changes. However, for most major joints the cartilage lies at depths to the surface that are far greater than that illuminated from the skin surface, making the measurement of joint impractical as a completely non-invasive technique.

There is a well-established minimally-invasive approach to the major joints, known as arthroscopy, in which fibre optic cameras and hand-held instruments are inserted into the joint. This allows direct inspection of the joint including its cartilaginous surfaces. This route to the joint surface will allow the state of the cartilage to be measured spectroscopically and directly.

Of the various forms of spectroscopy, Raman spectroscopy is the most relevant because it detects returning scattered photons, rather than absorption of photons which is best performed using trans-illumination, because it returns information on the covalent bonds found within the substance being investigated. Hand-held devices to perform Raman spectroscopy are now available commercially (e.g. Ahura Scientific, USA), though these devices are not currently suitable for the study of DJD. In cartilage, Raman spectroscopy gives information on the collagen and the proteoglycans with their sulphated polysaccharides, the glycosaminoglycans or GAGs. This includes information on the sulphate groups substituted on the GAGs and the amide I and III bonds within the collagen.

While Fourier-transform infra-red (FTIR) spectroscopy has been used for several years to measure the biochemical components of cartilage in vitro, its reliance on infrared light, which is readily absorbed by water, makes it less suitable for measurements in vivo of highly hydrated tissues such as cartilage. On the other hand Raman spectroscopy has none of the technical limitation of FTIR for in vivo analysis and has been used in this way to measure a variety of tissue, including bone (Matousek et al, 2006), though little attention has been paid to its use on cartilage.

We have shown that Raman spectroscopy has the exciting potential of measuring changes in: the collagen network, the proteoglycans, the sulphated GAGs as well as water. However, there is a body of scientific work that suggest that the important proteoglycans and the GAGs show no significant features in the Raman spectra of cartilage (Dehring et al, 2006; Mizuno et al, 1994, US 2007/0049808), though our findings show that features, particularly of the sulphate group of the GAGs, are readily visualised from human cartilage. This is supported by direct studies of proteoglycans and GAGs (Bansil et al, 1978; Koljenovic et al, 2004; Meziane-Tani et al, 2006), as well as studies of cartilage from other regions of the body (Koljenovic et al, 2004). This reported inability to detect features associated with GAGs may be due the size of the samples (Mizuno et al, explored small explants from the surface of the eye and Dehring et al, measured the surface of the murine femur) or from the storage, fixing, drying i.e. by storing in ethanol or photobleaching processes, all procedures that were avoided in the experiments described later.

It has been the practice in studies by other workers to limit the spectra to a range between about 800 to 1,800 wavenumbers; the so-called "fingerprint" region of the spectrum. There are several important peaks that lie outside of this range in particular the CH stretch band and O—H stretch complex that lie above about 2,500 $cm^{-1}$.

The aim of this section of the document is to outline all the features from Raman spectra recorded from the surface of unfixed, but frozen samples of human cartilage that can be used to detect changes in tissue biochemistry and monitor the progress of degenerative joint diseases.

Methods

Full thickness cartilage samples from the synovial surface down to and including the subchondral bone were taken from the tibial plateau and femoral condyles of human knees from patients who had undergone lower limb amputation for non-orthopaedic reasons. The range of ages of the patients was from 18 years to 74 years. Each sample was allocated one of four grades defined as:

Grade 0 healthy full thickness cartilage from a joint with no signs of degeneration;

Grade I full thickness cartilage from a joint with a distinct degenerative lesion elsewhere in the joint than the point of harvest;

Grade II from the edge of a distinct degenerative lesion at a point where there was early signs of degeneration; and Grade III from the centre or around the centre of a distinct cartilage at a point where there is signs of deep erosion and high levels of degeneration.

Sample population sizes were Grade 0 n=5, Grade I n=14, Grade II n=5, and Grade III n=8.

No sample underwent any form of preparation other than freezing at −80° C. Each sample was allowed to thaw fully while under complete immersion in deionised water. It was shown that total immersion in water rather than synovial fluid had little effect on the Raman spectra so all spectra were recorded with the samples fully immersed in deionised water. A Raman spectrometer system equipped for microbeam Raman spectroscopy (InVia Raman Microscope, Renishaw plc, UK) was used. The Raman spectrum was excited using a commercially available diode laser operating at a wavelength of 785 nm (Renishaw plc, UK). The power setting of the incident laser was adjusted to optimise the quality of the spectrum and to avoid damage to the tissue under investigation. The laser light was focused on the relevant area of the sample using a microscope objective lens (Leica Microsystems Wetzlar GmbH, Germany; 50× magnification; numerical aperture 0.50). The Raman scattered light was collected through the same lens and directed into the spectrometer system.

The spectral range that can be examined as well as the resolution of individual peaks or bands in a given spectrum for a given exciting wavelength is determined by the spacing between lines in the diffraction grating that is used as an optical dispersing element in the spectrometer. A grating with 1,200 lines/mm was used. This grating was scanned to permitted data to be collected between 100 and 4,000 wavenumbers ($cm^{-1}$) for each exposure of the dispersed wavelength spectrum of scattered light on the detector. Each spectrum was recorded as the sum of four exposures of 30 seconds. The detector was a CCD array cooled to −70° C.

Analysis was performed using a commercial package (OriginPro 7, v7, OriginLab Corp, USA). Any spikes due to cosmic rays were removed. The signal to noise ratio of the organic bands of the spectra of the Grade II and Grade III was sufficiently low that it was necessary to smooth spectra using adjacent averaging with the number of points set at 5. The spectra of Grades 0 and I had high signal to noise ratio and were not smoothed. Background fluorescence was removed. A Lorentzian curve fitting tool was used with the band offset at zero. This tool measured band area, band position, and band width.

In the Raman spectroscopy system that we used there is a known systematic error that can result in the spectral features apparently losing intensity at higher wavenumbers. As is usual, we did not remove this error because the statistical routines that we used are inherently insensitive to this type of error, and doing so would not affect the ability to detect or diagnose degeneration in cartilage.

TABLE I

Band Assignments

| Band Centre | Band Strength | Assignment |
|---|---|---|
| 815 | w | |
| 856 | m | ν (C—C) of proline ring |
| 877 | m | ν (C—C) of hydroxyproline ring |
| 921 | m | ν (C—C) of proline ring |
| 940 | m | ν (C—C) of protein backbone |
| 962 | w | Amide III |
| 1003 | m | Phenylalanine ring breathing |
| 1032 | m | Proline |
| 1043 | w | Out of plane bend of carboxyl OH |
| 1063 | m/w | Symmetric SO stretch of sulphate |
| 1096 | w | ν (C—N) |
| 1127 | w | $NH_3^+$ |
| 1162 | w | |
| 1175 | w | Tyrosine |
| 1204 | w | Hydroxyproline, tyrosine |
| 1244 | s | Amide III |
| 1272 | s | Amide III |
| 1320 | m | $CH_3$ twist, $CH_2$ twist |
| 1342 | m | $CH_3$ wag, $CH_2$ wag |
| 1391 | m | |
| 1426 | m | $\nu_3$ (COO$^-$) |
| 1451 | s | δ ($CH_3$, $CH_2$) |
| 1465 | s sh | δ ($CH_3$, $CH_2$) |
| 1562 | w | Amide II |
| 1606 | w | Phenylalanine, tyrosine |
| 1637 | s | $H_2O$ bend |
| 1665 | s | Amide I |
| 1683 | w | |
| 2740 | w | |
| 2889 | w sh | ν ($CH_2$) symmetric |

TABLE I-continued

Band Assignments

| Band Centre | Band Strength | Assignment |
|---|---|---|
| 2940 | s | ν ($CH_3$) symmetric; ν ($CH_2$) asymmetric |
| 2980 | w sh | ν ($CH_3$) symmetric |
| 3210 | s | Low-wavenumber band of the OH stretch complex |
| 3380 | s | High-wavenumber band of the OH stretch complex |

The spectral complex of the three bands at about 2,889 $cm^{-1}$, 2,940 $cm^{-1}$ and 2,980 $cm^{-1}$ are collectively referred to within this document as the CH stretch band The band assignments reflects the current understanding and may be subject to future changes as the understanding of the complex biological systems of cartilage and other tissues improve.

Key to abbreviations: s strong, m medium, w weak, sh shoulder, ν stretching coordinate, and δ deformation coordinate.

The groups were compared statistically either as four separate groups or as two groups with Grades 0 and I combined and Grades II and III combined. When four groups were being compared single factor ANOVA was used, the Student t test was then used to discover between which groups any statistical differences was found. When two groups were compared the Student t test was used. A 5% significance level was used.

Results

Figure 1:
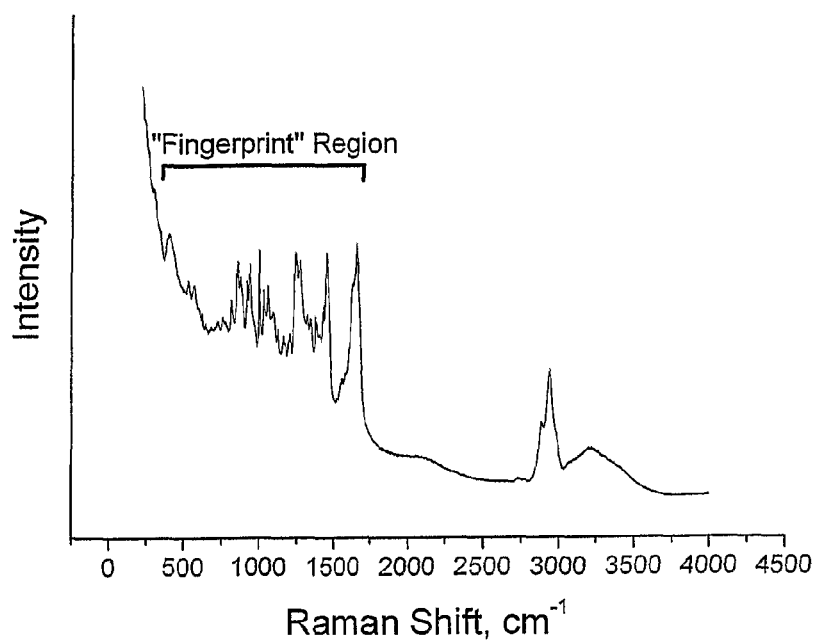
Figure 2:
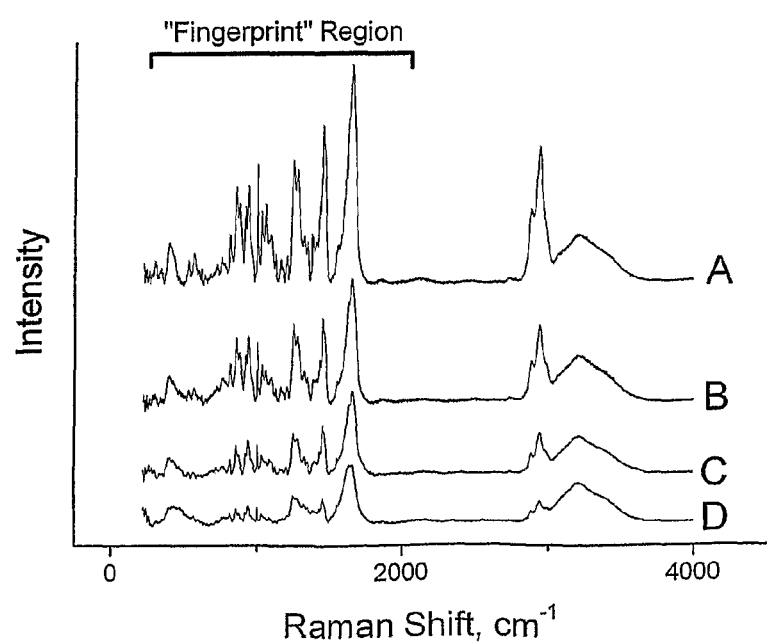

All bands showed significantly reduction of band area with increasing grade of degeneration except the low- and high-wavenumber bands of the O—H stretch complex at about 3,210 $cm^{-1}$ and 3,380 $cm^{-1}$, this reduction can be seen in FIG. 2. To avoid any small inter-spectral changes in intensity, band areas were analysed relative to the area of a neighbouring band. Two bands were chosen as references: the phenylalanine ring breathing band at about 1,003 $cm^{-1}$, chosen because it is a narrow band that stands quite distinct from its neighbouring bands, and the CH stretch band at about 2,940 $cm^{-1}$.

Sulphate

In the Grade 0 and Grade I groups the symmetric SO stretch of sulphate band at about 1,063 $cm^{-1}$ is prominent despite the erroneous statements of other researchers that this sulphate group makes "an insignificant contribution to the overall Raman spectrum" (Dehring et al, 2006b), FIGS. 11 to 14. However, its band area fell off more rapidly with degeneration than the bands associated with organic chemical groups FIGS. 11, 12, 13 and 14. The mean band area relative to the phenylalanine ring breathing band at about 1,003 $cm^{-1}$, FIG. 23b, showed a significant difference in the mean relative area between the Grades 0 and I group and that of the Grades II and III groups. When comparing the mean relative band areas of all four Grade groups, there was a fall of relative area with increasing grade of cartilage degeneration with a significant difference between the relative means of the Grade I and Grade II groups, FIG. 23a. The changes in the relative area of this sulphate peak are commensurate with the known loss of sulphate with cartilage degeneration through the loss of proteoglycans and glycosaminoglycans to which the sulphate group is bonded.

Water

Three different bands were used in the analysis of water within the tissue, FIGS. 5, 6, 7, 8, 9, 10, 15, 16, 17 and 18: $H_2O$ bend band at about 1,637 $cm^{-1}$ used to estimate amount of water within the tissue, the low- and high-wavenumber bands of the O—H stretch complex at about 3,210 $cm^{-1}$ and 3,380 $cm^{-1}$, respectively.

The mean area of the $H_2O$ bend band at about 1,637 cm$^{-1}$ when measured relative to the phenylalanine ring breathing at about 1,003 cm$^{-1}$ increased significantly with cartilage degeneration with a significant increase in the mean relative areas between the Grades 0 and I group and that of the Grades II and III group, FIG. 24b. When comparing the four groups a significant increase in the mean relative area was found between the Grade I and the Grade II groups, FIG. 24a.

A similar pattern of behaviour was found for the low-wavenumber band of the O—H stretch complex at about 3,210 cm$^{-1}$ when it was measured relative to the CH stretch band at about 2,940 cm$^{-1}$. There was a significant increase in mean relative area with increasing grade of cartilage degeneration with a significant increase in the mean relative areas between the Grades 0 and I group and that of the Grades II and III group, FIG. 25b. When comparing the four groups a significant increase in the mean relative area was found between the Grade I and the Grade II groups, FIG. 25a.

The relative changes in area of these two water-related bands is commensurate with the known increase in water content as cartilage shows increasing signs of degeneration.

The low-wavenumber band of the OH stretch complex at about 3,210 cm$^{-1}$ was also measured relative to the high-wavenumber band OH-stretch complex at about 3,380 cm$^{-1}$. This showed a significant increase in the mean relative area with higher grade of cartilage degeneration with a significant increase in the mean relative areas between the Grades 0 and I group and that of the Grades II and III group, FIG. 26b. When comparing the four groups a significant increase in the mean relative area was found between the Grade I and the Grade II groups, FIG. 26a. This relative change in band area is commensurate with changes in the manner in which the water is bound to the cartilage tissue with increasing signs of degeneration and increasing amounts of water within the tissue.

Proline to Hydroxyproline

Figure 3:
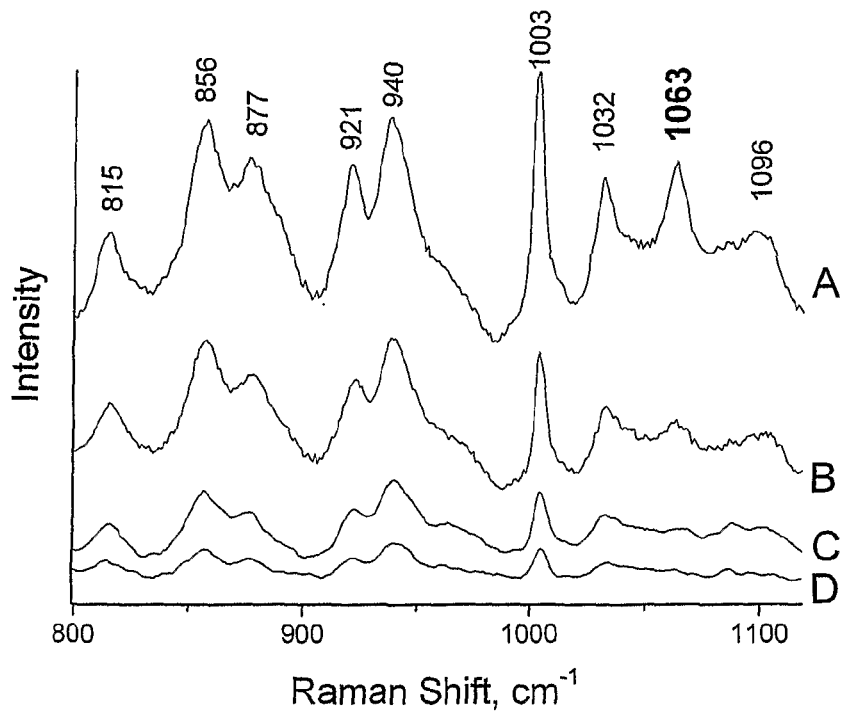
Figure 4:
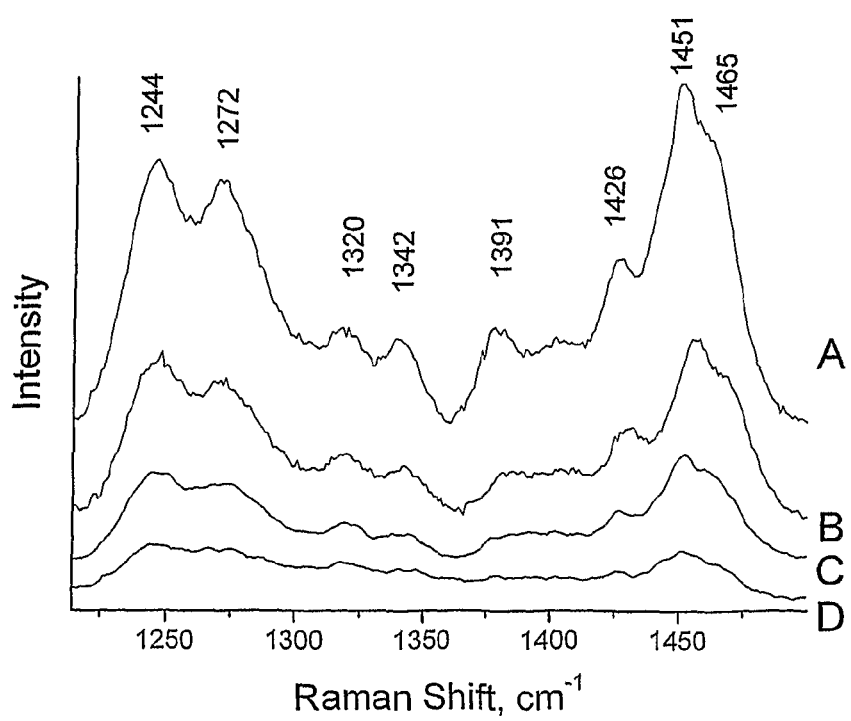
Figure 5:
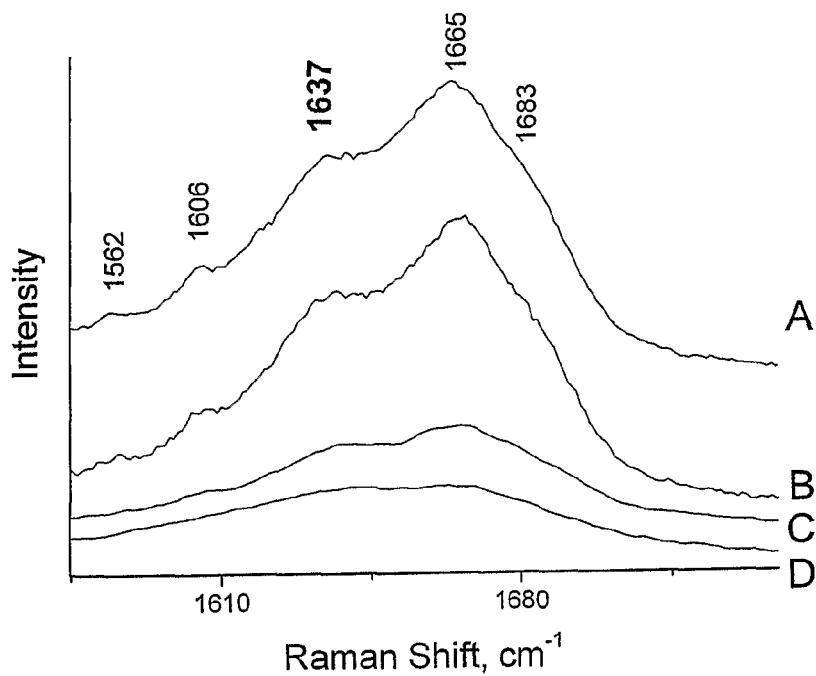
Figure 6:
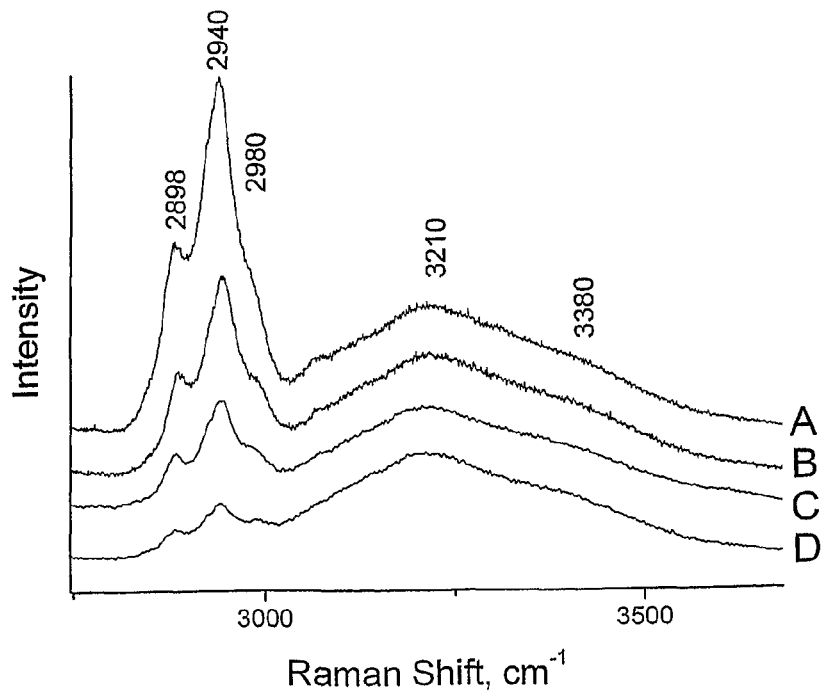
FIG. 6 shows typical Raman spectra of cartilage of different levels of degeneration from the range 2,740 $cm^{-1}$ to 3,680 $cm^{-1}$. Spectrum A is a typical spectrum of Grade 0 cartilage, spectrum B a typical spectrum of Grade I cartilage, spectrum C a typical spectrum of Grade II cartilage, and spectrum D a typical spectrum of Grade III cartilage.
Figure 7:
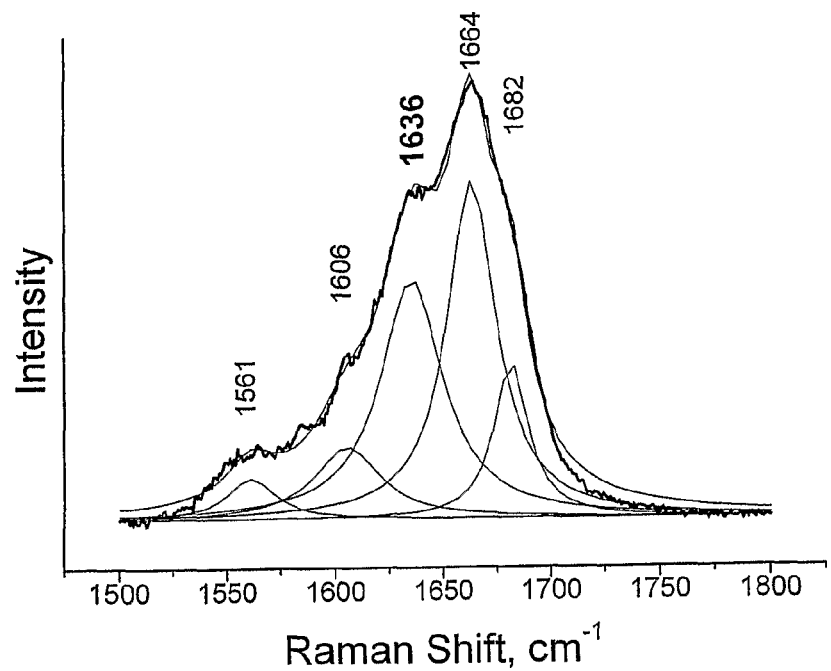
FIG. 7 shows a typical Raman spectrum of cartilage of Grade 0 showing the region 1,500 $cm^{-1}$ to 1,800 $cm^{-1}$ and how it has been deconstructed into five bands, the most important of which is the $H_2O$ bend band at about 1,637 $cm^{-1}$ (marked in bold).
Figure 8:
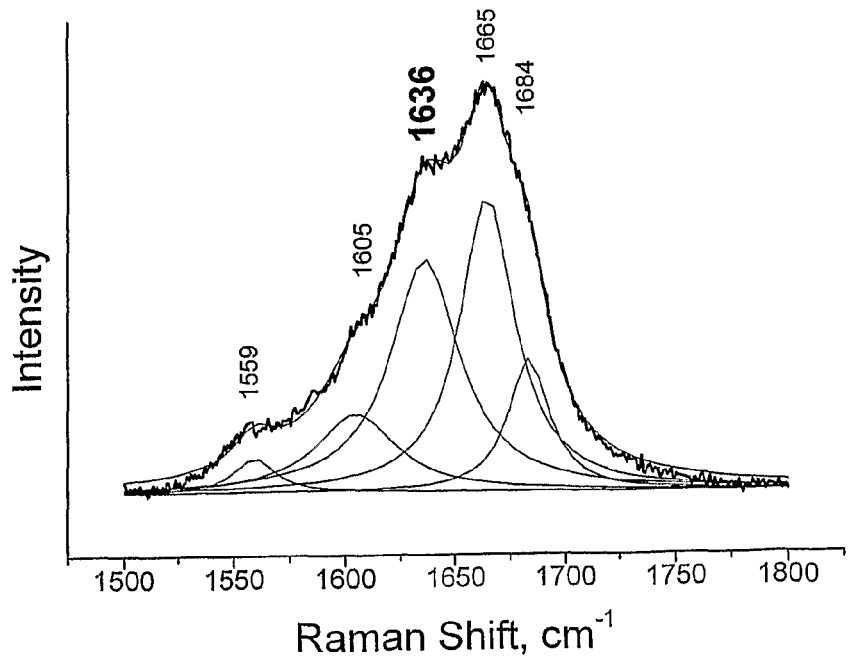
FIG. 8 shows a typical Raman spectrum of cartilage of Grade I showing the region 1,500 $cm^{-1}$ to 1,800 $cm^{-1}$ and how it has been deconstructed into five bands, the most important of which is the $H_2O$ bend band at about 1,637 $cm^{-1}$ (marked in bold).
Figure 9:
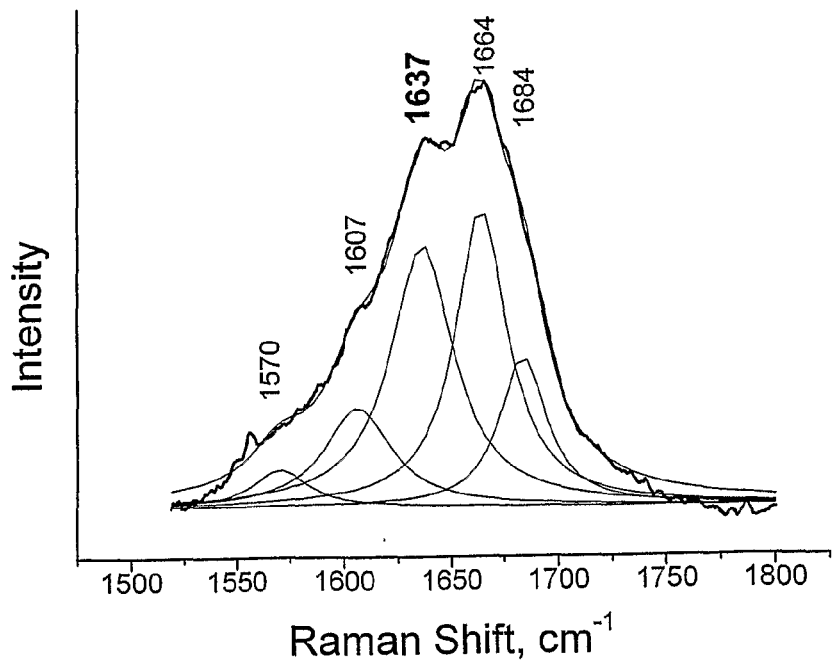
FIG. 9 shows a typical Raman spectrum of cartilage of Grade II showing the region 1,500 $cm^{-1}$ to 1,800 $cm^{-1}$ and how it has been deconstructed into five bands, the most important of which is the $H_2O$ bend band at about 1,637 $cm^{-1}$ (marked in bold).
Figure 10:
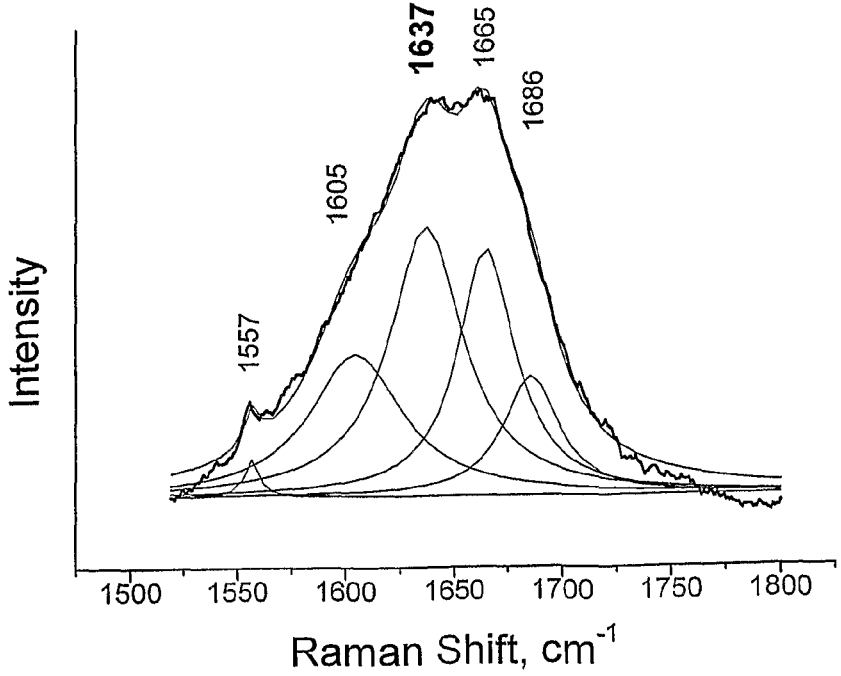
FIG. 10 shows a typical Raman spectrum of cartilage of Grade III showing the region 1,500 $cm^{-1}$ to 1,800 $cm^{-1}$ and how it has been deconstructed into five bands, the most important of which is the $H_2O$ bend band at about 1,637 $cm^{-1}$ (marked in bold).
Figure 11:
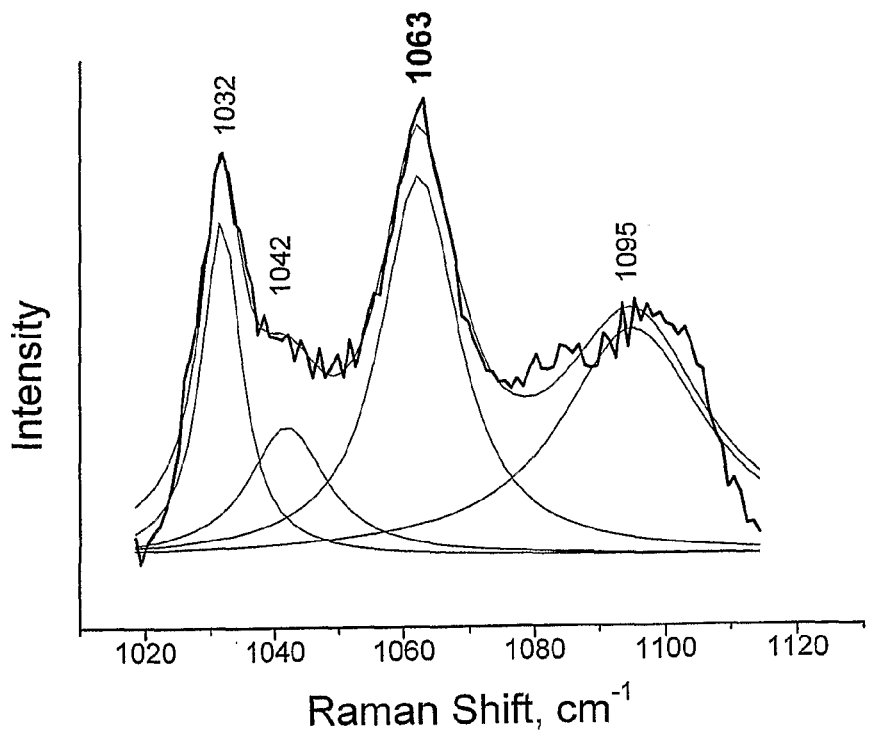
FIG. 11 shows a typical Raman spectrum of cartilage of Grade 0 showing the region 1,020 $cm^{-1}$ to 1,115 $cm^{-1}$ and how it has been deconstructed into four bands, the most important of which is the symmetric SO stretch of sulphate band at about 1,063 $cm^{-1}$ (marked in bold).
Figure 12:
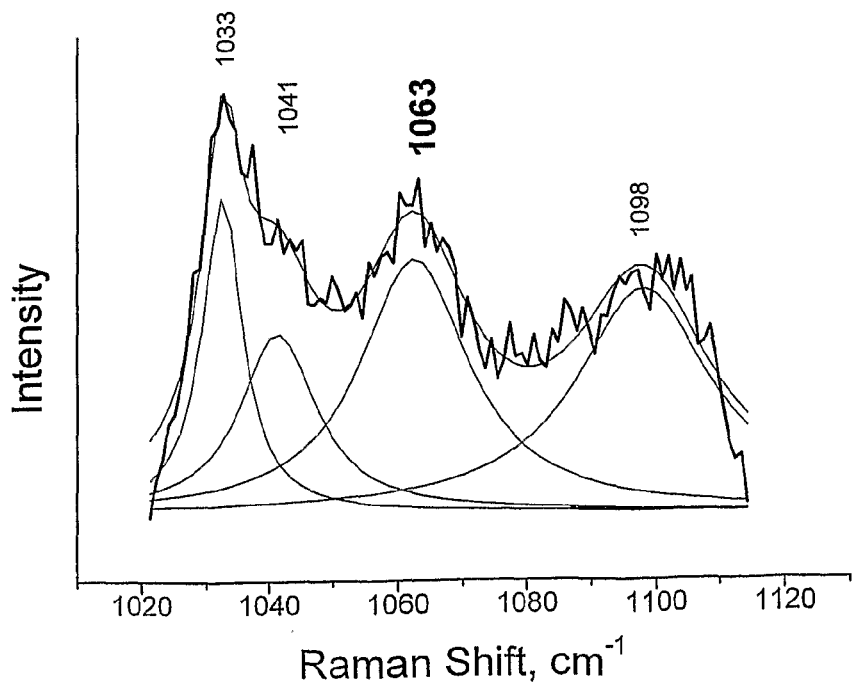
FIG. 12 shows a typical Raman spectrum of cartilage of Grade I showing the region 1,020 $cm^{-1}$ to 1,115 $cm^{-1}$ and how it has been deconstructed into four bands, the most important of which is the symmetric SO stretch of sulphate band at about 1,063 $cm^{-1}$ (marked in bold).
Figure 13:
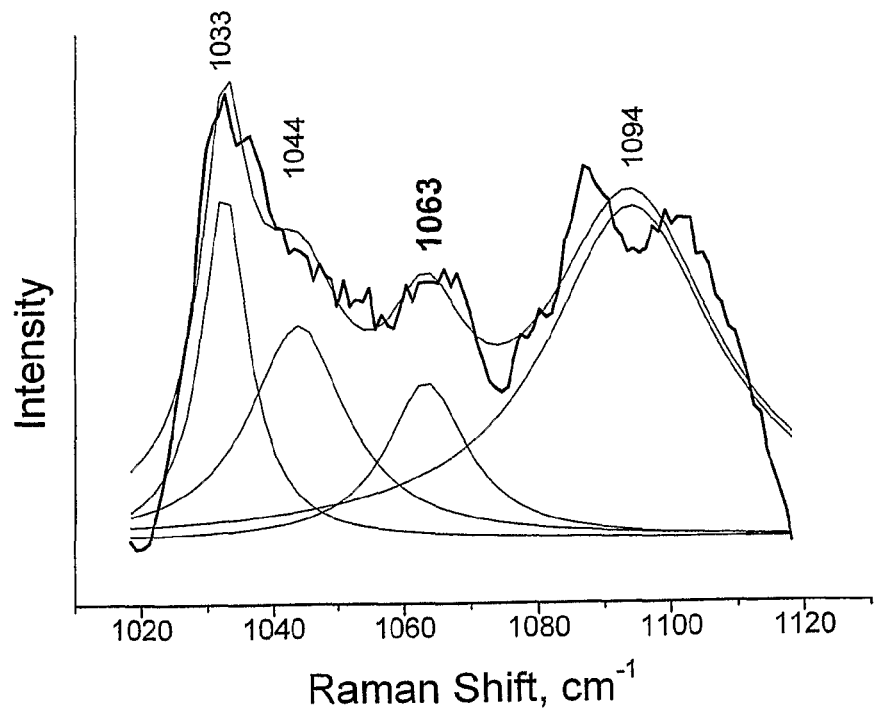
FIG. 13 shows a typical Raman spectrum of cartilage of Grade II showing the region 1,020 $cm^{-1}$ to 1,115 $cm^{-1}$ and how it has been deconstructed into four bands, the most important of which is the symmetric SO stretch of sulphate band at about 1,063 $cm^{-1}$ (marked in bold).
Figure 14:
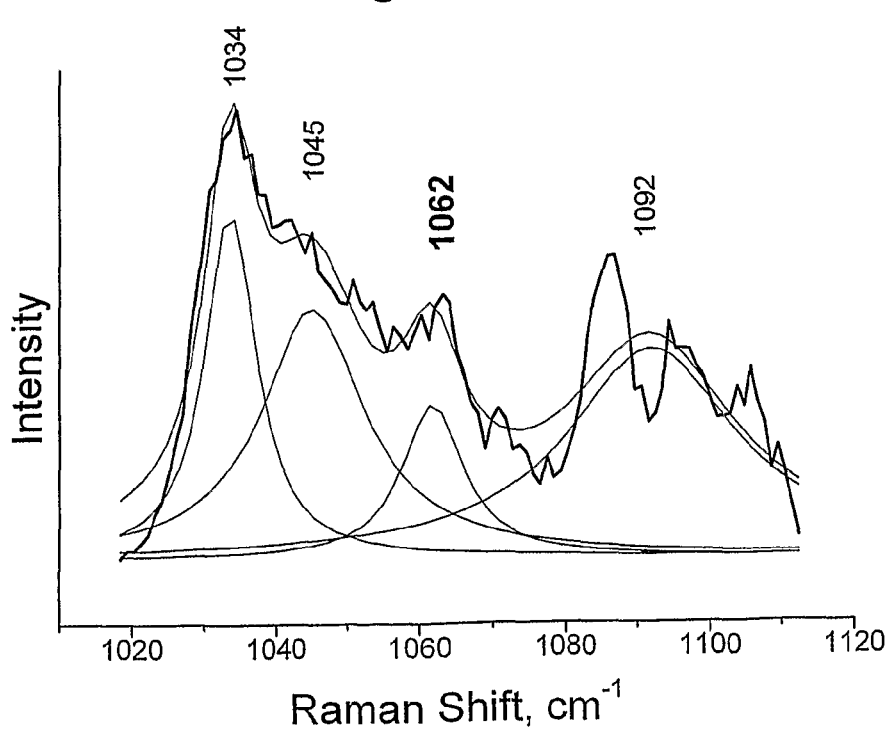
FIG. 14 shows a typical Raman spectrum of cartilage of Grade III showing the region 1,020 $cm^{-1}$ to 1,115 $cm^{-1}$ and how it has been deconstructed into four bands, the most important of which is the symmetric SO stretch of sulphate band at about 1,063 $cm^{-1}$ (marked in bold).
Figure 15:
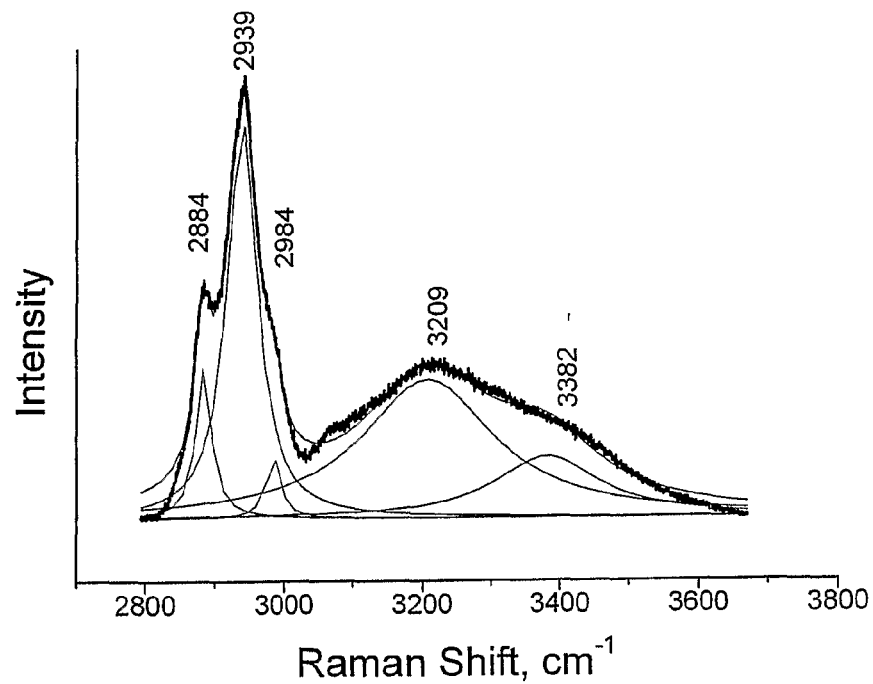
FIG. 15 shows a typical Raman spectrum of cartilage of Grade 0 showing the region 2,800 $cm^{-1}$ to 3,700 $cm^{-1}$ and how it has been deconstructed into five bands.
Figure 16:
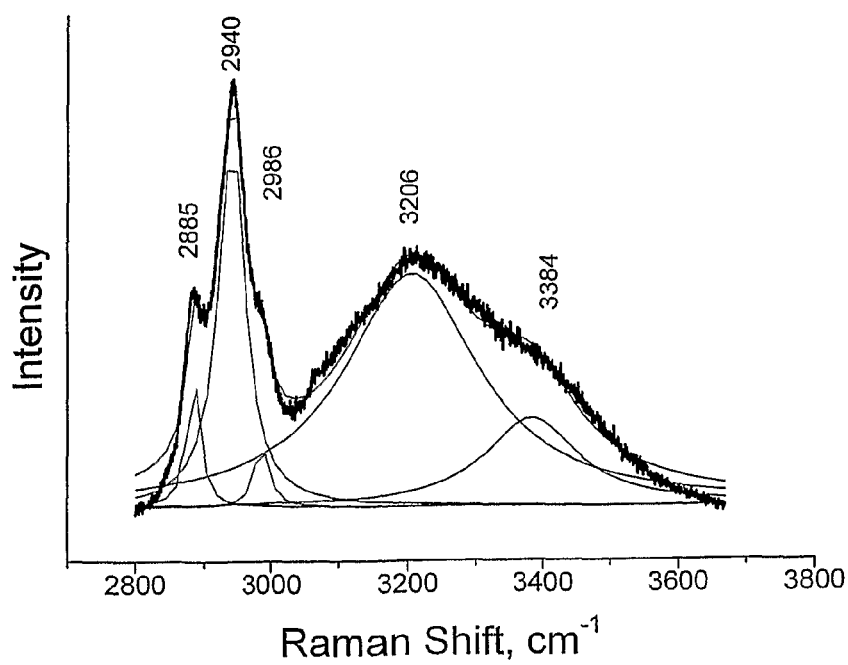
FIG. 16 shows a typical Raman spectrum of cartilage of Grade I showing the region 2,800 $cm^{-1}$ to 3,700 $cm^{-1}$ and how it has been deconstructed into five bands.
Figure 17:
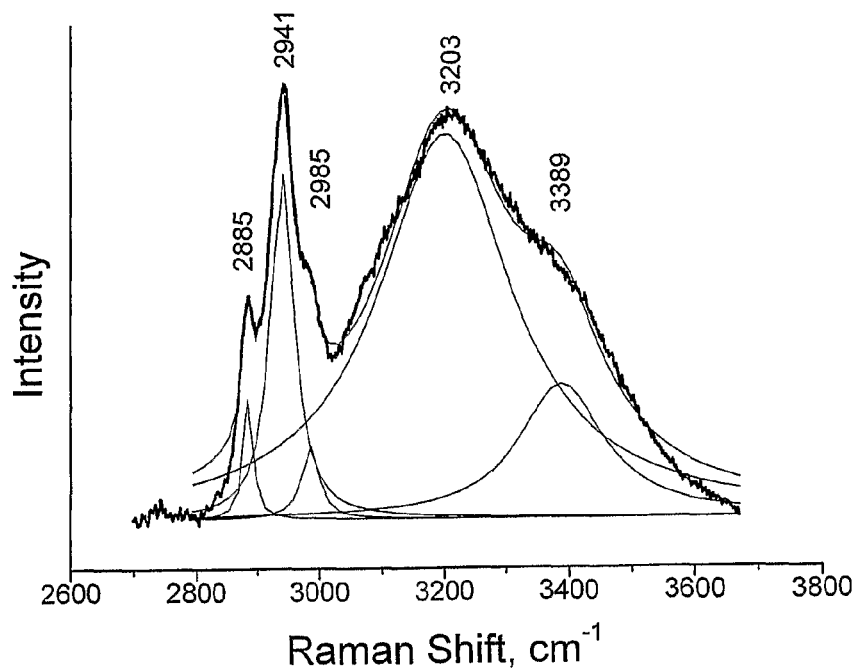
FIG. 17 shows a typical Raman spectrum of cartilage of Grade II showing the region 2,800 $cm^{-1}$ to 3,700 $cm^{-1}$ and how it has been deconstructed into five bands.
Figure 18:
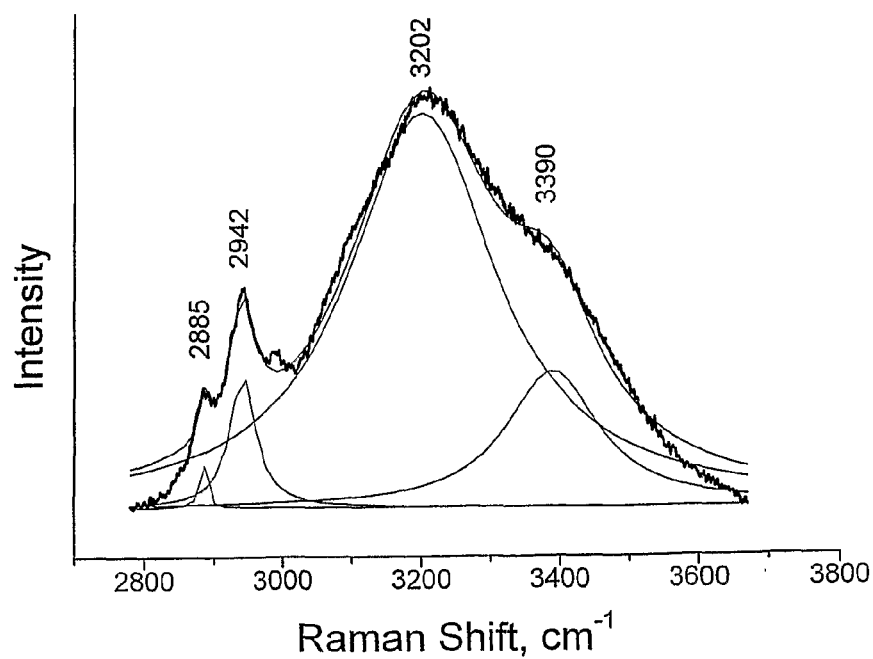
FIG. 18 shows a typical Raman spectrum of cartilage of Grade III showing the region 2,800 $cm^{-1}$ to 3,700 $cm^{-1}$ and how it has been deconstructed into four bands.
Figure 19:
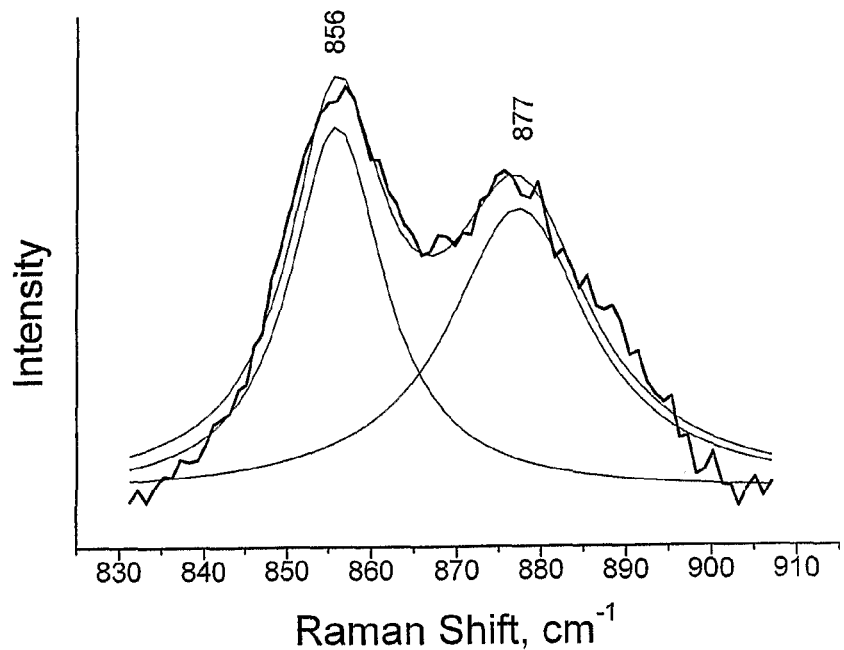
FIG. 19 shows a typical Raman spectrum of cartilage of Grade 0 showing the region 830 $cm^{-1}$ to 907 $cm^{-1}$ and how it has been deconstructed into two bands.
Figure 20:
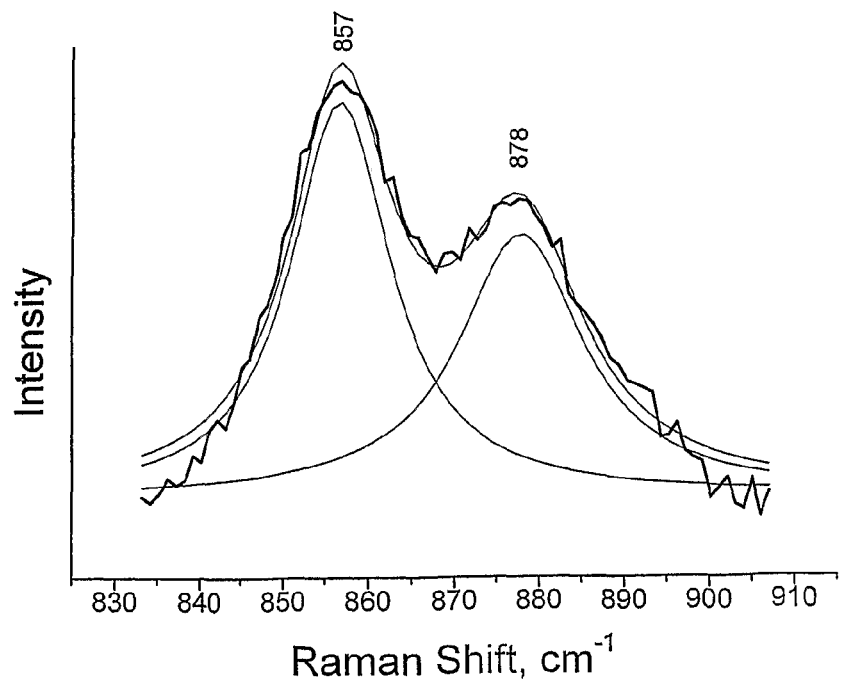
FIG. 20 shows a typical Raman spectrum of cartilage of Grade I showing the region 830 $cm^{-1}$ to 907 $cm^{-1}$ and how it has been deconstructed into two bands.
Figure 21:
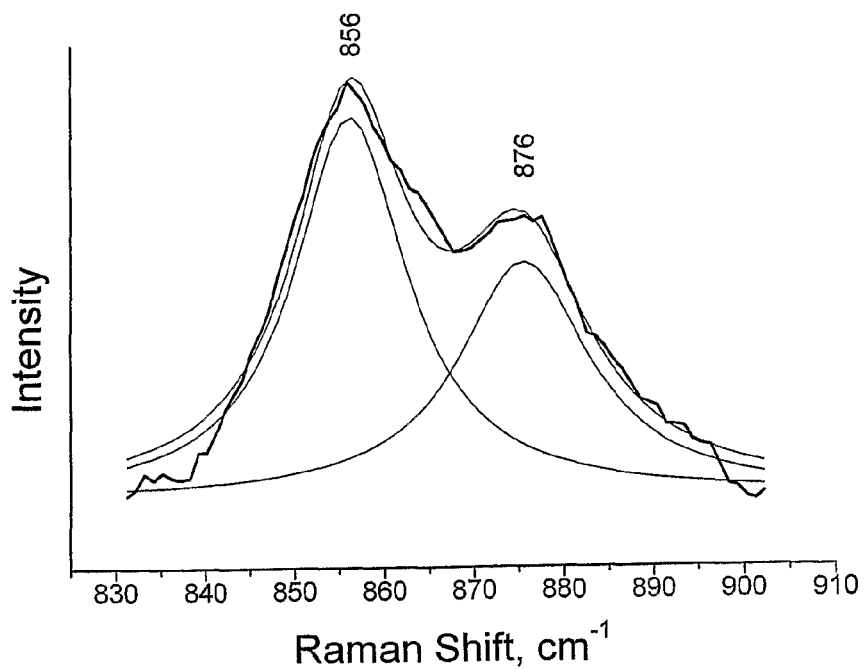
FIG. 21 shows a typical Raman spectrum of cartilage of Grade II showing the region 830 $cm^{-1}$ to 907 $cm^{-1}$ and how it has been deconstructed into two bands.
Figure 22:
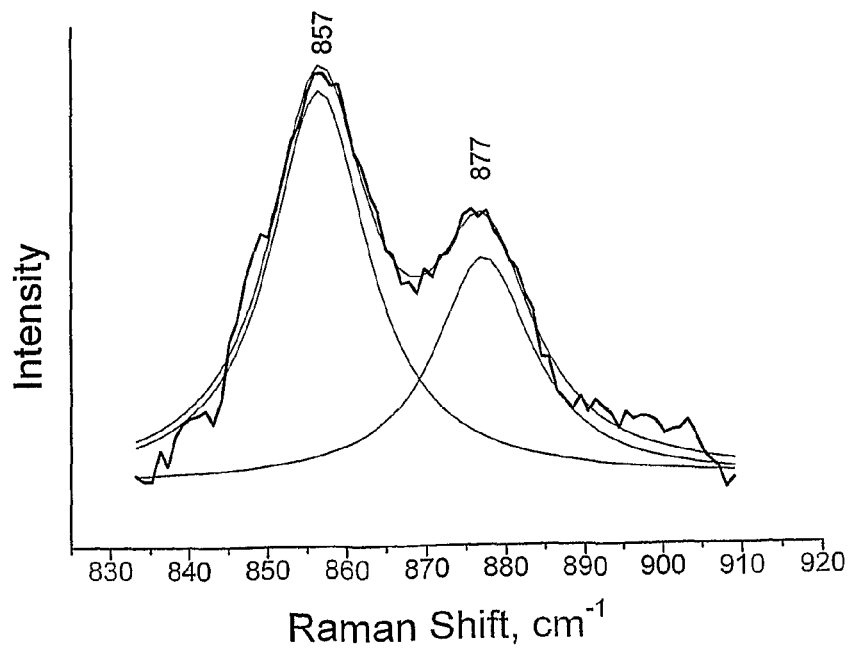
FIG. 22 shows a typical Raman spectrum of cartilage of Grade III showing the region 830 $cm^{-1}$ to 907 $cm^{-1}$ and how it has been deconstructed into two bands.

Both the band associated with proline at about 856 cm$^{-1}$, and the band associated with hydroxyproline at about 877 cm$^{-1}$ showed a significant reduction in band area with increasing cartilage degeneration, this reduction is seen in FIG. 3. However the area of the hydroxyproline band at 877 cm$^{-1}$ fell off faster. By analysing the band area ratio of proline to hydroxyproline it was found that there was a significant increase with higher grade of cartilage degeneration. There was a significant increase in the mean relative areas between the Grades 0 and I group and that of the Grades II and III group, FIG. 27b. When comparing the four groups a significant increase in the mean relative area was found between the Grade I and the Grade II groups, FIG. 27a. Both proline and hydroxyproline are important constituents of the collagen back bone. However, unlike proline, hydroxyproline is not present in the proteoglycans therefore this relative change in band area is commensurate with changes of the collagen fibrillar network relative to the cartilage proteoglycans.

In another experiment it was investigated whether or not the presence of spectral features associated with phosphate or carbonate within full thickness cartilage could be detected. The main phosphate $v_1$ band at about 960 cm$^{-1}$ is a striking feature of Raman spectra of bone tissue, being both tall and narrow, the other phosphate bands and the bands of carbonate are less prominent. Evidence of this band was searched for, as well as that of the other phosphate and carbonate bands, using samples of full thickness cartilage from Grade 0, and Grade I. We found no evidence of any band associated with either phosphate or carbonate, FIG. 33.

In another experiment it was investigated whether or not the presence of spectral features associated with phosphate and carbonate could be detected within a lesion in which a cartilage layer was present but deeply eroded i.e. showing greater cartilage erosion than that of samples in Grade III. In some samples that had been eroded to under 1 mm thickness some phosphate and carbonate spectral bands could be detect, with the most prominent band being the main phosphate $v_1$ band at about 960 cm$^{-1}$. This bony feature is sufficiently distinct and lies between the Raman spectral bands of cartilage that it would be noticeable in cartilage spectrum if it were present in any appreciable amount. None of the samples include in this study had any detectable signs of this phosphate $v_1$ band. It was only observed in the most eroded samples, FIG. 34, and those that were excluded from the rest of the experiments this study as being too eroded to included in the Grade III group. Any detectable evidence of phosphate or carbonate within a Raman spectrum of full thickness cartilage at the surface of a large joint, such as the knee or hip, of a mature large animal, such as a human, should, therefore, be taken as a sign of extreme cartilage erosion and degeneration.

In another experiment we measured the changes in spectra of Raman scattered photons at different depths through the cartilage from the synovial surface down to the subchondral bone. We took one sample from each of the Grade 0 and Grade I groups and measured spectra at four points along the cut face at right angles to the joint surface. Four points were chosen: joint surface, deep cartilage, mineralised cartilage and subchondral bone.

In the Raman spectra of the Grade 0 healthy cartilage, FIG. 35, it was seen that there was a prominent sulphate peak at about 1,063 cm$^{-1}$ in both the joint surface and the deep cartilage spectra. The bands associated with collagen and other organic molecules were more prominent in the deeper cartilage, while the low- and high-wavenumber bands of the O—H stretch complex at about 3,210 cm$^{-1}$ and 3,380 cm$^{-1}$ remained of similar intensity, which is consistent with the surface cartilage being slightly more hydrated than that of the deep cartilage. The subchondral bone exhibited a spectrum that is typical of bone. However, the mineralised cartilage layer exhibited an unusual and as yet unreported spectrum. While it showed both bony and cartilaginous features it has features that are not found in spectra of either bone or cartilage tissues. Some of the bands associated with organic moieties are sharper than comparable bands in spectra of normal bone or cartilage in that they are taller and narrower; these include the bands at about 537 cm$^{-1}$, 726 cm$^{-1}$, 1303 cm$^{-1}$, and the amide I band at about 1,656 cm$^{-1}$. This increase in sharpness of band suggests much higher levels of organisation at the molecular level than normal. Some of the bands have changed position, including the bands about phenylalanine ring breathing band at about 1,003 cm$^{-1}$ and the amide I band at about 1,665 cm$^{-1}$. Bands that are normally quite indistinct have become prominent including bands at about 1,745 cm$^{-1}$ and about 2,740 cm$^{-1}$. The low- and high-wavenumber bans of the O—H stretch complex at about 3,210 and about 3,380 cm$^{-1}$ have less area, implying that there is less water within this tissue layer than other layers. One of the most striking features of this spectrum is the change in shape of the CH stretch bands at about 2,889 cm$^{-1}$, 2,940 cm$^{-1}$ and 2,980 cm$^{-1}$. In bone and cartilage this appears as a group of about three bands with the tallest and most intense at about 2,940 cm$^{-1}$ with the other bands appearing as shoulders. In the spectrum of the mineralised cartilage layer the CH stretch bands have changed shape quite dramatically and have become much more like a plateau with an almost flat top from about 2,850 cm$^{-1}$ to about 2,940 cm$^{-1}$. These spectral features associated with the mineralised cartilage within a Raman spectrum of full thickness cartilage at the surface of a large joint, such as the knee or hip, of a mature large animal, such as a human, should, therefore, be taken as a sign of major cartilage erosion and degeneration.

In the Raman spectra of the Grade I cartilage, FIG. 36, it was seen that there was a prominent symmetric SO stretch of sulphate band at about 1,063 cm$^{-1}$ in both the joint surface and the deep cartilage spectra. This symmetric SO stretch of sulphate band is more prominent in the spectrum from the deep cartilage than the same band in the spectrum from the joint surface which is consistent with a loss of proteoglycans from the surface of the cartilage. This is a well reported phenomenon in full thickness cartilage harvested from joints with distinct lesions elsewhere within the joint (Bay-Jensen et al., 2007). This indicates that there will be benefit in recording spectra at different depths, this can be performed from the cartilage surface using known techniques (Draper et al., 2005, Matousek et al., 2006). The subchondral bone exhibited a spectrum that is typical of bone. While the mineralised cartilage layer exhibited a spectrum similar to that described above for the spectrum of the mineralised layer of the Grade 0 cartilage.

In another experiment we determined the level at which each measured parameter could be used to indicate degeneration within the cartilage sample being analysed. This used the same data as in the first experiment described above but looking at the individual measurements and deciding for each parameter the level at which some degeneration is indicated. This level was termed the "Indicator Level for Signs of Degeneration" or "Indicator Level" and varied for each parameter. The Indicator Levels are shown graphically in FIGS. 28, 29, 30, 31 and 32 are presented in tabular form in Table 2.

The Indicator Levels for each parameter were chosen to lie just beyond the healthy Grade 0 cartilage and is taken to be the level at which there are signs of degeneration. It can be seen from Table 2 that for each measured parameter most samples of Grades II and III were deemed to have signs of degeneration, but not all. Most of the samples of Grade I, however, were deemed not to have signs of degeneration when examining only one measured parameter.

If more than one parameter is used to assess each sample for signs of degeneration, the success rate at distinguishing signs in Grade I cartilage increase dramatically as can be seen in Table 3, with 71% of the Grade I showing signs of degradation when measured using at least one measured parameter. Furthermore, all samples of Grades II and III indicated signs of degeneration when using multiple parameters.

TABLE 2

Indicator Level for each measured parameter

| Spectral Parameter | Indicator Level for Signs of Degeneration | Number and percentage of samples of Grade 0 with Indicated Signs of Degeneration | Number and percentage of samples of Grade I with Indicated Signs of Degeneration | Number and percentage of samples of Grade II with Indicated Signs of Degeneration | Number and percentage of samples of Grade III with Indicated Signs of Degeneration |
|---|---|---|---|---|---|
| Ratio of areas of band at about 856 cm$^{-1}$ to band at about 877 cm$^{-1}$ | Greater than 1.5 indicates degeneration | 0 0% | 6 43% | 4 100% | 7 88% |
| Ratio of areas of band at about 1063 cm$^{-1}$ to band at about 1003 cm$^{-1}$ | Less than 1 indicates degeneration | 0 0% | 6 43% | 4 100% | 8 100% |
| Ratio of areas of band at about 1637 cm$^{-1}$ to band at about 1003 cm$^{-1}$ | Greater than 10 indicates degeneration | 0 0% | 3 21% | 3 75% | 5 63% |
| Ratio of areas of band at about 3210 cm$^{-1}$ to band at about 2940 cm$^{-1}$ | Greater than 4 indicates degeneration | 0 0% | 0 0% | 4 100% | 8 100% |
| Ratio of areas of band at about 3210 cm$^{-1}$ to band at about 3380 cm$^{-1}$ | Greater than 3.7 indicates degeneration | 0 0% | 3 21% | 4 100% | 8 100% |

TABLE 3

The number of times an individual sample was deemed to have signs of degeneration by cartilage grade.

| Number of measured spectral parameter that deemed an individual sample signs of degeneration | Number and percentage of samples of Grade 0 with Indicated Signs of Degeneration | Number and percentage of samples of Grade I with Indicated Signs of Degeneration | Number and percentage of samples of Grade II with Indicated Signs of Degeneration | Number and percentage of samples of Grade III with Indicated Signs of Degeneration |
|---|---|---|---|---|
| 1 or more | 0 0% | 10 71% | 4 100% | 8 100% |
| 2 or more | 0 0% | 6 43% | 4 100% | 8 100% |
| 3 or more | 0 0% | 2 14% | 4 100% | 8 100% |
| 4 or 5 | 0 0% | 1 7% | 4 100% | 8 100% |

TABLE 3-continued

The number of times an individual sample was deemed to have signs of degeneration by cartilage grade.

| Number of measured spectral parameter that deemed an individual sample signs of degeneration | Number and percentage of samples of Grade 0 with Indicated Signs of Degeneration | Number and percentage of samples of Grade I with Indicated Signs of Degeneration | Number and percentage of samples of Grade II with Indicated Signs of Degeneration | Number and percentage of samples of Grade III with Indicated Signs of Degeneration |
|---|---|---|---|---|
| All 5 | 0 0% | 0 0% | 2 50% | 5 63% |

REFERENCES

The Handbook of Vibrational Spectroscopy. John Wiley and Son, Chichester, 2002.

Bansil, R., I. V. Yannas, and H. E. Stanley. 1978. Raman spectroscopy: a structural probe of glycosaminoglycans. *Biochim. Biophys. Acta* 541:535-542.

Bay-Jensen, A C., T. L. Andersen, T. N, Charni-Ben, P. W. Kristensen, P. Kjaersgaard-Andersen, L. Sandell, P. Garnero, and J. M. Delaisse. 2007. Biochemical markers of type II collagen breakdown and synthesis are positioned at specific sites in human osteoarthritic knee cartilage. *Osteoarthritis. Cartilage.*

Brandt, K. D. 1998. The importance of nonpharmacologic approaches in management of osteoarthritis. *Am. J. Med.* 105:39 S-44S.

Cabassi, F., B. Casu, and A. S. Perlin. 1978. Infrared-Absorption and Raman-Scattering of Sulfate Groups of Heparin and Related Glycosaminoglycans in Aqueous-Solution. *Carbohydrate Research* 63:1-11, Camacho, N. P., P. Carroll, and C. L. Raggio. 2003. Fourier transform infrared imaging spectroscopy (FT-IRIS) of mineralization in bisphosphonate-treated oim/oim mice. *Calcif. Tissue Int.* 72:604-609.

Camacho, N. P., P. West, P. A. Torzilli, and R. Mendelsohn. 2001. FTIR microscopic imaging of collagen and proteoglycan in bovine cartilage. *Biopolymers* 62:1-8.

Carden, A. and M. D. Morris. 2000. Application of vibrational spectroscopy to the study of mineralized tissues (review). *J. Biomed. Opt.* 5:259-268.

Clarke, S., C. Wakeley, J. Duddy, M. Sharif, I. Waft, K. Ellingham, C. J. Elson, G. Nickols, and J. R. Kirwan. 2004. Dual-energy X-ray absorptiometry applied to the assessment of tibial subchondral bone mineral density in osteoarthritis of the knee. *Skeletal. Radiol.* 33:588-595.

D'Ambrosia, R. D. 2005. Epidemiology of osteoarthritis. *Orthopedics* 28:s201-s205.

Davis, C R., J. Karl, R. Granell, J. R. Kirwan, J. Fasham, J. Johansen, P. Garnero, and M. Sharif. 2007. Can biochemical markers serve as surrogates for imaging in knee osteoarthritis? *Arthritis Rheum.* 56:4038-4047.

F. de Groot. 2001. High resolution X-ray emission and X-ray absorption spectroscopy. *Chemical Reviews* 101: 1779-1808

Dehring, K. A., N. J. Crane, A. R. Smukler, J. B. McHugh, B. J. Roessler, and M. D. Morris. 2006a. Identifying chemical changes in subchondral bone taken from murine knee joints using raman spectroscopy. *Applied Spectroscopy* 60:1134-1141.

Dehring, K A., A. R. Smukler, B. J. Roessler, and M. D. Morris. 2006b. Correlating changes in collagen secondary structure with aging and defective type II collagen by Raman spectroscopy. *Applied Spectroscopy* 60:366-372.

Draper, E. R. C., M. D. Morris, N. P. Camacho, P. Matousek, M. Towrie, A. W. Parker, and A. E. Goodship. 2005. Novel assessment of bone using time-resolved transcutaneous Raman spectroscopy. *J. Bone Miner. Res.* 20:1968-1972.

Felson, D. T., R. C. Lawrence, P. A. Dieppe, R. Hirsch, C. G. Helmick, J. M. Jordan, R. S. Kington, N. E. Lane, M. C. Nevitt, Y. Zhang, M. Sowers, T. McAlindon, T. D. Spector, A. R. Poole, S. Z. Yanovski, G. Ateshian, L. Sharma, J. A. Buckwalter, K. D. Brandt, and J. F. Fries. 2000. Osteoarthritis: new insights. Part 1: the disease and its risk factors. *Ann. Intern. Med.* 133:635-646.

Ferry, A. and P. Jacobsson. 1995. Curve-Fitting and Deconvolution of Instrumental Broadening—A Simulated Annealing Approach. *Applied Spectroscopy* 49:273-278.

Garnero, P., W. S. Aronstein, S. B. Cohen, P. G. Conaghan, G. A. Cline, C. Christiansen, J. F. Beary, J. M. Meyer, and C. O. Bingham, III. 2007. Relationships between biochemical markers of bone and cartilage degradation with radiological progression in patients with knee osteoarthritis receiving risedronate: the Knee Osteoarthritis Structural Arthritis randomized clinical trial. *Osteoarthritis. Cartilage.*

Garnero, P., B. Mazieres, A. Gueguen, M. Abbal, L. Berdah, M. Lequesne, M. Nguyen, J. P. Salles, E. Vignon, and M. Dougados. 2005. Cross-sectional association of 10 molecular markers of bone, cartilage, and synovium with disease activity and radiological joint damage in patients with hip osteoarthritis: the ECHODIAH cohort. *J. Rheumatol.* 32:697-703.

Gray, M. L., Burstein, D., Kim, Y. J., Maroudas, A., (2008). 2007 Elizabeth Winston Lanier Award Winner. Magnetic resonance imaging of cartilage glycosaminoglycan: basic principles, imaging technique, and clinical applications. *J. Orthop. Res* 26, 281-291.

Hendra, P. J., C. Jones, and G. Warnes. 1991. Fourier Transform Raman Spectroscopy. Ellis Harwood, N.Y.

Henrotin, Y., S. Addison, V. Kraus, and M. Deberg. 2007. Type II collagen markers in osteoarthritis: what do they indicate? *Curr. Opin. Rheumatol.* 19:444-450.

Hunziker, E. B. 2002. Articular cartilage repair: basic science and clinical progress. A review of the current status and prospects. *Osteoarthritis. Cartilage.* 10:432-463.

Kaminaka, S., T. Ito, H. Yamazaki, E. Kohda, and H. Hamaguchi. 2002. Near-infrared multichannel Raman spectroscopy toward real-time in vivo cancer diagnosis. *Journal of Raman Spectroscopy* 33:498-502.

Kellgren, J. H. and J. S. Lawrence. 1957. Radiological assessment of osteoarthrosis. *Ann. Rheum. Dis.* 16:494-502.

Koljenovic, S., T. C. Bakker Schut, J. P. van Meerbeeck, A. P. W. M. Maat, S. A. Burgers, P. E. Zondervan, J. M. Kros, and G. J. Puppels. 2004. Raman microspectroscopic mapping studies of human bronchial tissue. *J. Biomed. Opt.* 9:1187-1197.

Lambert, P. J., A. G. Whitman, O. F. Dyson, and S. M. Akula. 2006. Raman spectroscopy: the gateway into tomorrow's virology. *Virol. J.* 3:51.

Landewe, R. and H. D. Van Der. 2005. Presentation and analysis of radiographic data in clinical trials and observational studies. *Ann. Rheum. Dis.* 64 Suppl 4:iv48-iv51.

Lawrence, R. C., M. C. Hochberg, J. L. Kelsey, F. C. McDuffie, T. A. Medsger, Jr., W. R. Felts, and L. E. Shulman. 1989. Estimates of the prevalence of selected arthritic and musculoskeletal diseases in the United States. *J. Rheumatol.* 16:427-441.

Long, D. A. 2002. The Raman Effect. John Wiley and Sons, New York.

Lyng, F. M., E. O. Faolain, J. Conroy, A. D. Meade, P. Knief, B. Duffy, M. B. Hunter, J. M. Byrne, P. Kelehan, and H. J. Byrne. 2007. Vibrational spectroscopy for cervical cancer pathology, from biochemical analysis to diagnostic tool. *Exp. Mol. Pathol.*

Ma, L, Z. Ahmed, A. V. Mikhonin, and S. A. Asher. 2007. UV resonance raman measurements of poly-L-lysine's conformational energy landscapes: Dependence on perchlorate concentration and temperature. *Journal of Physical Chemistry B* 111:7675-7680.

Matousek, P., I. P. Clark, M. Towrie, A. W. Parker, E. R. C. Draper, A. E. Goodship, M. D. Morris, W. F. Finney, and N. Everall. 2005. Subsurface probing in diffusely scattering media using spatially offset Raman spectroscopys. *Applied Spectroscopy* 59:393-400.

Matousek, P., E. R. C. Draper, A. E. Goodship, I. P. Clark, K. L. Ronayne, and A. W. Parker. 2006. Noninvasive Raman spectroscopy of human tissue in vivo. *Appl. Spectrosc.* 60:758-763.

Mayer-Kuckuk, P. and A. L. Boskey. 2006. Molecular imaging promotes progress in orthopedic research. *Bone* 39:965-977.

McCreadie, B. R., M. D. Morris, T. Chen, D. Sudhaker Rao, W. F. Finney, E. Widjaja, and S. A. Goldstein. 2006. Bone tissue compositional differences in women with and without osteoporotic fracture. *Bone* 39:1190-1195.

Meziane-Tani, M., P. Lagant, A. Semmoud, and G. Vergoten. 2006. The SPASIBA force field for chondroitin sulfate: Vibrational analysis of D-glucuronic and N-acetyl-D-galactosamine 4-sulfate sodium salts. *Journal of Physical Chemistry A* 110:11359-11370.

Mizuno, A., M. Tsuji, K. Fujii, K. Kawauchi, and Y. Ozaki. 1994. Near-infrared Fourier transform Raman spectroscopic study of cornea and sclera. *Jpn. J. Ophthalmol.* 38:44-48.

Morris, M. D., A. Berger, and A. Mahadevan-Jansen. 2005. Special section guest editorial: Infrared and Raman spectroscopy. *J. Biomed. Opt* 10:1.

Motz, J. T., S. J. Gandhi, O. R. Scepanovic, A. S. Haka, J. R. Kramer, R. R. Dasari, and M. S. Feld. 2005. Real-time Raman system for in vivo disease diagnosis. *J. Biomed. Opt* 10:1-7.

Palmer, A. W., Guldberg, R. E., Levenston, M. E., (2006). Analysis of cartilage matrix fixed charge density and three-dimensional morphology via contrast-enhanced micro-computed tomography. *Proc. Natl. Acad. Sci. U.S.A.* 103, 19255-19260.

Pelletier, J. P., J. P. Caron, C. Evans, P. D. Robbins, H. I. Georgescu, D. Jovanovic, J. C. Fernandes, and J. Martel-Pelletier. 1997. In vivo suppression of early experimental osteoarthritis by interleukin-1 receptor antagonist using gene therapy. *Arthritis Rheum.* 40:1012-1019.

Poole, A. R. 1999. An introduction to the pathophysiology of osteoarthritis. *Front. Biosci.* 4:D662-D670.

Spahn, G.; Plettenberg, H.; Kahl, E.; Klinger, H. M.; Muckley, T.; Hofmann, G. O. 2007 Near-infrared (NIR) spectroscopy. A new method for arthroscopic evaluation of low grade degenerated cartilage lesions. Results of a pilot study BMC. *Musculoskelet. Disord.* 8:47

Spahn, G.; Plettenberg, H.; Nagel, H.; Kahl, E.; Klinger, H. M.; Muckley, T.; Gunther, M.; Hofmann, G. O.; Mollenhauer, J. A. 2008 Evaluation of cartilage defects with near-infrared spectroscopy (NIR): An ex vivo study. *Med. Eng. Phys.* 30:285-292

Takahashi, M., K. Naito, M. Abe, T. Sawada, and A. Nagano. 2004. Relationship between radiographic grading of osteoarthritis and the biochemical markers for arthritis in knee osteoarthritis. *Arthritis Res. Ther.* 6:R208-R212.

Tobin, M. G. 1971. Laser Raman Spectroscopy. Wiley-Interscience, New York.

Vickers, T. J., R. E. Wambles, and C. K. Mann. 2001. Curve fitting and linearity: Data processing in Raman spectroscopy. *Applied Spectroscopy* 55:389-393.

Yeni, Y. N., J. Yerramshetty, O. Akkus, C. Pechey, and C. M. Les. 2006. Effect of fixation and embedding on Raman spectroscopic analysis of bone tissue. *Calcified Tissue International* 78:363-371.

The invention claimed is:

1. A method of aiding in the diagnosis or prediction of degenerative joint disease (DJD) in a joint of a patient, the method comprising:

obtaining a test spectrum of Raman scattered radiation from cartilage tissue in the joint; and analyzing the test spectrum, or one or more regions thereof, to assess whether the test spectrum is consistent with the patient having, or subsequently developing, DJD in the joint, wherein the analyzing step comprises:

comparing the tests spectrum or the one or more regions thereof to a standard spectrum of Raman scattered radiation or to one or more respective regions thereof, and wherein the analyzing step further comprises comparing a combination of the following from the test spectrum to the corresponding area, position and/or from the standard spectrum:

(a) the area and position of the proline band at about 856 $cm^{-1}$;

(b) the area and position of the hydroxyproline band at about 877 $cm^{-1}$;

(c) the area and position of the phenylalanine ring breathing band at about 1,003 $cm^{-1}$;

(d) the area and position of the symmetric SO stretch of the sulphate band at about 1,063 $cm^{-1}$;

(e) the area and position of the band due to amide III at about 1,272 $cm^{-1}$;

(f) the area and position of the band due to $H_2O$ bend at about 1,637 $cm^{-1}$;

(g) the area and position of the band due to amide I at about 1,665 $cm^{-1}$;

(h) the area and position of the CH stretch band at about 2,940 $cm^{-1}$;

(i) the area and position of the low-wavenumber band of the O—H stretch complex at about 3,210 $cm^{-1}$;

(j) the area and position of the high-wavenumber band of the O—H stretch complex at about 3,380 $cm^{-1}$;

(k) the ratio of the area of the band due to $H_2O$ bend at about 1,637 $cm^{-1}$ to the area of the phenylalanine ring breathing band at about 1,003 $cm^{-1}$;

(l) the ratio of the area of the low-wavenumber band of the O—H stretch complex at about 3,210 $cm^{-1}$ to the area of the CH stretch at about 2,940 $cm^{-1}$;

(m) the ratio of the area of the symmetric SO stretch of the sulphate band at about 1,063 $cm^{-1}$ to the area of the phenylalanine ring breathing band at about 1,003 $cm^{-1}$;

(n) the ratio of the area of the low-wavenumber band of the O—H stretch complex at about 3,210 cm$^{-1}$ to the area of the high-wavenumber band of the O—H stretch complex at about 3,380 cm$^{-1}$; and (o) the ratio of the area of the proline band at about 856 cm$^{-1}$ to the area of the hydroxyproline band at about 877 cm$^{-1}$;

and further wherein either (l) and (m); (d), (l) and (m); (l), (m), and (o); (d), (l), (m) and (o); (l), (m) and (n); (d), (l), (m) and (n); or (o), (d), (l), (m) and (n) from the test spectrum are compared to the corresponding area, position and/or ratios from the standard spectrum.

2. The method of claim 1 wherein the obtaining step comprises determining the area, height, width or position (mean wavenumber) of one or more bands from the test spectrum, or the one or more regions thereof.

3. A method according to claim 2 wherein the obtaining step comprises:
determining, or being provided with, any one, two, three, four, five, six, seven, eight, nine, or all ten of (a), (b), (c), (d), (e), (f), (g), (h), (i), and (j).

4. A method according to claim 1 wherein the obtaining step comprises determining a ratio of the area, height or width of at least two bands from the test spectrum, or the one or more regions thereof.

5. A method according to claim 4 wherein the obtaining step comprises:
determining, or being provided with, any one, two, three, four, or all five of (k), (l), (m), (n), and (o).

6. A method according to claim 1 further comprising comparing the intensity of at least one of a carbonate, phosphate or CH$_2$ wag band in the test spectrum with the corresponding intensity in the standard spectrum.

7. A method of aiding in the diagnosis or prediction of degenerative joint disease (DJD) in a joint of a patient, the method comprising:
obtaining a test spectrum of Raman scattered radiation from cartilage tissue in the joint; and
analyzing the test spectrum, or one or more regions thereof, to assess whether the test spectrum is consistent with the patient having, or subsequently developing, DJD in the joint;
wherein the obtaining step comprises determining the area, height, width, or position (mean wavenumber) of one or more bands from the test spectrum, or the one or more regions thereof;
and further wherein the analyzing step comprises comparing the area or height of one or more bands from the test spectrum, or the ratio of the area or height of at least two bands from the test spectrum, with a predetermined numerical indicator levels, wherein the indicator levels are indicative of the presence of DJD in the cartilage of the joint;
and further wherein any one, two, three, four, or all five of:
the ratio of the area of the band due to H$_2$O bend at about 1,637 cm$^{-1}$ to the area of the phenylalanine ring breathing band at about 1,003 cm$^{-1}$;
the ratio of the area of the low-wavenumber band of the O—H stretch complex at about 3,210 cm$^{-1}$ to the area of the CH stretch at about 2,940 cm$^{-1}$;
the ratio of the area of the symmetric SO stretch of the sulphate band at about 1,063 cm$^{-1}$ to the area of the phenylalanine ring breathing band at about 1,003 cm$^{-1}$;
the ratio of the area of the low-wavenumber band of the O—H stretch complex at about 3,210 cm$^{-1}$ to the area of the high-wavenumber band of the O—H stretch complex at about 3,380 cm$^{-1}$; and
the ratio of the area of the proline band at about 856 cm$^{-1}$ to the area of the hydroxyproline band at about 877 cm$^{-1}$;
are compared with respective indicator levels that are indicative of the presence of DJD in the cartilage of the joint
and further wherein the indicator levels are:
a ratio of the area of the H$_2$O bend band at about 1,637 cm$^{-1}$ to the area of the phenylalanine ring breathing band at about 1,003 cm$^{-1}$ of >10;
a ratio of the area of the low-wavenumber band of the O—H stretch complex at about 3,210 cm$^{-1}$ to the area of the CH stretch at about 2,940 cm$^{-1}$ of >4;
a ratio of the area of the symmetric SO stretch of the sulphate band at about 1,063 cm$^{-1}$ to the area of the phenylalanine ring breathing band at about 1,003 cm$^{-1}$ of <1;
a ratio of the area of the low-wavenumber band of the O—H stretch complex at about 3,210 cm$^{-1}$ to the area of the high-wavenumber band of the O—H stretch complex at about 3,380 cm$^{-1}$ of >3.7; and
a ratio of the area of the proline band at about 856 cm$^{-1}$ to the area of the hydroxyproline band at about 877 cm$^{-1}$ of >1.5.

8. A method according to claim 7 wherein the analysing step comprises comparing a plurality of ratios of the area of a corresponding plurality of pairs of bands from the test spectrum with respective numerical indicator levels.

9. An apparatus for aiding in the diagnosis of prediction of degenerative joint disease (DJD) in a joint of a patient, the apparatus comprising:
a light source and transmitter;
a detector configured to receive Raman scattered radiation from a portion of the cartilage tissue in the joint illuminated by the light source; and
an analyser coupled to the detector and configured to:
obtain a test spectrum of Raman scattered radiation from the cartilage tissue in the joint by determining the area, height, width, or position (mean wavenumber) of one or more bands from the test spectrum, or one or more regions thereof, or by determining a ratio of the area, height, or width of at least two bands from the test spectrum, or the one or more regions thereof;
analyse the test spectrum, or one or more regions thereof, by comparing the test spectrum or the one or more regions thereof to a standard spectrum of Raman scattered radiation or to one or more respective regions thereof; and
wherein the analyser is configured to compare a combinations of the following from the test spectrum to the corresponding area, position and/or ratio from the standard spectrum:
(a) the area and position of the proline band at about 856 cm$^{-1}$;
(b) the area and position of the hydroxyproline band at about 877 cm$^{-1}$;
(c) the area and position of the phenylalanine ring breathing band at about 1,003 cm$^{-1}$;
(d) the area and position of the symmetric SO stretch of the sulphate band at about 1,063 cm$^{-1}$;
(e) the area and position of the band due to amide III at about 1,272 cm$^{-1}$;
(f) the area and position of the band due to H$_2$O bend at about 1,637 cm$^{-1}$;
(g) the area and position of the band due to amide I at about 1,665 cm$^{-1}$;

(h) the area and position of the CH stretch band at about 2,940 cm$^{-1}$;
(i) the area and position of the low-wavenumber band of the O—H stretch complex at about 3,210 cm$^{-1}$; and
(j) the area and position of the high-wavenumber band of the O—H stretch complex at about 3,380 cm$^{-1}$;
(k) the ratio of the area of the band due to H$_2$O bend at about 1,637 cm$^{-1}$ to the area of the phenylalanine ring breathing band at about 1,003 cm$^{-1}$;
(l) the ratio of the area of the low-wavenumber band of the O—H stretch complex at about 3,210 cm$^{-1}$ to the area of the CH stretch at about 2,940 cm$^{-1}$;
(m) the ratio of the area of the symmetric SO stretch of the sulphate band at about 1,063 cm$^{-1}$ to the area of the phenylalanine ring breathing band at about 1,003 cm$^{-1}$;
(n) the ratio of the area of the low-wavenumber band of the O—H stretch complex at about 3,210 cm$^{-1}$ to the area of the high-wavenumber band of the O—H stretch complex at about 3,380 cm$^{-1}$; and
(o) the ratio of the area of the proline band at about 856 cm$^{-1}$ to the area of the hydroxyproline band at about 877 cm$^{-1}$;
and further wherein the analyser is configured to compare a combination of either (l) and (m); (d), (l) and (m); (l), (m), and (o); (d), (l), (m) and (o); (l), (m) and (n); (d), (l), (m) and (n); or (o), (d), (l), (m) and (n) from the test spectrum to the corresponding area, position and/or ratios from the standard spectrum.

10. Apparatus according to claim 9 wherein the transmitter and the detector further comprise a position sensor.

11. A method according to claim 1, further comprising treating the DJD, thereby combating DJD in the joint of the patient.

12. An apparatus for aiding in the diagnosis or prediction of degenerative joint disease (DJD) in a joint of a patient, the apparatus comprising:
a light source and transmitter;
a detector configured to receive Raman scattered radiation from a portion of the cartilage tissue in the joint illuminated by the light source; and
an analyser coupled to the detector and configured to:
obtain a test spectrum of Raman scattered radiation from the cartilage tissue in the joint by determining the area, height, width, or position (mean wavenumber) of one or more bands from the test spectrum, or one or more regions thereof, or by determining a ratio of the area, height, or width of at least two bands from the test spectrum, or the one or more regions thereof; and
analyse the test spectrum, or one or more regions thereof, by comparing the test spectrum or the one or more regions thereof to a standard spectrum of Raman scattered radiation or to one or more respctive regions thereof; and
wherein the analyser is configured to compare the area or height of one or more bands from the test spectrum, or the ratio of the area or height of at least two bands from the test spectrum, with a predetermined numerical indicator levels, wherein the indicator levels are indicative of the presence of DJD in the cartilage of the joint;
and further wherein the analyser is configured to compare any one, two, three, four, or all five of:
the ratio of the area of the band due to H$_2$O bend at about 1,637 cm$^{-1}$ to the area of the phenylalanine ring breathing band at about 1,003 cm$^{-1}$;
the ratio of the area of the low-wavenumber band of the O—H stretch complex at about 3,210 cm$^{-1}$ to the area of the CH stretch at about 2,940 cm$^{-1}$;
the ratio of the area of the symmetric SO stretch of the sulphate band at about 1,063 cm$^{-1}$ to the area of the phenylalanine ring breathing band at about 1,003 cm$^{-1}$;
the ratio of the area of the low-wavenumber band of the O—H stretch complex at about 3,210 cm$^{-1}$ to the area of the high-wavenumber band of the O—H stretch complex at about 3,380 cm$^{-1}$; and
the ratio of the area of the proline band at about 856 cm$^{-1}$ to the area of the hydroxyproline band at about 877 cm$^{-1}$;
with respective indicator levels that are indicative of the presence of DJD in the cartilage of the joint
and further wherein the indicator levels are:
a ratio of the area of the H$_2$O bend band at about 1,637 cm$^{-1}$ to the area of the phenylalanine ring breathing band at about 1,003 cm$^{-1}$ of >10;
a ratio of the area of the low-wavenumber band of the O—H stretch complex at about 3,210 cm$^{-1}$ to the area of the CH stretch at about 2,940 cm$^{-1}$ of >4;
a ratio of the area of the symmetric SO stretch of the sulphate band at about 1,063 cm$^{-1}$ to the area of the phenylalanine ring breathing band at about 1,003 cm$^{-1}$ of <1;
a ratio of the area of the low-wavenumber band of the O—H stretch complex at about 3,210 cm$^{-1}$ to the area of the high-wavenumber band of the O—H stretch complex at about 3,380 cm$^{-1}$ of >3.7; and
a ratio of the area of the proline band at about 856 cm$^{-1}$ to the area of the hydroxyproline band at about 877 cm$^{-1}$ of >1.5.

\* \* \* \* \*